US009649390B2

(12) United States Patent
Howard et al.

(10) Patent No.: US 9,649,390 B2
(45) Date of Patent: May 16, 2017

(54) PYRROLOBENZODIAZEPINES AND CONJUGATES THEREOF

(71) Applicant: MEDIMMUNE LIMITED, Cambridge (GB)

(72) Inventors: Philip Wilson Howard, London (GB); John A. Flygare, South San Francisco, CA (US); Thomas Pillow, South San Francisco, CA (US); Binqing Wei, South San Francisco, CA (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 14/774,535

(22) PCT Filed: Mar. 13, 2014

(86) PCT No.: PCT/IB2014/001029

§ 371 (c)(1),
(2) Date: Sep. 10, 2015

(87) PCT Pub. No.: WO2014/140862

PCT Pub. Date: Sep. 18, 2014

(65) Prior Publication Data

US 2016/0144052 A1 May 26, 2016

Related U.S. Application Data

(60) Provisional application No. 61/856,351, filed on Jul. 19, 2013, provisional application No. 61/778,777, filed on Mar. 13, 2013.

(51) Int. Cl.

| | |
|---|---|
| ***C07D 487/04*** | (2006.01) |
| ***A61K 47/48*** | (2006.01) |
| ***C07D 519/00*** | (2006.01) |
| ***A61K 31/5517*** | (2006.01) |
| ***C07K 16/28*** | (2006.01) |
| ***C07K 16/40*** | (2006.01) |

(52) U.S. Cl.

CPC .... *A61K 47/48646* (2013.01); *A61K 31/5517* (2013.01); *A61K 47/48384* (2013.01); *A61K 47/48584* (2013.01); *C07D 519/00* (2013.01); *C07K 16/2863* (2013.01); *C07K 16/40* (2013.01); *C07K 2317/92* (2013.01)

(58) Field of Classification Search

CPC .................................................. C07D 487/04

See application file for complete search history.

(56) References Cited

U.S. PATENT DOCUMENTS

| | | | |
|---|---|---|---|
| 6,562,806 | B1 | 5/2003 | Thurston et al. |
| 6,608,192 | B1 | 8/2003 | Thurston et al. |
| 6,660,742 | B2 | 12/2003 | Lee et al. |
| 6,747,144 | B1 | 6/2004 | Thurston et al. |
| 6,909,006 | B1 | 6/2005 | Thurston et al. |
| 7,049,311 | B1 | 5/2006 | Thurston et al. |
| 7,067,511 | B2 | 6/2006 | Thurston et al. |
| 7,265,105 | B2 | 9/2007 | Thurston et al. |
| 7,407,951 | B2 | 8/2008 | Thurston et al. |
| 7,429,658 | B2 | 9/2008 | Howard et al. |
| 7,528,126 | B2 | 5/2009 | Howard et al. |
| 7,557,099 | B2 | 7/2009 | Howard et al. |
| 7,612,062 | B2 | 11/2009 | Gregson et al. |
| 7,704,924 | B2 | 4/2010 | Thurston et al. |
| 7,741,319 | B2 | 6/2010 | Howard et al. |
| 8,034,808 | B2 | 10/2011 | Delavault et al. |
| 8,487,092 | B2 | 7/2013 | Howard et al. |

(Continued)

FOREIGN PATENT DOCUMENTS

| | | |
|---|---|---|
| WO | 00/12506 | 3/2000 |
| WO | WO 00/12507 | 3/2000 |

(Continued)

OTHER PUBLICATIONS

Jeffrey SC, et al., "A potent anti-CD70 antibody-drug conjugate combining a dimeric pyrrolobenzodiazepine drug with site-specific conjugation technology." Bioconjug Chem. Jul. 17, 2013;24(7): 1256-1263. Jun. 28, 2013.

(Continued)

*Primary Examiner* — Bruck Kifle

(74) *Attorney, Agent, or Firm* — Michael Best & Friedrich LLP

(57) ABSTRACT

A conjugate of formula (A):

A

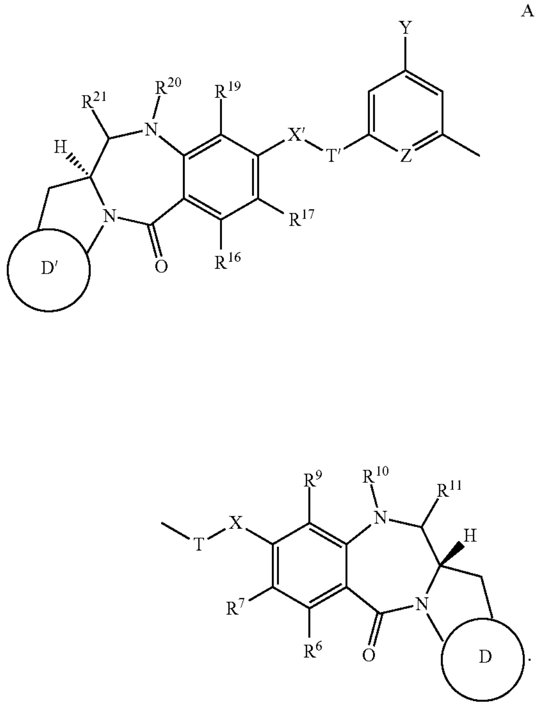

13 Claims, No Drawings

(56) References Cited

U.S. PATENT DOCUMENTS

| | | | |
|---|---|---|---|
| 8,501,934 | B2 | 8/2013 | Howard et al. |
| 8,592,576 | B2 | 11/2013 | Howard et al. |
| 8,633,185 | B2 | 1/2014 | Howard et al. |
| 8,637,664 | B2 | 1/2014 | Howard et al. |
| 8,697,688 | B2 | 4/2014 | Howard et al. |
| 8,829,184 | B2 | 9/2014 | Howard et al. |
| 8,940,733 | B2 | 1/2015 | Howard et al. |
| 9,102,704 | B2 | 8/2015 | Howard |
| 9,242,013 | B2 | 1/2016 | Howard et al. |
| 2003/0195196 | A1 | 10/2003 | Thurston et al. |
| 2004/0198722 | A1 | 10/2004 | Thurston et al. |
| 2007/0154906 | A1 | 7/2007 | Martin et al. |
| 2007/0191349 | A1 | 8/2007 | Howard et al. |
| 2007/0249591 | A1 | 10/2007 | Howard et al. |
| 2008/0090812 | A1 | 4/2008 | Pepper et al. |
| 2009/0036431 | A1 | 2/2009 | Gauzy et al. |
| 2009/0274713 | A1 | 11/2009 | Chari et al. |
| 2009/0304710 | A1 | 12/2009 | Park et al. |
| 2010/0028346 | A1 | 2/2010 | Lutz et al. |
| 2010/0047257 | A1 | 2/2010 | Blanc et al. |
| 2010/0203007 | A1 | 8/2010 | Li et al. |
| 2010/0316656 | A1 | 12/2010 | Bouchard et al. |
| 2011/0039969 | A1 | 2/2011 | Muratoglu et al. |
| 2011/0160192 | A1 | 6/2011 | Howard et al. |
| 2011/0195021 | A1 | 8/2011 | Deckert et al. |
| 2011/0195022 | A1 | 8/2011 | Deckert et al. |
| 2011/0256157 | A1 | 10/2011 | Howard et al. |
| 2012/0233172 | A1 | 9/2012 | Skillcorn et al. |
| 2012/0238731 | A1 | 9/2012 | Fishkin et al. |
| 2013/0028917 | A1 | 1/2013 | Howard et al. |
| 2013/0137659 | A1 | 5/2013 | Commercon et al. |
| 2013/0244171 | A1 | 9/2013 | Yamasaki et al. |
| 2013/0266595 | A1 | 10/2013 | Flygare et al. |
| 2013/0266596 | A1 | 10/2013 | Li et al. |
| 2013/0302359 | A1 | 11/2013 | Li et al. |
| 2013/0304357 | A1 | 11/2013 | Koci et al. |
| 2014/0030279 | A1 | 1/2014 | Polakis et al. |
| 2014/0030280 | A1 | 1/2014 | Polakis et al. |
| 2014/0066435 | A1 | 3/2014 | Howard et al. |
| 2014/0088089 | A1 | 3/2014 | Chari |
| 2014/0120118 | A1 | 5/2014 | Howard |
| 2014/0127239 | A1 | 5/2014 | Howard |
| 2014/0155590 | A1 | 6/2014 | Commercon et al. |
| 2014/0234346 | A1 | 8/2014 | Howard |
| 2014/0274907 | A1 | 9/2014 | Howard et al. |
| 2014/0286970 | A1 | 9/2014 | Jeffrey et al. |
| 2014/0294868 | A1 | 10/2014 | Howard et al. |
| 2014/0302066 | A1 | 10/2014 | Jeffrey et al. |
| 2015/0111880 | A1 | 4/2015 | Howard et al. |
| 2015/0126495 | A1 | 5/2015 | Howard et al. |
| 2015/0133435 | A1 | 5/2015 | Howard et al. |
| 2015/0158869 | A1 | 6/2015 | Howard |
| 2015/0183883 | A1 | 7/2015 | Asundi |
| 2015/0265722 | A1 | 9/2015 | Van Berkel |
| 2015/0273077 | A1 | 10/2015 | Van Berkel |
| 2015/0273078 | A1 | 10/2015 | Van Berkel |
| 2015/0274737 | A1 | 10/2015 | Howard et al. |
| 2015/0283258 | A1 | 10/2015 | Van Berkel |
| 2015/0283262 | A1 | 10/2015 | Van Berkel |
| 2015/0283263 | A1 | 10/2015 | Van Berkel |
| 2015/0297746 | A1 | 10/2015 | Van Berkel |
| 2015/0315196 | A1 | 11/2015 | Howard et al. |
| 2015/0344482 | A1 | 12/2015 | Howard et al. |
| 2016/0015828 | A1 | 1/2016 | Torgor |
| 2016/0031887 | A1 | 2/2016 | Howard et al. |

FOREIGN PATENT DOCUMENTS

| | | |
|---|---|---|
| WO | WO 00/12508 | 3/2000 |
| WO | WO 00/12509 | 3/2000 |
| WO | WO 01/16104 | 3/2001 |
| WO | WO 2004/043963 | 5/2004 |
| WO | WO 2005/023814 | 3/2005 |
| WO | WO 2005/042535 | 5/2005 |
| WO | WO 2005/085177 | 9/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/105113 | 11/2005 |
| WO | WO 2005/110423 | 11/2005 |
| WO | WO 2006/111759 | 10/2006 |
| WO | WO 2007/039752 | 4/2007 |
| WO | WO 2007/085930 | 8/2007 |
| WO | WO 2008/050140 | 5/2008 |
| WO | WO 2009/016516 | 2/2009 |
| WO | WO 2009/060208 | 5/2009 |
| WO | WO 2009/060215 | 5/2009 |
| WO | WO 2010/010347 | 1/2010 |
| WO | WO 2010/043877 | 4/2010 |
| WO | WO 2010/043880 | 4/2010 |
| WO | WO 2010/091150 | 8/2010 |
| WO | WO 2011/023883 | 3/2011 |
| WO | WO 2011/128650 | 10/2011 |
| WO | WO 2011/130598 | 10/2011 |
| WO | WO 2011/130613 | 10/2011 |
| WO | WO 2011/130616 | 10/2011 |
| WO | WO 2011/133039 | 10/2011 |
| WO | WO 2012/014147 | 2/2012 |
| WO | WO 2012/112687 | 8/2012 |
| WO | WO 2012/112708 | 8/2012 |
| WO | WO 2012/128868 | 9/2012 |
| WO | WO 2013/041606 | 3/2013 |
| WO | WO 2013/053871 | 4/2013 |
| WO | WO 2013/053872 | 4/2013 |
| WO | WO 2013/053873 | 4/2013 |
| WO | WO 2013/055987 | 4/2013 |
| WO | WO 2013/055990 | 4/2013 |
| WO | WO 2013/055993 | 4/2013 |
| WO | WO 2013/164592 | 11/2013 |
| WO | WO 2013/164593 | 11/2013 |
| WO | WO 2014/011518 | 1/2014 |
| WO | WO 2014/011519 | 1/2014 |
| WO | WO 2014/022679 | 2/2014 |
| WO | WO 2014/057072 | 4/2014 |
| WO | WO 2014/057073 | 4/2014 |
| WO | WO 2014/057074 | 4/2014 |
| WO | WO 2014/057113 | 4/2014 |
| WO | WO 2014/057114 | 4/2014 |
| WO | WO 2014/057115 | 4/2014 |
| WO | WO 2014/057117 | 4/2014 |
| WO | WO 2014/057118 | 4/2014 |
| WO | WO 2014/057119 | 4/2014 |
| WO | WO 2014/057120 | 4/2014 |
| WO | WO 2014/057122 | 4/2014 |
| WO | WO 2014/096365 | 6/2014 |
| WO | WO 2014/096368 | 6/2014 |
| WO | WO 2014/130879 | 8/2014 |
| WO | WO 2014/140174 | 9/2014 |
| WO | WO 2014/140862 | 9/2014 |
| WO | WO 2014/159981 | 10/2014 |
| WO | WO 2014/174111 | 10/2014 |
| WO | WO 2015/052321 | 4/2015 |
| WO | WO 2015/052322 | 4/2015 |
| WO | WO 2015/052532 | 4/2015 |
| WO | WO 2015/052533 | 4/2015 |
| WO | WO 2015/052534 | 4/2015 |
| WO | WO 2015/052535 | 4/2015 |
| WO | WO 2015/095124 | 6/2015 |
| WO | WO 2015/159076 | 10/2015 |

OTHER PUBLICATIONS

International Search Report and Written Opinion for Application No. PCT/IB2014/001029 dated Oct. 23, 2014 (8 pages).

U.S. Appl. No. 14/995,944, filed Jan. 14, 2016, Howard et al.

PYRROLOBENZODIAZEPINES AND CONJUGATES THEREOF

The present invention relates to pyrrolobenzodiazepines (PBDs), in particular pyrrolobenzodiazepines having a linker group connected to a cell binding agent.

BACKGROUND TO THE INVENTION

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.,* 87, 5793-5795 (1965); Leimgruber, et al, *J. Am. Chem. Soc.,* 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., Chem. Rev. 2011 111 (4), 2815-2864). Family members include abbeymycin (Hochlowski, et al., *J. Antibiotics,* 40, 145-148 (1987)), chicamycin (Konishi, et al., *J. Antibiotics,* 37, 200-206 (1984)), DC-81 (Japanese Patent 58-180 487; Thurston, et al., *Chem. Brit.,* 26, 767-772 (1990); Bose, et al., *Tetrahedron,* 48, 751-758 (1992)), mazethramycin (Kuminoto, et al., *J. Antibiotics,* 33, 665-667 (1980)), neothramycins A and B (Takeuchi, et al., *J. Antibiotics,* 29, 93-96 (1976)), porothramycin (Tsunakawa, et al., *J. Antibiotics,* 41, 1366-1373 (1988)), prothracarcin (Shimizu, et al, *J. Antibiotics,* 29, 2492-2503 (1982); Langley and Thurston, *J. Org. Chem.,* 52, 91-97 (1987)), sibanomicin (DC-102) (Hara, et al., *J. Antibiotics,* 41, 702-704 (1988); Itoh, et al., *J. Antibiotics,* 41, 1281-1284 (1988)), sibiromycin (Leber, et al., *J. Am. Chem. Soc.,* 110, 2992-2993 (1988)) and tomamycin (Arima, et al., *J. Antibiotics,* 25, 437-444 (1972)). PBDs are of the general structure:

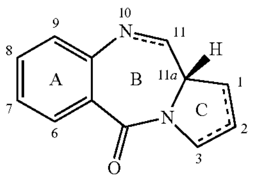

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III.* Springer-Verlag, New York, pp. 3-11 (1975); Hurley and Needham-VanDevanter, *Acc. Chem. Res.,* 19, 230-237 (1986)). Their ability to form an adduct in the minor groove, enables them to interfere with DNA processing, hence their use as antitumour agents.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SJG-136, is shown below:

SJG-136

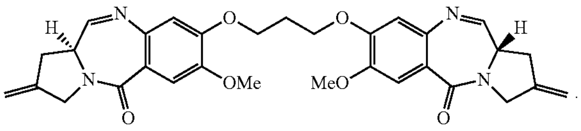

Other dimeric PBD compounds, such as those bearing C2 aryl substituents in WO 2005/085251, have been disclosed, an example being:

ZC-207

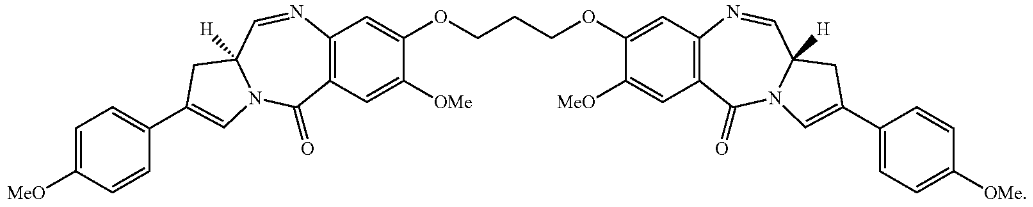

These compounds have been shown to be highly useful cytotoxic agents.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells as well as the tumor cells sought to be eliminated (Xie et al (2006) *Expert. Opin. Biol. Ther.* 6(3):281-291; Kovtun et al (2006) *Cancer Res.* 66(6):3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P.

(2005) *Expert Opin. Ther. Patents* 15(9):1087-1103; Payne, G. (2003) *Cancer Cell* 3:207-212; Trail et al (2003) *Cancer Immuno. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Dornan et al (2009) *Blood* 114(13):2721-2729; U.S. Pat. No. 7,521,541; U.S. Pat. No. 7,723,485; WO2009/052249; McDonagh (2006) Protein Eng. Design & Sel. 19(7): 299-307; Doronina et al (2006) Bioconj. Chem. 17:114-124; Erickson et al (2006) *Cancer Res.* 66(8):1-8; Sanderson et al (2005) *Clin. Cancer Res.* 11:843-852; Jeffrey et al (2005) *J. Med. Chem.* 48:1344-1358; Hamblett et al (2004) *Clin. Cancer Res.* 10:7063-7070). Drug moieties may impart their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

PBDs in ADCs

Dimeric PBDs have been disclosed as the drugs in drug conjugates. For example, in WO 2011/130598, dimer PBD compounds having linker groups for connection to a cell binding agent, such as an antibody, are disclosed where the linker group is attached to one of the available N10 positions, and are generally cleaved by action of an enzyme on the linker group.

By contrast, in WO 2011/130613 and WO 2011/130616, dimer PBD compounds having linker groups for connection to a cell binding agent, such as an antibody, are disclosed where the linker group is attached via an aromatic group at one of the C2 positions, and are generally cleaved by action of an enzyme on the linker group. Such antibody drug conjugates are also described in Flygare, J., et al, *Chem. Biol. Drug Des.* 81: 113-121 (2013), which also describes other types of antibody drug conjugates.

A further approach is described in WO 2007/085930, wherein tomamycin-like dimers have a linker group for connection to a cell binding agent, such as an antibody, where the linker group is attached to the tether between the tomamycin units, and are generally cleaved by action of an enzyme on the linker group.

The present inventors have developed a novel approach to forming PBD conjugates with cell binding agents, and in particular PBD antibody conjugates.

SUMMARY OF THE INVENTION in a general aspect the present invention provides a conjugate comprising a PBD dimer compound with a linker for connecting to a cell binding agent, wherein the linker has a triazole, piperazine, propargylene or oxime group attached to a phenylene or pyriydylene in the bridge linking the two PBD monomers. The cell binding agent is preferably an antibody.

In a first aspect, the present invention provides novel conjugate compounds of formula (A):

A

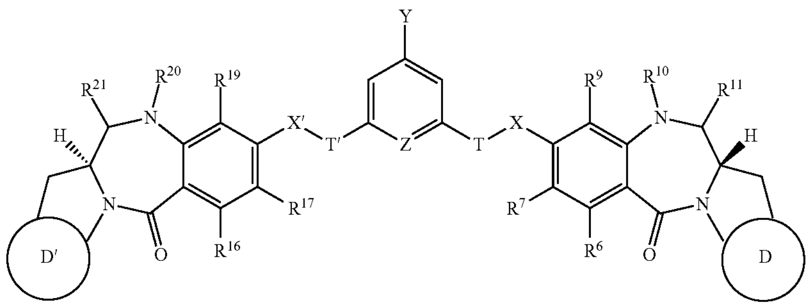

wherein:

D represents either group D1 or D2:

D1

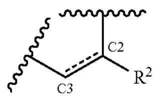

D2

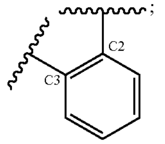

the dotted line indicates the optional presence of a double bond between C2 and C3; when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

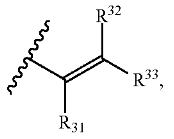

wherein each of $R^{31}$, $R^{32}$ and $R^{33}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

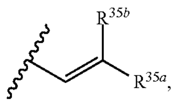

wherein one of $R^{35a}$ and $R^{35b}$ is H and the other is selected from:

phenyl, which phenyl is optionally substituted by a group selected from halo, methyl, methoxy; pyridyl; and thiophenyl; and (if)

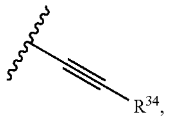

where $R^{34}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

(ig) halo;

when there is a single bond present between C2 and C3, $R^2$ is

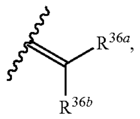

where $R^{36a}$ and $R^{36b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$, alkyl ester;

D' represents either group D'1 or D'2:

D'1

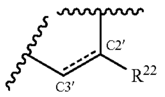

D'2

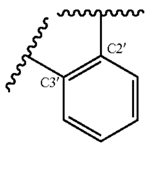

wherein the dotted line indicates the optional presence of a double bond between C2' and C3';

$R^6$ and $R^9$ are independently selected from H, R, OH, OR, SH, SR, $NH_2$, NHR, NRR', $NO_2$, $Me_3Sn$ and halo;

$R^7$ is independently selected from H, R, OH, OR, SH, SR, $NH_2$, NHR, NRR', $NO_2$, $Me_3Sn$ and halo;

Y is selected from formulae A1, A2, A3, A4, A5 and A6:

(A1)

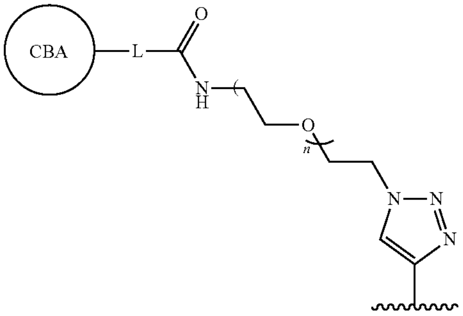

(A2)

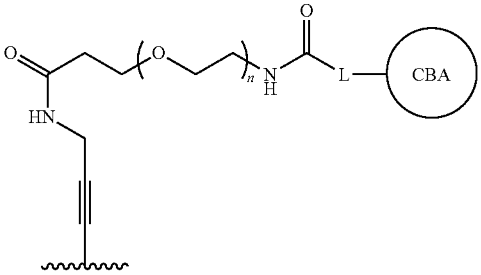

(A3)

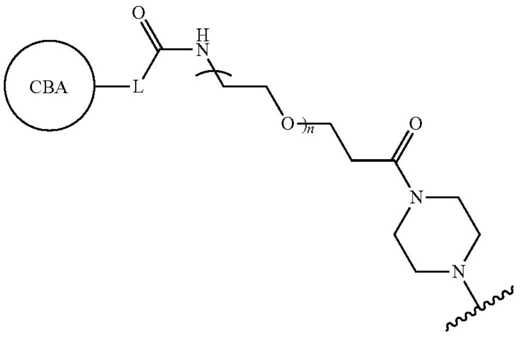

-continued (A4)

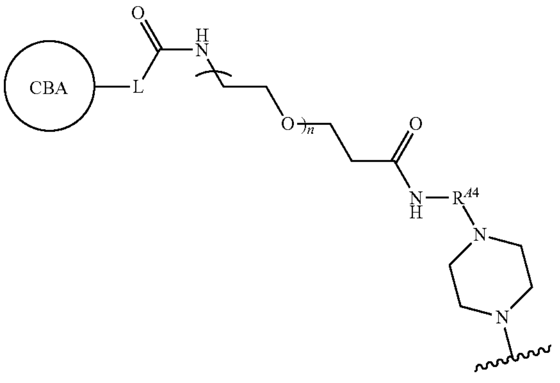

(A5)

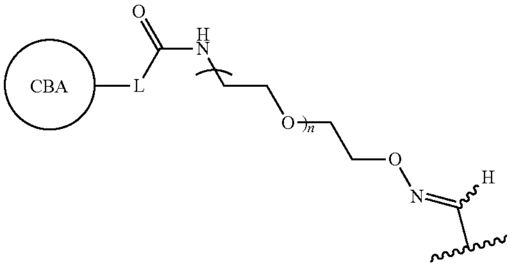

(A6)

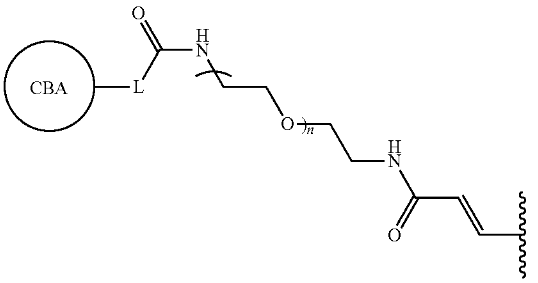

L is a linker connected to a cell binding agent;

CBA is the cell binding agent;

n is an integer selected in the range of 6 to 48;

$R^{A4}$ a $C_{1-6}$ alkylene group;

either (a) $R^{10}$ is H, and $R^{11}$ is OH, $OR^A$, where $R^A$ is $C_{1-4}$ alkyl; or (b) $R^{10}$ and $R^{11}$ form a nitrogen-carbon double bond between the nitrogen and carbon atoms to which they are bound; or (c) $R^{10}$ is H and $R^{11}$ is $OSO_zM$, where z is 2 or 3 and M is a monovalent pharmaceutically acceptable cation;

R and R' are each independently selected from optionally substituted $C_{1-12}$ alkyl, $C_{3-20}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

wherein $R^{16}$, $R^{17}$, $R^{19}$, $R^{20}$, $R^{21}$ and $R^{22}$ are as defined for $R^6$, $R^7$, $R^9$, $R^{10}$, $R^{11}$ and $R^2$ respectively;

wherein Z is CH or N;

wherein T and T' are independently selected from a single bond or a $C_{1-9}$ alkylene, which chain may be interrupted by one or more heteroatoms e.g. O, S, N(H), NMe, provided that the number of atoms in the shortest chain of atoms between X and X' is 3 to 12 atoms;

X and X' are independently selected from O, S and N(H);

except that there cannot be double bonds between both C2 and C3 and C2' and C3'.

Thus formula A is selected from the following formulae A-I, A-II, A-III, A-IV, A-V and A-VI depending on Y:

| Y | A |
|---|---|
| A1 | 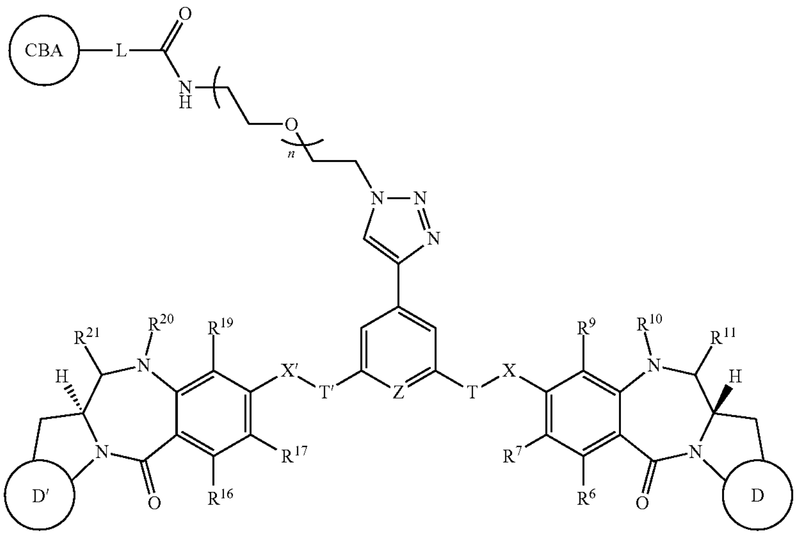 (A-I) |

-continued
| Y | A | |
|---|---|---|
| A2 | 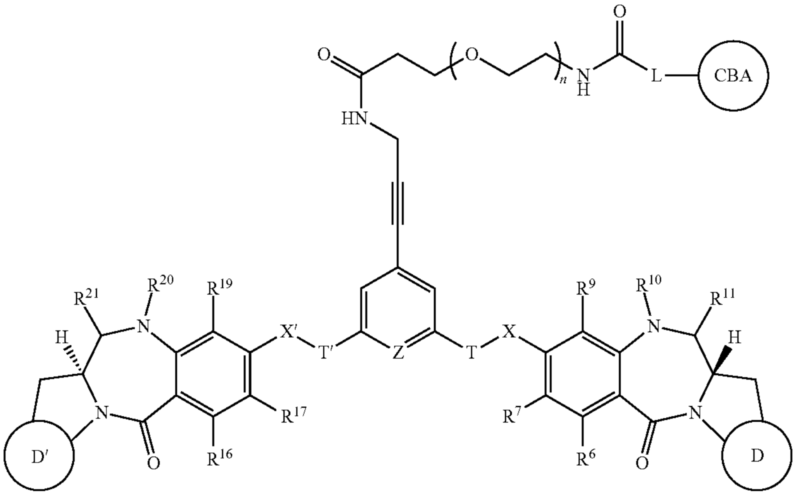 | (A-II) |
| A3 | 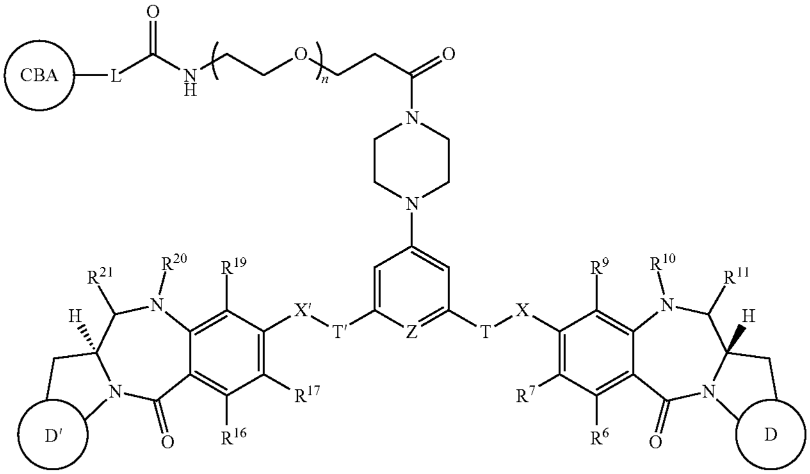 | (A-III) |
| A4 | 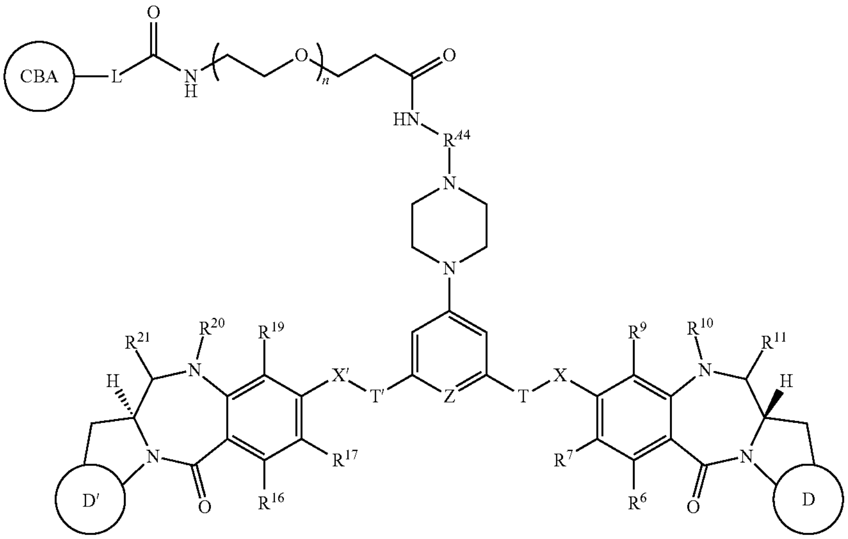 | (A-IV) |

-continued
| Y | A |
|---|---|
| A5 | 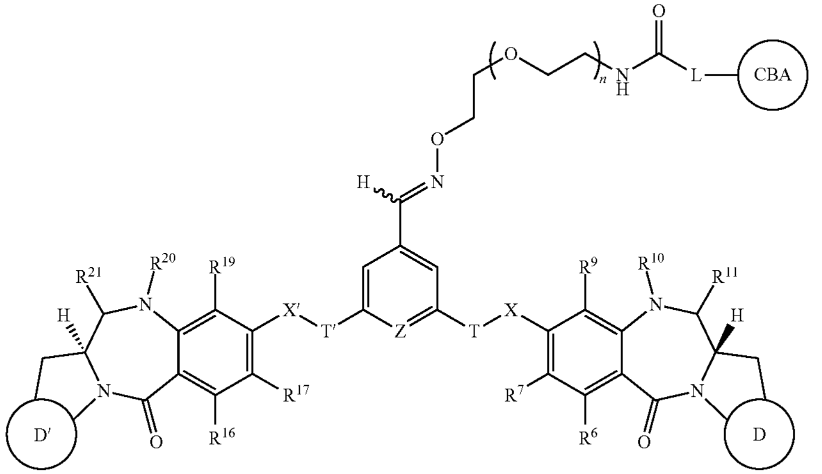 (A-V) |
| A6 | 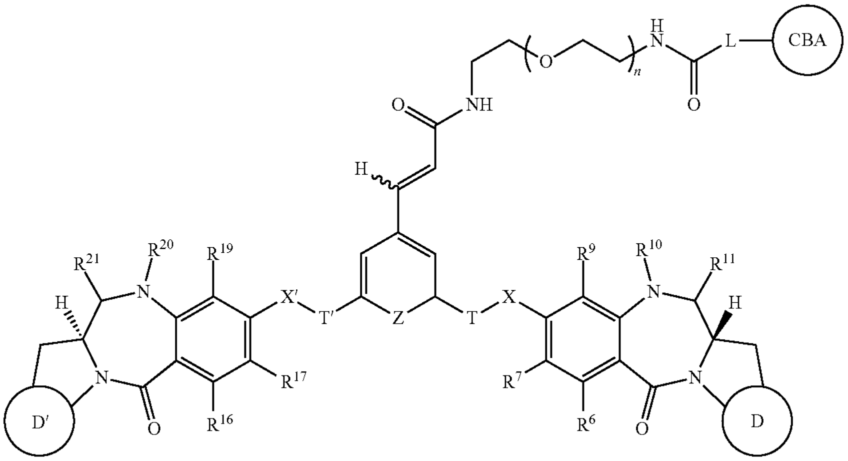 |
A second aspect of the present invention provides novel drug-linker compounds of formula (B):
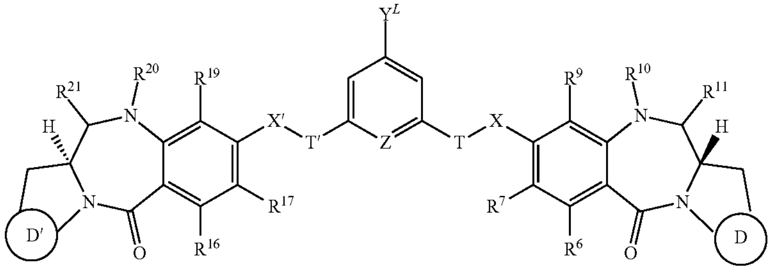
B
Where all the groups are as defined in the first aspect of the invention; and
$Y^L$ is selected from a group of formulae B1, B2, B3, 84, B5 and B6:

-continued
(B1)
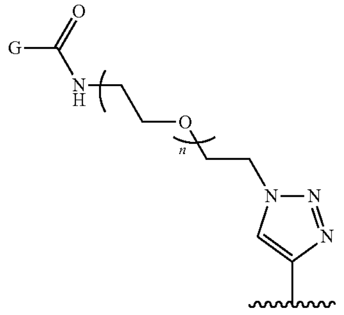
(B2)
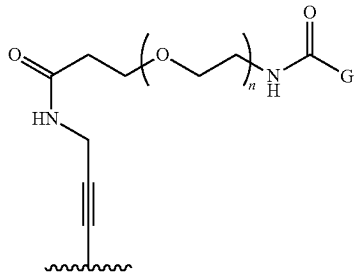
(B3)
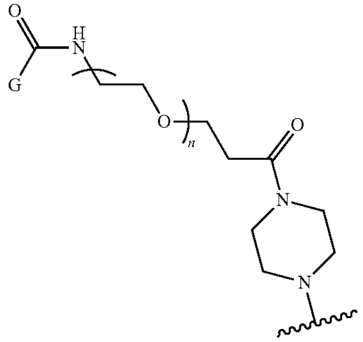
(B4)
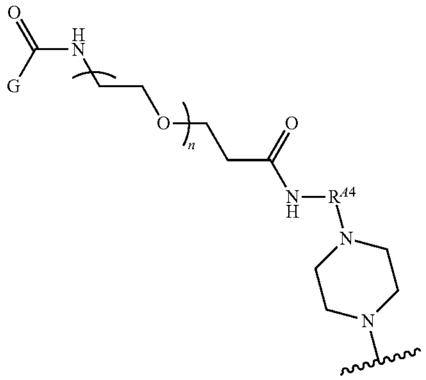
(B5)
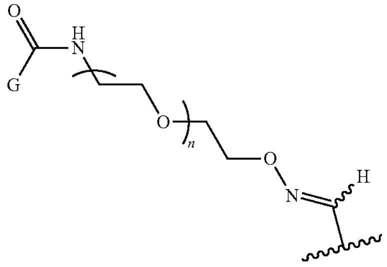
(B6)
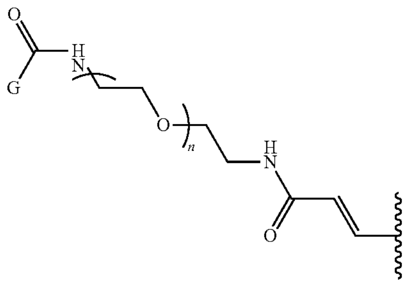
where G is a reactive group for connecting to a cell binding agent.
A third aspect of the present invention provides compounds of formula (C) which may be used in the preparation of the compounds and conjugate compounds of the invention:

C

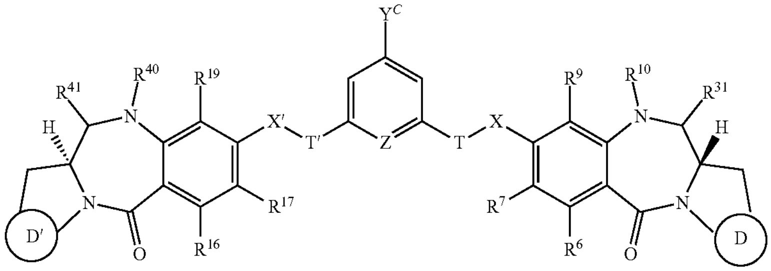

where $Y^C$ is selected from a group of formulae C1, C2, C3, C4, C5 and C6:

(C1)

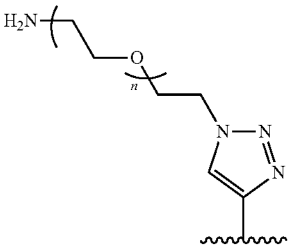

(C2)

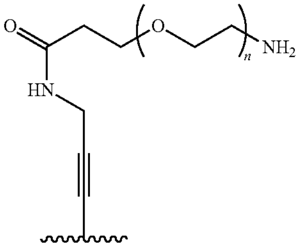

(C3)

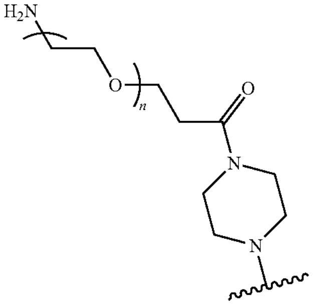

(C4)

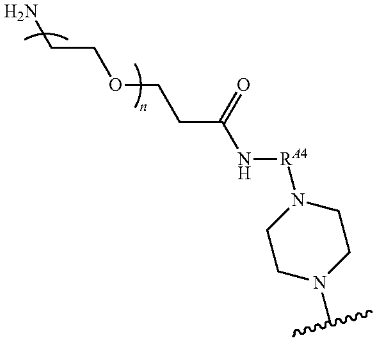

-continued (C5)

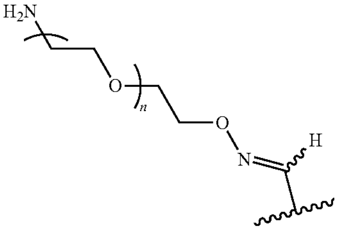

(C6)

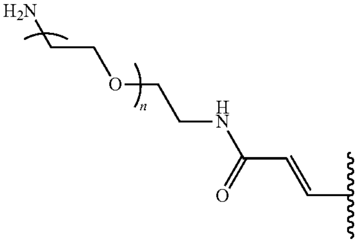

either (a) $R^{30}$ is H, and $R^{31}$ is OH, $OR^A$, where $R^A$ is $C_{1-4}$ alkyl; or (b) $R^{30}$ and $R^{31}$ form a nitrogen-carbon double bond between the nitrogen and carbon atoms to which they are bound; or (c) $R^{30}$ is H and $R^{31}$ is $OSO_zM$, where z is 2 or 3 and M is a monovalent pharmaceutically acceptable cation; or (d) $R^{30}$ is a nitrogen protecting group and $R^{31}$ is $OProt^O$, where $Prot^O$ is a hydroxy protecting group; and $R^{40}$ and $R^{41}$ are as defined for $R^{30}$ and $R^{31}$ respectively; and all the remaining groups are as defined in the first aspect of the invention.

A fourth aspect of the present invention provides compounds of formula (D) which may be used in the preparation of the compounds of the second and third aspects of the invention:

D

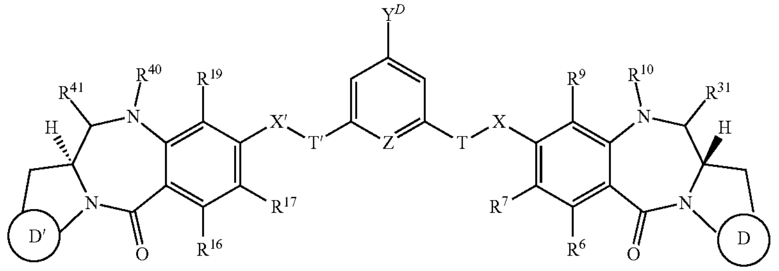

$Y^D$ is selected from a group of formulae D2, D3, D4 and D6:

(D2)

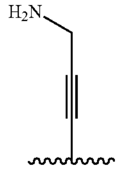

(D3)

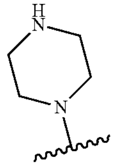

(D4)

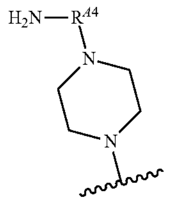

(D6)

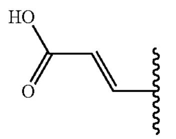

and all the remaining groups are as defined in the third aspect of the invention.

A fifth aspect of the present invention provides compounds of formula (E) which may be used in the preparation of the compounds of the second, third and fourth aspects of the invention:

E

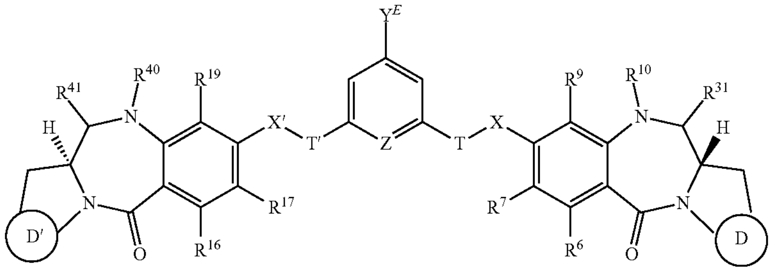

$Y^E$ is selected from a group of formulae E1, E2 and E5:

(E1)

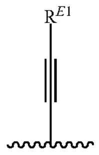

(E2)

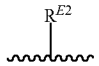

(E5)

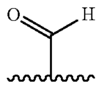

where $R^{E1}$ is selected from H and TMS;

$R^{E2}$ is selected from Br, Cl and I; and all the remaining groups are as defined in the third aspect of the invention.

A sixth aspect of the present invention provides the use of a compound of the first aspect of the invention in a method of medical treatment. The fourth aspect also provides a pharmaceutical composition comprising a compound of the first aspect, and a pharmaceutically acceptable excipient.

A seventh aspect of the present invention provides a compound of the first aspect of the invention or a pharmaceutical composition of the fourth aspect of the invention for use in a method of treatment of a proliferative disease. The fifth aspect also provides the use of a compound of the first aspect in a method of manufacture of a medicament for the treatment of a proliferative disease, and a method of treating a mammal having a proliferative disease, comprising administering an effective amount of a compound of the first aspect or a pharmaceutical composition of the fourth aspect.

An eight aspect of the present invention provides a method of synthesis of a compound of the first aspect of the present invention, comprising the step of conjugating a drug-linker of the second aspect with a cell-binding agent.

The present invention also provides the synthesis of compounds of the second aspect of the invention from compounds of the third, fourth or fifth aspect of the invention by reacting them with suitable reagents.

DETAILED DESCRIPTION OF THE INVENTION

The present invention provides a conjugate comprising a PBD dimer connected through the dimer bridging portion via a specified linker to a cell binding agent.

The present invention is suitable for use in providing a PBD conjugate to a preferred site in a subject.

Nitrogen Protecting Groups

Nitrogen protecting groups are well known in the art. Preferred nitrogen protecting groups for use in the present invention are carbamate protecting groups that have the general formula:

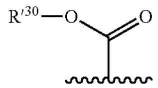

wherein $R'^{30}$ is an optionally substituted alkyl (e.g. $C_{1-20}$ alkyl), aryl (e.g. $C_{5-20}$ aryl) or heteroaryl (e.g. $C_{3-20}$ heterocyclyl) group.

A large number of possible carbamate nitrogen protecting groups are listed on pages 706 to 772 of Greene's Protective Groups in Organic Synthesis, $4^{th}$ Edition, John Wiley & Sons, Inc., 2007 (ISBN 978-0-471-69754-1), which is incorporated herein by reference.

Particularly preferred protecting groups include Alloc, Troc, Teoc, BOC, TcBOC, Fmoc, 1-Adoc and 2-Adoc.

Hydroxyl Protecting Groups

Hydroxyl protecting groups are well known in the art. A large number of suitable groups are described on pages 24 to 298 of Greene's Protective Groups in Organic Synthesis, $4^{th}$ Edition, John Wiley & Sons, Inc., 2007 (ISBN 978-0-471-69754-1), which is incorporated herein by reference.

Classes of particular interest include silyl ethers, methyl ethers, alkyl ethers, benzyl ethers, esters, benzoates, carbonates, and sulfonates. Particularly preferred hydroxyl protecting groups include THP.

Preferences

The following preferences may apply to all aspects of the invention as described above, or may relate to a single aspect. The preferences may be combined together in any combination.

$R^2$

When $R^2$ is a $C_{5-10}$ aryl group, in some embodiments it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^2$ may be phenyl. In other embodiments, $R^2$ may be thiophenyl, for example, thiophen-2-yl and thiophen-3-yl.

When $R^2$ is a $C_{5-10}$ aryl group, it some embodiments it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^2$ is a $C_{5-10}$ aryl group, it may bear any number of substituent groups. In some embodiments, it may bear from 1 to 3 substituent groups. In some embodiments, it may bear 1 or 2 substituent groups. In some embodiments, it may bear a single substituent group. The substituents may be any position.

Where $R^2$ is $C_{5-7}$ aryl group, in some embodiments a single substituent may be on a ring atom that is not adjacent the bond to the remainder of the compound, i.e. it may be β or γ to the bond to the remainder of the compound. Therefore, in embodiments where the $C_{5-7}$ aryl group is phenyl, the substituent may be in the meta- or para-positions, or may be in the para-position.

Where $R^2$ is a $C_{8-10}$ aryl group, for example quinolinyl or isoquinolinyl, in some embodiments there may be any number of substituents at any position of the quinoline or isoquinoline rings. In some embodiments, it bears one, two or three substituents, and these may be on either the proximal and distal rings or both (if more than one substituent).

$R^2$ Substituents, when $R^2$ is a $C_{5-10}$ aryl Group

In embodiments where a substituent on $R^2$ when $R^2$ is a $C_{5-10}$ aryl group is halo, it may be F or Cl, and in some of these embodiments Cl.

In embodiments where a substituent on $R^2$ when $R^2$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g. phenoxy, pyridyloxy, furanyloxy). The alkoxy group may itself be further substituted, for example by an amino group (e.g. dimethylamino).

In embodiments where a substituent on $R^2$ when $R^2$ is a $C_{5-10}$ aryl group is $C_{1-7}$ alkyl, it may be a $C_{1-4}$ alkyl group (e.g. methyl, ethyl, propryl, butyl).

In embodiments where a substituent on $R^2$ when $R^2$ is a $C_{5-10}$ aryl group is $C_{3-7}$ heterocyclyl, it may be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

In embodiments where a substituent on $R^2$ when $R^2$ is a $C_{5-10}$ aryl group is bis-oxy-$C_{1-3}$ alkylene, this may be bis-oxy-methylene or bis-oxy-ethylene.

In embodiments where a substituent on $R^2$ when $R^2$ is a $C_{5-10}$ aryl group is ester, this is preferably methyl ester or ethyl ester.

In some embodiments, substituents when $R^2$ is a $C_{5-10}$ aryl group may include methoxy, ethoxy, fluoro, chloro, cyano, bis-oxy-methylene, methyl-piperazinyl, morpholino, methyl-thiophenyl, dimethylaminopropyloxy and carboxy.

In some embodiments, $R^2$ may be selected from 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, naphthyl, 4-nitrophenyl, 4-(4-methylpiperazin-1-yl)phenyl and 3,4-bisoxymethylene-phenyl.

When $R^2$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^2$ is $C_{3-6}$ saturated cycloalkyl, it may be cyclopropyl, cyclobutyl, cyclopentyl or cyclohexyl. In some embodiments, it may be cyclopropyl.

When $R^2$ is

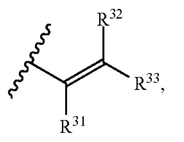

in some embodiments, the total number of carbon atoms in the $R^2$ group is no more than 4 or no more than 3.

In some embodiments, one of $R^{31}$, $R^{32}$ and $R^{33}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{31}$, $R^{32}$ and $R^{33}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that are not H are methyl.

In some embodiments, $R^{31}$ is H.

In some embodiments, $R^{32}$ is H.

In some embodiments, $R^{33}$ is H.

In some embodiments, $R^{31}$ and $R^{32}$ are H.

In some embodiments, $R^{31}$ and $R^{33}$ are H.

In some embodiments, $R^{32}$ and $R^{33}$ are H.

A $R^2$ group of particular interest is:

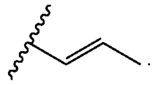 [SMILES: */C=C/C]

When $R^2$ is

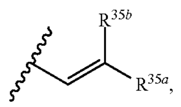

in some embodiments, the group ($R^{35a}$ or $R^{35b}$) which is not H is optionally substituted phenyl. If the phenyl optional substituent is halo, it may be fluoro. In some embodiment, the phenyl group is unsubstituted.

When $R^2$ is

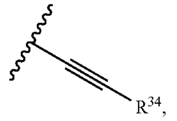

in some embodiments where $R^{34}$ is phenyl, it is unsubstituted. In other embodiments, the phenyl group bears a single fluoro substituent. In other embodiments, $R^{14}$ is selected from H, methyl, ethyl, ethenyl and ethynyl. In some of these embodiments, $R^{14}$ is selected from H and methyl.

When $R^2$ is halo, in some embodiments, it is fluoro.

When there is a single bond present between C2 and C3, $R^2$ is

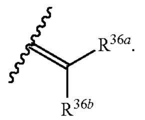

In some embodiments, $R^{36a}$ and $R^{36b}$ are both H.

In other embodiments, $R^{36a}$ and $R^{36b}$ are both methyl.

In further embodiments, one of $R^{36a}$ and $R^{36b}$ is H, and the other is selected from $C_{1-4}$ saturated alkyl, $C_{2-3}$ alkenyl, which alkyl and alkenyl groups are optionally substituted. In some of these further embodiment, the group which is not H may be selected from methyl and ethyl.

$R^{22}$

The above preferences for $R^2$ when there is a double bond present between C2 and C3 apply equally to $R^{22}$, when there is a double bond present between C2' and C3'.

The above preferences for $R^2$ when there is a single bond present between C2 and C3 apply equally to $R^{22}$, when there is a single bond present between C2' and C3'.

As described above, there cannot be double bonds between both C2 and C3 and C2' and C3'.

$R^6$

In one embodiment, $R^6$ is independently selected from H. R, OH, OR, SH, SR, $NH_2$, NHR, NRR', $NO_2$, $Me_3Sn$— and Halo.

In one embodiment, $R^6$ is independently selected from H, OH, OR, SH, $NH_2$, $NO_2$ and Halo.

In one embodiment, $R^6$ is independently selected from H and Halo.

In one embodiment, $R^6$ is independently H.

In one embodiment, $R^6$ and $R^7$ together form a group —O—$(CH_2)_p$—O—, where p is 1 or 2.

These embodiments also apply to $R^{16}$.

$R^7$ $R^7$ is independently selected from H, R, OH, OR, SH, SR, $NH_2$, NHR, NRR', $NO_2$, $Me_3Sn$ and halo.

In one embodiment, $R^7$ is independently OR.

In one embodiment, $R^7$ is independently $OR^{7A}$, where $R^{7A}$ is independently optionally substituted $C_{1-6}$ alkyl.

In one embodiment, $R^{7A}$ is independently optionally substituted saturated $C_{1-6}$ alkyl.

In one embodiment, $R^{7A}$ is independently optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

These embodiments also apply to $R^{17}$.

$R^9$

In one embodiment, $R^9$ is independently selected from H, R, OH, OR, SH, SR, $NH_2$, NHR, NRR', $NO_2$, $Me_3Sn$— and Halo.

In one embodiment, $R^9$ is independently H.

In one embodiment, $R^9$ is independently R or OR.

These embodiments also apply to $R^{19}$.

N10-C11

In some embodiments, $R^{10}$ is H, and $R^{11}$ is OH, $OR^A$, where $R^A$ is $C_{1-4}$ alkyl. In some of these embodiments, $R^{11}$ is OH. In others of these embodiments, $R^{11}$ is $OR^A$, where $R^A$ is $C_{1-4}$ alkyl. In some of these embodiments, $R^A$ is methyl.

In some embodiments, $R^{10}$ and $R^{11}$ form a nitrogen-carbon double bond between the nitrogen and carbon atoms to which they are bound.

In some embodiments, $R^{10}$ is H and $R^{11}$ is $OSO_zM$, where z is 2 or 3 and M is a monovalent pharmaceutically acceptable cation. In some of these embodiments, M is a monovalent pharmaceutically acceptable cation, and may be $Na^+$. Furthermore, in some embodiments z is 3.

The above preferences apply equally to $R^{20}$ and $R^{21}$.

In some embodiments, $R^{30}$ is H, and $R^{31}$ is OH, $OR^A$, where $R^A$ is $C_{1-4}$ alkyl. In some of these embodiments, $R^{31}$ is OH. In others of these embodiments, $R^{31}$ is $OR^A$, where $R^A$ is $C_{1-4}$ alkyl. In some of these embodiments, $R^A$ is methyl.

In some embodiments, $R^{30}$ and $R^{31}$ form a nitrogen-carbon double bond between the nitrogen and carbon atoms to which they are bound.

In some embodiments, $R^{30}$ is H and $R^{31}$ is $OSO_zM$, where z is 2 or 3 and M is a monovalent pharmaceutically acceptable cation. In some of these embodiments, M is a monovalent pharmaceutically acceptable cation, and may be $Na^+$. Furthermore, in some embodiments z is 3.

In some embodiments, $R^{30}$ is a nitrogen protecting group and $R^{31}$ is $OProt^O$, where $Prot^O$ is a hydroxy protecting group.

In some of these embodiments, the nitrogen protecting group may be selected from Alloc, Troc, Teoc, BOC, TcBOC, Fmoc, 1-Adoc and 2-Adoc, and more preferably be Boc.

In some of these embodiments, the nitrogen protecting group may be THP.

For compounds of formula D, it may be preferred that $R^{30}$ and $R^{31}$ form a nitrogen-carbon double bond between the nitrogen and carbon atoms to which they are bound.

For compounds of formula E, it may be preferred that $R^{30}$ is a nitrogen protecting group and $R^{31}$ is $OProt^O$, where $Prot^O$ is a hydroxy protecting group.

For compounds of formula C, where $Y^C$ is of formula C2, C3 or C4, it may be preferred that $R^{30}$ and $R^{31}$ form a nitrogen-carbon double bond between the nitrogen and carbon atoms to which they are bound.

For compounds of formula C, where $Y^C$ is of formula C1 or C5, it may be preferred that $R^{30}$ is a nitrogen protecting group and $R^{31}$ is $OProt^O$, where $Prot^O$ is a hydroxy protecting group.

The above preferences apply equally to $R^{40}$ and $R^{41}$.

T and T'

Each of T and T' is independently selected from a single bond or a $C_{1-9}$ alkylene group, which chain may be interrupted by one or more heteroatoms, e.g. O, S, N(H) and/or NMe, provided that the number of atoms in the shortest chain of atoms between X and X' is 3 to 12 atoms.

In one embodiment, each alkylene group of T and T' is optionally interrupted by one or more heteroatoms selected from O, S, and NMe.

In one embodiment, each of T and T' is independently selected from a single bond and a $C_{1-9}$ alkylene group.

In one embodiment, T is selected from a single bond, $C_1$, $C_2$, $C_3$ and a $C_4$ alkylene group and T' is selected from a single bond, $C_1$, $C_2$, $C_3$ and a $C_4$ alkylene group.

In one embodiment, T is selected from a single bond, $C_1$, and a $C_2$ alkylene group and T' is selected from a single bond, $C_1$, and a $C_2$ alkylene group.

In one embodiment, T is selected from a single bond and a C, alkylene group and T' is selected from a single bond and a $C_1$ alkylene group.

In one embodiment, T is a single bond and T' is a single bond.

In one embodiment, T is a $C_1$ alkylene group and T' is a $C_1$ alkylene group.

In some embodiments, T and T' are the same.

The alkylene groups listed above may be optionally interrupted by one or more heteroatoms.

The alkylene groups listed above may be unsubstituted linear aliphatic alkylene groups.

X

In one embodiment, X is selected from O, S, or N(H).

Preferably, X is O.

Dimers

In some embodiments, the groups $R^{22}$, $R^{16}$, $R^{17}$, $R^{19}$, $R^{20}$ and $R^{21}$ are the same as the groups $R^2$, $R^6$, $R^9$, $R^7$, $R^{10}$ and $R^{11}$ respectively. In these embodiments, the PBD monomer units have the same substituents.

Particularly preferred compounds of the first aspect of the present invention may be of formula Ia:

Ia

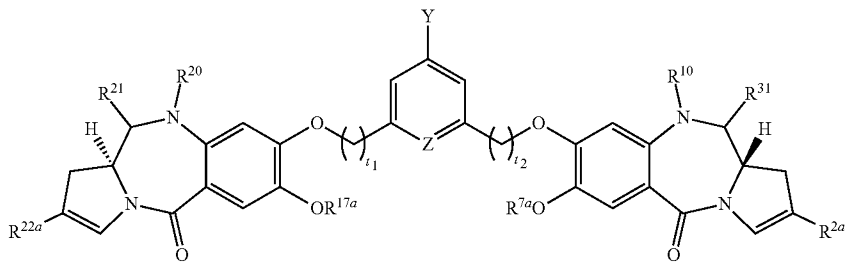

where $R^{10}$, $R^{11}$, $R^{12}$, $R^{21}$ and Y are as defined above;

$t_1$ and $t_2$ are an independently selected from 0, 1 and 2;

$R^{7a}$ and $R^{17a}$ are independently selected from methyl and phenyl;

$R^{2a}$ and $R^{22a}$ are independently selected from:

(a)

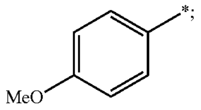

(b)

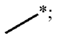

(c)

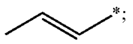

(d)

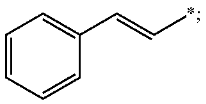

(e)

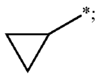

(f)

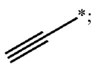

(g)

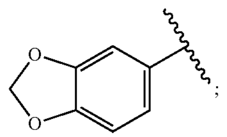

and (h)

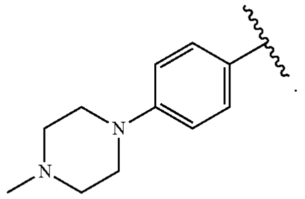

These compounds may preferably be symmetrical.

Particularly preferred compounds of the second aspect of the present invention may be of formula IIa:

IIa

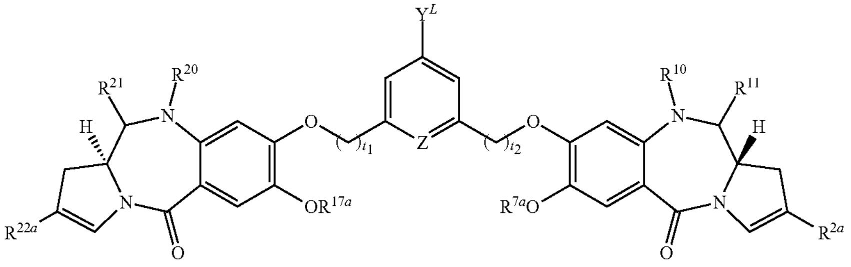

where $R^{10}$, $R^{11}$, $R^{20}$, $R^{21}$ and $Y^L$ are as defined above;

$t_1$ and $t_2$ are an independently selected from 0, 1 and 2;

$R^{7a}$ and $R^{17a}$ are independently selected from methyl and phenyl;

$R^{2a}$ and $R^{22a}$ are independently selected from:

(a)

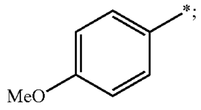

(b)

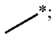

(c)
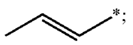
(d)
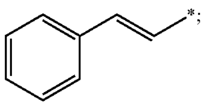
(e)
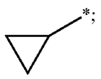
(f)
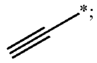
(g)
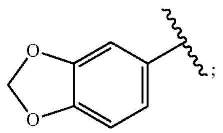 [SMILES: *c1ccc2c(c1)OCO2]
and
(h)
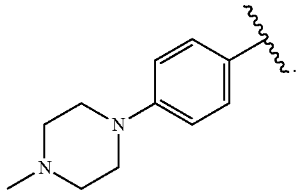 [SMILES: *c1ccc(N2CCN(C)CC2)cc1]
These compounds may preferably be symmetrical.
Particularly preferred compounds of the third aspect of the present invention may be of formula IIIa:
IIIa
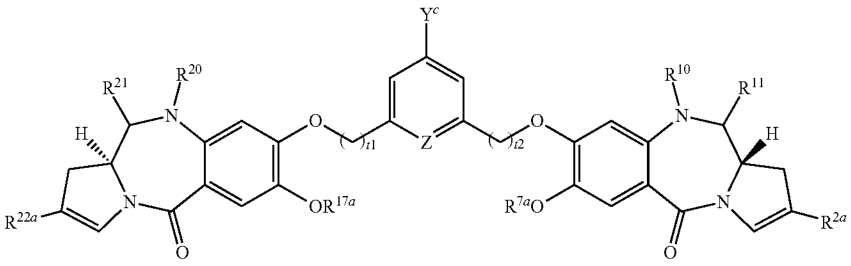

where $R^{10}$, $R^{11}$, $R^{20}$, $R^{21}$ and $Y^C$ are as defined above;

$t_1$ and $t_2$ are an independently selected from 0, 1 and 2;

$R^{7a}$ and $R^{17a}$ are independently selected from methyl and phenyl;

$R^{2a}$ and $R^{22a}$ are independently selected from:

(a)

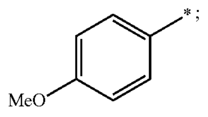 [SMILES: *c1ccc(OC)cc1]

(b)

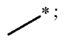

(c)

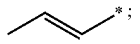

(d)

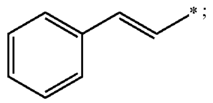 [SMILES: */C=C/c1ccccc1]

(e)

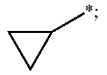

(f)

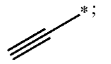

(g)

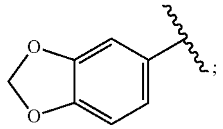 [SMILES: *c1ccc2c(c1)OCO2]

and (h)

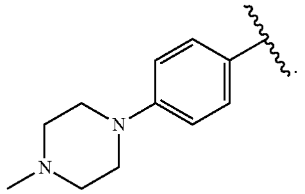

These compounds may preferably be symmetrical.

n (Y, $Y^L$)

In some embodiments, n (in Y or $Y^L$) is an integer between 0 and 24.

In some embodiments, n (in Y or $Y^L$) is an integer between 0 and 12.

In some embodiments, n (in Y or $Y^L$) is an integer between 0 and 8.

In some embodiments, n (in Y or $Y^L$) is an integer between 0 and 6.

In some embodiments, n (in Y or $Y^L$) is 0.

In some embodiments, n (in Y or $Y^L$) is 1.

In some embodiments, n (in Y or $Y^L$) is 2.

In some embodiments, n (in Y or $Y^L$) is 3.

In some embodiments, n (in Y or $Y^L$) is 4.

In some embodiments, n (in Y or $Y^L$) is 5.

In some embodiments, n (in Y or $Y^L$) is 6.

In some embodiments, n (in Y or $Y^L$) is 7.

In some embodiments, n (in Y or $Y^L$) is 8.

In some embodiments, n (in Y or $Y^L$) is 9.

In some embodiments, n (in Y or $Y^L$) is 10.

In some embodiments, n (in Y or $Y^L$) is 11.

In some embodiments, n (in Y or $Y^L$) is 12.

In some embodiments, n (in Y or $Y^L$) is 13.

In some embodiments, n (in Y or $Y^L$) is 14.

In some embodiments, n (in Y or $Y^L$) is 15.

In some embodiments when Y is A1, or $Y^L$ is B1, n may be selected from 3 and 6.

In some embodiments when Y is A2, or $Y^L$ is B2, n may be selected from 4 and 6.

In some embodiments when Y is A3, or $Y^L$ is B3, n may be 4.

In some embodiments when Y is A4, or $Y^L$ is B4, n may be 4.

In some embodiments when Y is A5, or $Y^L$ is B5, n may be 11.

In some embodiments when Y is A6, or $Y^L$ is B6, n may be 2.

L and G

L is a linker connected to the cell binding agent in the conjugate compound. G is a reactive group for connecting the PBD dimer to the cell binding agent to form the conjugate compound.

Preferably, the linker/reactive group contains an electrophilic functional group for reaction with a nucleophilic functional group on the cell binding agent. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii)

active esters such as NHS (N-hydroxysuccinirmide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

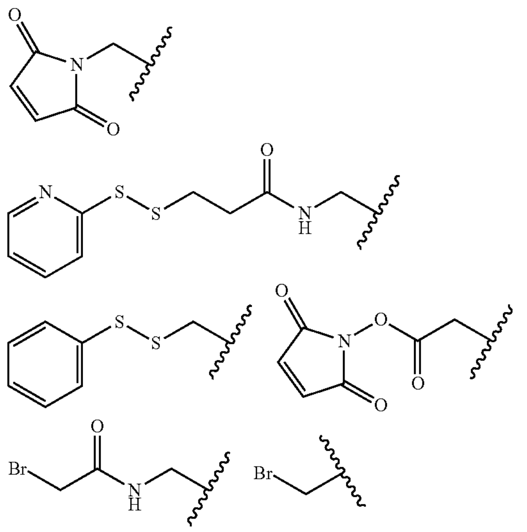

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids. In some embodiments, a Linker has a reactive nucleophilic group which is reactive with an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydroxyl, hydrazine, thiosemicarbazone, hydrazine carboxylate, and arylhydrazide. The electrophilic group on an antibody provides a convenient site for attachment to a Linker.

In one embodiment, the group L is:

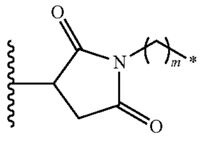

where the asterisk indicates the point of attachment to the rest of group Y, the wavy line indicates the point of attachment to the cell binding agent, and m is an integer selected from the range 0 to 6. In one embodiment, m is selected from 2, 3, 4 and 5.

In one embodiment, the connection between the cell binding agent and L is through a thiol residue of the cell binding agent and a maleimide group of L.

In one embodiment, the connection between the cell binding agent and L is:

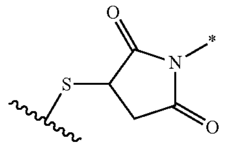 [SMILES: *SC1CC(=O)N(*)C1=O]

where the asterisk indicates the point of attachment to the remaining portion of the L group or the remaining portion of the Y group and the wavy line indicates the point of attachment to the remaining portion of the cell binding agent. In this embodiment, the S atom is typically derived from the cell binding agent.

In each of the embodiments above, an alternative functionality may be used in place of the maleimide-derived group shown below:

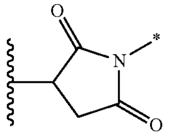 [SMILES: *C1CC(=O)N(*)C1=O]

where the wavy line indicates the point of attachment to the cell binding agent as before, and the asterisk indicates the bond to the remaining portion of the L group or the remaining portion of the Y group.

In one embodiment, the maleimide-derived group is replaced with the group:

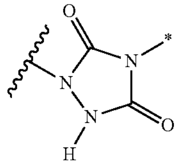 [SMILES: *n1[nH]c(=O)n(*)c1=O]

where the wavy line indicates point of attachment to the cell binding agent, and the asterisk indicates the bond to the remaining portion of the L group or the remaining portion of the Y group.

In one embodiment, the maleimide-derived group is replaced with a group, which optionally together with the cell binding agent, is selected from:

—C(═O)NH—.

—C(═O)O—,

—NHC(═O)—,

—OC(═O)—,

—OC(═O)O—,

—NHC(═O)O—,

—OC(═O)NH—,

—NHC(═O)NH—,

—NHC(═O)NH,

—C(═O)NHC(═O)—,

—S—,

—S—S—,

—$CH_2C(=O)$—

—$C(=O)CH_2$—,

=N—NH—, and

=NH—N=.

In one embodiment, the maleimide-derived group is replaced with a group, which optionally together with the cell binding agent, is selected from:

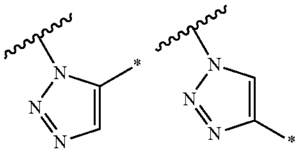 [SMILES: *c1cnnn1* ; *c1cn(*)nn1]

where the wavy line indicates either the point of attachment to the cell binding agent or the bond to the remaining portion of the L group or the remaining portion of the Y group, and the asterisk indicates the other of the point of attachment to the cell binding agent or the bond to the remaining portion of the L group or the remaining portion of the Y group.

Other groups that can be used as L for connecting the remaining portion of the Y group to the cell binding agent are described in WO 20051082023.

Thus, in embodiments of the present invention, L is of formula:

$-L^A-(CH_2)_m-$

Where m is from 0 to 6; and $L^A$ is selected from:

($L^{A1-1}$)

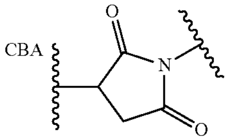

($L^{A1-2}$)

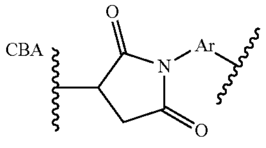

($L^{A2}$)

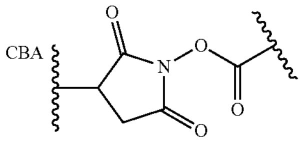

($L^{A3-1}$)

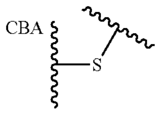

($L^{A3-2}$)

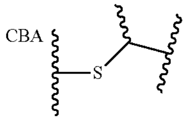

-continued ($L^{A4}$)

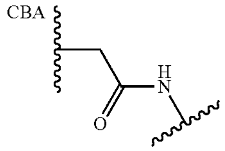

($L^{A5}$)

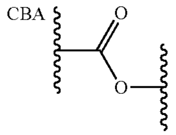

($L^{A6}$)

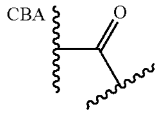

($L^{A7}$)

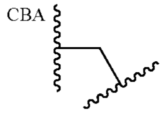

($L^{A8-1}$)

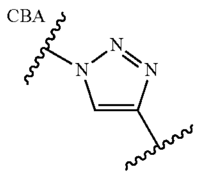

($L^{A8-2}$)

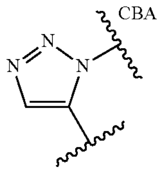

($L^{A9-1}$)

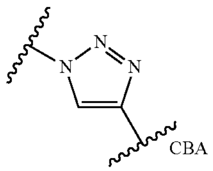

($L^{A9-2}$)

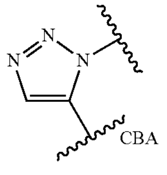

where Ar represents a $C_{5-6}$ arylene group, e.g. phenylene.

In some embodiments where L is L1, m may be 2, 3 or 5.

In some embodiments where L is L1, $L^A$ may be $L^{A1-1}$.

In embodiments of the present invention, L is of formula:

$-L^A-(CH_2)_m-O-$ (L2)

Where m is from 0 to 6; and $L^A$ is selected from the groups above.

Without wishing to be bound by theory, such a group may be cleaved from the antibody such that the carbamate group yields a terminal amine.

In some embodiments where L is L2, $L^A$ may be $L^{A3-2}$.

In some embodiments where L is L2, m may be 1.

In embodiments of the present invention, L is of formula:

$-L^A-(CH_2)_q-O-C(=O)-NH-(CH_2)_p-$ (L3)

Where q is from 1 to 3, and p is from 1 to 3; and
$L^A$ is selected from the groups above.

Without wishing to be bound by theory, such a group may be cleaved from the antibody such that the carbamate group yields the group: $H_2N-(CH_2)_p-$ (L3').

In some embodiments where L is L3, q may be 1, and p may be 2.

In some embodiments where L is L3, $L^A$ may be selected from $L^{A7}$, $L^{A8-1}$ and $L^{A8-2}$.

In embodiments of the present invention, L is of formula:

(L4)

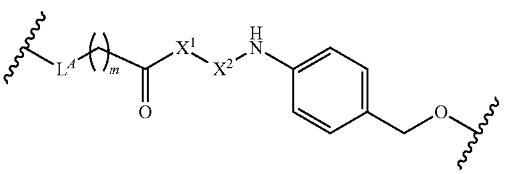

Where m is from 0 to 6;
$X^1$ and $X^2$ are amino acid groups, selected from natural amino acids, which may be modified;
$L^A$ is selected from the groups above.

The natural amino acids may be selected such that the dipeptide group is cathpesin labile.

In one embodiment, the group $-X_1-X_2-$ is selected from:

-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-,
-Trp-Citwhere Cit is citrulline.

Preferably, the group $-X_1-X_2-$ is selected from:

-Phe-Lys-,
-Val-Ala-,
-Val-Lys-,
-Ala-Lys-,
-Val-Cit-.

Most preferably, the group $-X_1-X_2-$ is -Phe-Lys- or -Val-Ala-.

In some embodiments where L is L4, m may be 1.

Other dipeptide combinations may be used, including those described by Dubowchik et al., *Bioconjugate Chemistry,* 2002, 13, 855-869, which is incorporated herein by reference.

In one embodiment, the amino acid side chain is derivatised, where appropriate. For example, an amino group or carboxy group of an amino acid side chain may be derivatised. In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:

Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gin: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl. Z, Z—Br.

Thus, in embodiments of the present invention, G is of formula:

$G^A-(CH_2)_m-$

Where n is from 0 to 6; and
$G^A$ is selected from:

($G^{A1-1}$)

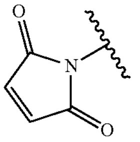

($G^{A1-2}$)

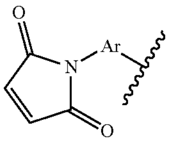

($G^{A2}$)

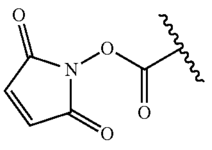

($G^{A3-1}$)

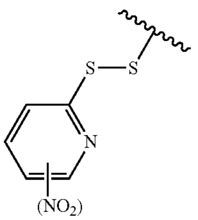

where the $NO_2$ group is optional

-continued ($G^{A3-2}$)

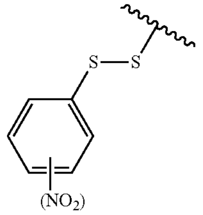

where the $NO_2$ group is optional ($G^{A3-3}$)

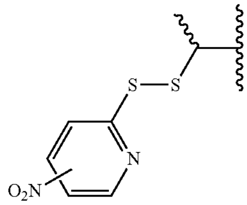

where the $NO_2$ group is optional ($G^{A3-4}$)

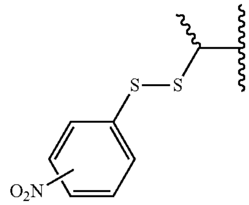

where the $NO_2$ group is optional ($G^{A4}$)

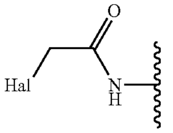

Where Hal = I, Br, Cl ($G^{A5}$)

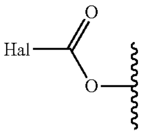

($G^{A6}$)

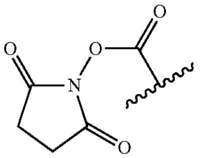

($G^{A7}$)

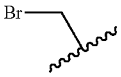

($G^{A8}$)

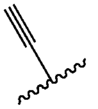

-continued ($G^{A9}$)

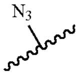

where Ar represents a $C_{5-6}$ arylene group, e.g. phenylene.

In some embodiments where G is G1, m may be 2, 3 or 5.

In some embodiments where G is G1, $G^A$ may be $G^{A1}$.

In embodiments of the present invention, G is of formula:

$$G^A\text{-}(CH_2)_m\text{—O—} \quad (G2)$$

Where m is from 0 to 6; and $G^A$ is selected from the groups above.

In some embodiments where G is G2, $G^A$ may be $G^{A3-2}$.

In some embodiments where G is G2, m may be 1.

In embodiments of the present invention, G is of formula:

$$G^A\text{-}(CH_2)_q\text{—O—C(=O)—NH—}(CH_2)_p\text{—} \quad (L3)$$

Where q is from 1 to 3, and p is from 1 to 3; and $G^A$ is selected from the groups above.

In some embodiments where G is G3, q may be 1, and p may be 2.

In some embodiments where G is G3, $G^A$ may be selected from $G^{A7}$ and $G^{A8}$.

In embodiments of the present invention, G is of formula:

(G4)

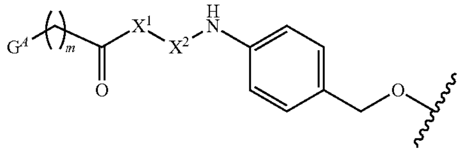

Where m is from 0 to 6;

$X^1$ and $X^2$ are as defined above for L4;

$G^A$ is selected from the groups above.

R and R'

In one embodiment, R is independently selected from optionally substituted $C_{1-12}$ alkyl, $C_{3-20}$ heterocyclyl and $C_{5-20}$ aryl groups. These groups are each defined in the substituents section below.

In one embodiment, R is independently optionally substituted $C_{1-12}$ alkyl.

In one embodiment, R is independently optionally substituted $C_{3-20}$ heterocyclyl.

In one embodiment, R is independently optionally substituted $C_{5-20}$ aryl.

In one embodiment, R is independently optionally substituted $C_{1-12}$ alkyl.

The preferences for R apply also to R'.

In some embodiments of the invention there is provided a compound having a substituent group —NRR'. In one embodiment R and R' together with the nitrogen atom to which they are attached form an optionally substituted 4-, 5-, 6- or 7-membered heterocyclic ring. The ring may contain a further heteroatom, for example N, O or S.

In one embodiment, the heterocyclic ring is itself substituted with a group R. Where a further N heteroatom is present, the substituent may be on the N heteroatom.

$R^{A4}$

In one embodiment, $R^{A4}$ is a $C_{2-4}$ alkylene group.

In one embodiment, $R^{A4}$ is a $C_2$ alkylene group.

In one embodiment, $R^{A4}$ is a $C_3$ alkylene group.

In one embodiment. $R^{A4}$ is an unsubstituted $C_{1-6}$ alkylene group.

In one embodiment, $R^{A4}$ is a linear $C_{1-6}$ alkylene group.

In one embodiment, $R^{A4}$ is selected from the group consisting of $—CH_2H_2—$, $—CH_2CH_2CH_2—$ and $—CH_2CH_2CH_2CH_2—$ Cell Binding Agent A cell binding agent may be of any kind, and include peptides and non-peptides. These can include antibodies or a fragment of an antibody that contains at least one binding site, lymphokines, hormones, growth factors, nutrient-transport molecules, or any other cell binding molecule or substance.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology, 5th Ed.*, Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', $F(ab')_2$, and Fv fragments; diabodies; linear antibodies: fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci.* USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising a VL and VH domains, as well as a light chain constant domain (CL) and heavy chain constant domains, $CH_1$, $CH_2$ and $CH_3$. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

Examples of cell binding agents include those agents described for use in WO 2007/085930, which is incorporated herein.

The cell binding agent may be, or comprise, a polypeptide. The polypeptide may be a cyclic polypeptide. The cell binding agent may be antibody. Thus, in one embodiment, the present invention provides an antibody-drug conjugate (ADC).

Drug Loading

The drug loading is the average number of PBD drugs per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. No. 7,521,541; U.S. Pat. No. 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the drug-linker reagents of the present invention which have thiol-reactive, electrophilic groups such as maleimide or alpha-halo amides to form ADO with cysteine engineered antibodies (ThioMabs) and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved and near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer pyrrolobenzodiazepine groups per cell binding agent.

Peptides

In one embodiment, the cell binding agent is a linear or cyclic peptide comprising 4-20, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC, SEQ ID NO:7. Alternatively, a variant of the A20FMDV-Cys sequence may be used wherein one, two, three, four, five, six, seven, eight, nine or ten amino acid residues is substituted with another amino acid residue.

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', $F(ab')_2$ and Fv fragments.

In these embodiments, each antibody may be linked to one or several dimer pyrrolobenzodiazepine groups. The preferred ratios of pyrrolobenzodiazepine to cell binding agent are given above.

The antibody may be a domain antibody (DAB).

In one embodiment, the antibody is a monoclonal antibody.

Antibodies for use in the present invention include those antibodies described in WO 2005/082023 which is incorporated herein. Particularly preferred are those antibodies for tumour-associated antigens. Examples of those antigens known in the art include, but are not limited to, those tumour-associated antigens set out in WO 2005/082023. See, for instance, pages 41-55.

The conjugates of the invention are designed to target tumour cells via their cell surface antigens. The antigens are usually normal cell surface antigens which are either over-expressed or expressed at abnormal times. Ideally the target antigen is expressed only on proliferative cells (preferably tumour cells), however this is rarely observed in practice. As a result, target antigens are usually selected on the basis of differential expression between proliferative and healthy tissue.

Tumor-associated antigens (TAA) are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203) ten Dijke, P., et al *Science* 264 (5155):101-104 (1994), *Oncogene* 14 (11): 1377-1382 (1997)); WO2004/063362 (Claim 2); WO2003/042661 (Claim 12); US2003/134790-A1 (Page 38-39); WO2002/102235 (Claim 13; Page 296); WO2003/055443 (Page 91-92); WO2002/99122 (Example 2; Page 528-530); WO2003/029421 (Claim 6); WO2003/024392 (Claim 2; FIG. 112); WO2002/98358 (Claim 1; Page 183); WO2002/54940 (Page 100-101); WO2002/59377 (Page 349-350); WO2002/30268 (Claim 27; Page 376); WO2001/48204 (Example; FIG. 4); NP_0.001194 bone morphogenetic protein receptor, type IB/pid=NP_001194.1. Cross-references: MIM:603248; NP_001194.1; AY065994

(2) E16 (LAT1, SLC7A5, Genbank accession no. NM_003486) *Biochem. Biophys. Res. Commun.* 255 (2), 283-288 (1999), *Nature* 395 (6699):288-291 (1998), Gaugitsch, H. W., et al (1992) *J. Biol. Chem.* 267 (16):11267-11273); WO2004/048938 (Example 2); WO2004/032842 (Example IV); WO2003/042661 (Claim 12); WO2003/016475 (Claim 1); WO2002/78524 (Example 2); WO2002/99074 (Claim 19; Page 127-129); WO2002/86443 (Claim 27; Pages 222, 393); WO2003/003906 (Claim 10; Page 293); WO2002/64798 (Claim 33; Page 93-95); WO2000/14228 (Claim 5; Page 133-136); US2003/224454 (FIG. 3); WO2003/025138 (Claim 12; Page 150); NP_003477 solute carrier family 7 (cationic amino acid transporter, y+system), member 5/pid=NP_003477.3-*Homo sapiens*; Cross-references: MIM:600182; NP_003477.3; NM_015923; NM_003486_1

(3) STEAP1 (six transmembrane epithelial antigen of prostate, Genbank accession no. NM_012449); *Cancer Res.* 61 (15), 5857-5860 (2001), Hubert, R. S., et al (1999) *Proc. Natl. Acad. Sci. U.S.A.* 96 (25):14523-14528); WO20041065577 (Claim 6); WO2004/027049 (FIG. 1L); EP1394274 (Example 11); WO2004/016225 (Claim 2); WO2003/042661 (Claim 12); US2003/157089 (Example 5); US2003/185830 (Example 5); US2003/064397 (FIG. 2); WO2002/89747 (Example 5; Page 618-619); WO2003/022995 (Example 9; FIG. 13A, Example 53; Page 173, Example 2; FIG. 2A); NP_036581 six transmembrane epithelial antigen of the prostate; Cross-references: MIM: 604415; NP_036581.1; NM_012449_1

(4) 0772P (CA125, MUC16, Genbank accession no. AF361486); *J. Biol. Chem.* 276 (29):27371-27375 (2001)); WO20041045553 (Claim 14); WO2002/92836 (Claim 6; FIG. 12); WO2002/83866 (Claim 15; Page 116-121); US2003/124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al *Biol. Chem.* 269 (2), 805-808 (1994), *Proc. Natl. Acad. Sci. U.S.A.* 96 (20):11531-11536 (1999), *Proc. Natl. Acad. Sci. U.S.A.* 93 (1):136-140 (1996), *J. Biol. Chem.* 270 (37):21984-21990 (1995)); WO2003/101283 (Claim 14); (WO02002/102235 (Claim 13; Page 287-288); WO2002/101075 (Claim 4; Page 308-309); WO2002/71928 (Page 320-321); WO094/10312 (Page 52-57); Cross-references: MIM:601051; NP_005814.2; NM_005823_1

(6) Napi3b (NAPI-3B, NaPi2B, NPTIIb. SLC34A2, solute carrier family 34 (sodium phosphate), member 2, type 11 sodium-dependent phosphate transporter 3b, Genbank accession no. NM_006424) *J. Biol. Chem.* 277 (22):19665-19672 (2002), *Genomics* 62 (2):281-284 (1999), Feild, J. A., et al (1999) *Biochem. Biophys. Res. Commun.* 258 (3):578-582): WO2004/022778 (Claim 2); EP1394274 (Example 11): WO2002/102235 (Claim 13; Page 326); EP0875569 (Claim 1; Page 17-19); WO02001/57188 (Claim 20; Page 329); WO2004/032842 (Example IV); WO2001/75177 (Claim 24; Page 139-140); Cross-references: MIM:604217; NP_006415.1; NM_006424_1.

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) *DNA Res.* 7 (2):143-150); WO2004/000997 (Claim 1): WO2003/003984 (Claim 1); WO2002/06339 (Claim 1; Page 50); WO2001/88133 (Claim 1; Page 41-43, 48-58); WO2003/054152 (Claim 20); WO2003/101400 (Claim 11); Accession: Q9P283; EMBL; AB040878; BAA95969.1. Genew; HGNC:10737

(8) PSCA hlg (2700050C12Rik, C530008O16Rik, RIKEN cDNA 2700050C12, RIKEN cDNA 2700050C12 gene, Genbank accession no. AY358628); Ross et al (2002) *Cancer Res.* 62:2546-2553; US2003/129192 (Claim 2); US2004/044180 (Claim 12); US2004/044179 (Claim 11); US2003/096961 (Claim 11); US2003/232056 (Example 5); WO2003/105758 (Claim 12); US2003/206918 (Example 5); EP1347046 (Claim 1); WO20031025148 (Claim 20); Cross-references: GI:37182378; AAQ88991.1 AY358628_1

(9) ETBR (Endothelin type B receptor, Genbank accession no. AY275463); Nakamuta M., et at *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, s1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet.* 5:351-354, 1996; Amiel J., et al Hum. Mol. Genet. 5, 355-357, 1996: Hofstra R. M. W., et al *Nat. Genet.* 12, 445-447, 1996; Svensson P. J., et al *Hum. Genet.* 103, 145-148, 1998; Fuchs S., et al *Mol. Med.* 7, 115-124, 2001; Pingault V., et al (2002) *Hum. Genet.* 111, 198-206; WO2004/045516 (Claim 1); WO2004/048938 (Example 2); WO2041040000 (Claim 151); WO20031087768 (Claim 1); WO2003/016475 (Claim 1); WO2003/016475 (Claim 1); WO2002/61087 (FIG. 1); WO20031016494 (FIG. 6); WO2003/025138 (Claim 12; Page 144); WO2001/98351 (Claim 1; Page 124-125); EP0522868 (Claim 8; FIG. 2); WO2001/77172 (Claim 1; Page 297-299); US2003/109676; U.S. Pat. No. 6,518,404 (FIG. 3); U.S. Pat. No. 5,773,223 (Claim 1a; Col 31-34); WO2004/001004 (10) MSG783 (RNF124, hypothetical protein FLJ20315, Genbank accession no. NM_017763); WO2003/104275 (Claim 1); WO02004/046342 (Example 2); WO20031042661 (Claim 12); WO2003/083074 (Claim 14; Page 61); WO2003/018621 (Claim 1); WO2003/024392 (Claim 2; FIG. 93); WO2001/66689 (Example 6); Cross-references: LocusID: 54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO20031087306; US2003/064397 (Claim 1; FIG. 1): WO2002/72596 (Claim 13; Page 54-55); WO2001172962 (Claim 1; FIG. 4B); WO2003/104270 (Claim 11); WO2003/104270 (Claim 16); US2004/005598 (Claim 22); WO2003/042661 (Claim 12); US2003/060612 (Claim 12; FIG. 10); WO2002/26822 (Claim 23; FIG. 2); WO2002/16429 (Claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636); Xu, X. Z., et al *Proc. Natl. Acad. Sci. U.S.A.* 98 (19):10692-10697 (2001), *Cell* 109 (3):397-407 (2002), *J. Biol. Chem.* 278 (33):30813-30820 (2003)); US20031143557 (Claim 4); WO2000/40614 (Claim 14; Page 100-103); WO2002/10382 (Claim 1; FIG. 9A); WO20031042661 (Claim 12); WO02002/30268 (Claim 27; Page 391); US2003/219806 (Claim 4); WO2001/62794 (Claim 14; FIG. 1A-D); Cross-references: MIM: 606936; NP_060106.2; NM_017636_1

(13) CRIPTO (CR, CR1, CRGF, CRIPTO, TDGF1, teratocarcinoma-derived growth factor, Genbank accession no. NP 003203 or NM_003212); Ciccodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (Claim 12); WO2002/88170 (Claim 2; Page 52-53); WO2003/024392 (Claim 2; FIG. 58); WO02002/16413 (Claim 1; Page 94-95, 105); WO2002/22808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004); Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/005538 (Example 1); WO02003/062401 (Claim 9); WO2004/045520 (Example 4); WO91/02536 (FIGS. 9.1-9.9); WO2004/020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674); *Proc. Natl. Acad. Sci. U.S.A.* (2003) 100 (7): 4126-4131, *Blood* (2002) 100 (9):3068-3076, Muller et al (1992) *Eur. J. Immunol.* 22 (6):1621-1625); WO2004/016225 (claim 2, FIG. 140); WO2003/087768, US2004/101874 (claim 1, page 102); WO2003062401 (claim 9); WO2002/78524 (Example 2); US2002/150573 (claim 5, page 15); U.S. Pat. No. 5,644,033; WO2003/048202 (claim 1, pages 306 and 309); WO 99/58658, U.S. Pat. No. 6,534,482 (claim 13, FIG. 17A/B); WO2000/55351 (claim 11, pages 1145-1146); Cross-references: MIM:147245; NP 000617.1; NM 000626_1

(16) FcRH2 (IFGP4, IRTA4, SPAP1A (SH2 domain containing phosphatase anchor protein 1a), SPAP1B, SPAP1C, Genbank accession no. NM_030764, AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu, M. J., et al (2001) *Biochem. Biophys. Res. Commun.* 280 (3):768-775; WO2004/016225 (Claim 2); WO2003/077836; WO2001138490 (Claim 5; FIG. 18D-1-18D-2); WO2003/097803 (Claim 12); WO2003/089624 (Claim 25); Cross-references: MIM:606509; NP_110391.2; NM_030764_1

(17) HER2 (ErbB2, Genbank accession no. M11730); Coussens L., et al *Science* (1985) 230(4730):1132-1139); Yamamoto T., et al *Nature* 319, 230-234, 1986; Semba K., et al *Proc. Natl. Acad. Sci. U.S.A.* 82, 6497-6501, 1985; Swiercz J M., et al *J. Cell Biol.* 165, 869-880, 2004; Kuhns J. J., et al *J. Biol. Chem.* 274, 36422-36427, 1999; Cho H.-S., et al Nature 421, 756-760, 2003; Ehsani A., et al (1993) *Genomics* 15, 426-429; WO2004/048938 (Example 2); WO2004/027049 (FIG. 11); WO2004/009622; WO2003/081210; WO2003/089904 (Claim 9); WO2003/016475 (Claim 1); US2003/118592; WO2003/008537 (Claim 1); WO020031055439 (Claim 29; FIG. 1A-B); WO20031025228 (Claim 37; FIG. 5C); WO02002/22636 (Example 13; Page 95-107); WO2002/12341 (Claim 68; FIG. 7); WO2002/13847 (Page 71-74); WO2002/14503 (Page 114-117); WO02001/53463 (Claim 2; Page 41-46); WO2001/41787 (Page 15); WO2000/44899 (Claim 52; FIG. 7); WO2000/20579 (Claim 3; FIG. 2); U.S. Pat. No. 5,869,445 (Claim 3; Col 31-38); WO9630514 (Claim 2; Page 56-61); EP1439393 (Claim 7); WO2004/043361 (Claim 7); WO2004/022709; WO2001/00244 (Example 3: FIG. 4); Accession: P04626: EMBL; M11767; AAA35808.1.

EMBL; M11761; AAA35808.1. In certain embodiments, conjugate compounds of the invention comprise anti-HER2 antibodies. In one embodiment of the invention, an anti-HER2 antibody of an ADC of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN. In another embodiment of the invention, an anti-HER2 antibody of an ADC of the invention comprises a humanized anti-HER2 antibody, e.g., humanized 2C4, as described in U.S. Pat. No. 7,862,817. An exemplary humanized 2C4 antibody is pertuzumab, commercially available under the tradename PERJETA.

(18) NCA (CEACAM6, Genbank accession no. M18728); Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (Claim 7); WO2004/044178 (Example 4); WO2004/031238; WO2003/042661 (Claim 12); WO2002/78524 (Example 2); WO2002/86443 (Claim 27; Page 427); WO2002/60317 (Claim 2); Accession: P40199; Q14920; EMBL; M29541; AAA59915.1. EMBL; M18728

(19) MDP (DPEP1, Genbank accession no. BC017023); *Proc. Natl. Acad. Sci. U.S.A.* 99 (26):16899-16903 (2002)); WO2003/016475 (Claim 1); WO2002/64798 (Claim 33; Page 85-87); JP05003790 (FIG. 6-8); WO99/46284 (FIG. 9); Cross-references: MIM:179780; AAH17023.1; BC017023_1

(20) IL20Rα (IL20Rα, ZCYTOR7, Genbank accession no. AF184971); Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) *Biochemistry* 42:12617-12624; Sheikh F., et al (2004) *J. Immuno.* 172, 2006-2010; EP1394274 (Example 11); US2004/005320 (Example 5); WO02003/029262 (Page 74-75); WO2003/002717 (Claim 2; Page 63); WO2002/22153 (Page 45-47); US2002/042366 (Page 20-21); WO2001146261 (Page 57-59); WO2001/46232 (Page 63-65); WO98/37193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053); Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003/186372 (Claim 11); US2003/186373 (Claim 11); US2003/119131 (Claim 1; FIG. 52); US2003/119122 (Claim 1; FIG. 52); US2003/119126 (Claim 1); US2003/119121 (Claim 1; FIG. 52); US2003/119129 (Claim 1); US2003/119130 (Claim 1); US2003/119128 (Claim 1; FIG. 52); US2003/119125 (Claim 1); WO2003/016475 (Claim 1); WO2002/02634 (Claim 1)

(22) EphB2R (DRT, ERK, Hek5, EPHT3, Tyro5, Genbank accession no. NM_004442); Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)): WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328); US2004/0101899 (Claim 2); WO2003104399 (Claim 11); WO2004000221 (FIG. 3); US2003/165504 (Claim 1); US2003/124140 (Example 2); US2003/065143 (FIG. 60); WO2002/102235 (Claim 13; Page 299); US2003/091580 (Example 2); WO2002110187 (Claim 6; FIG. 10); WO2001/94641 (Claim 12; FIG. 7b); WO2002/02624 (Claim 13; FIG. 1A-1B); US2002/034749 (Claim 54; Page 45-46); WO2002/06317 (Example 2; Page 320-321, Claim 34; Page 321-322); WO02002/71928 (Page 468-469); WO2002/02587 (Example 1; FIG. 1); WO2001/40269 (Example 3; Pages 190-192); WO2000136107 (Example 2; Page 205-207); WO2004/053079 (Claim 12); WO2003/004989 (Claim 1); WO2002/71928 (Page 233-234, 452-453); WO 01/16318

(24) PSCA (Prostate stem cell antigen precursor, Genbank accession no. AJ297436); Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004/022709; EP1394274 (Example 11); US2004/018553 (Claim 17); WO2003/008537 (Claim 1); WO02002181646 (Claim 1; Page 164); WO2003/003906 (Claim 10; Page 288); WO2001/40309 (Example 1; FIG. 17); US20011/055751 (Example 1; FIG. 1b); WO2000/32752 (Claim 18; FIG. 1); WO98/51805 (Claim 17; Page 97); WO98/51824 (Claim 10; Page 94); WO98/40403 (Claim 2; FIG. 1B); Accession: 043653; EMBL; AF043498; AAC39607.1

(25) GEDA (Genbank accession No. AY260763); AAP14954 lipoma HMGIC fusion-partner-like protein ipid=AAP14954.1-*Homo sapiens* (human); WO2003/054152 (Claim 20); WO2003/000842 (Claim 1); WO2003/023013 (Example 3, Claim 20); US20031194704 (Claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1-*Homo sapiens*: Thompson, J. S., et al *Science* 293 (5537), 2108-2111 (2001); WO2004/058309; WO02004/011611; WO2003/045422 (Example: Page 32-33); WO2003/014294 (Claim 35; FIG. 6B); WO2003/035846 (Claim 70; Page 615-616); WO2002/94852 (Col 136-137); WO2002/38766 (Claim 3; Page 133); WO2002/24909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) *J. Exp. Med.* 173:137-146; WO2003/072036 (Claim 1; FIG. 1); Cross-references: MIM:107266; NP_001762.1; NM_001771_1.

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pl: 4.84, MW: 25028 TM: 2 [P] Gene Chromosome: 19q13.2, Genbank accession No. NP 001774.10); WO2003/088808, US2003/0228319; WO2003/062401 (claim 9); US2002/150573 (claim 4, pages 13-14); WO99/58658 (claim 13, FIG. 16); WO92/07574 (FIG. 1); U.S. Pat. No. 5,644,033; Ha et al (1992) *J. Immunol.* 148(5):1526-1531; Müller et al (1992) *Eur. J. Immunol.* 22:1621-1625; Hashimoto et al (1994) *Immunogenetics* 40(4):287-295: Preud'homme eat al (1992) *Clin. Exp. Immunol.* 90(1):141-146; Yu et al (1992) *J. Immunol.* 148 (2) 633-637; Sakaguchi et al (1988) *EMBO J.* 7(11):3457-3464

(29) CXCR5 (Burkitt's lymphoma receptor 1, a CG protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pl: 8.54 MW: 41959 TM: 7 [P] Gene Chromosome: 11q23.3, Genbank accession No. NP 0.001707.1); WO2004/040000; WO2004/015426; US2003/105292 (Example 2); U.S. Pat. No. 6,555,339 (Example 2); WO200261087 (FIG. 1); WO2001157188 (Claim 20, page 269); WO2001/72830 (pages 12-13); WO2000/22129 (Example 1, pages 152-153, Example 2, pages 254-256); WO99/28468 (claim 1, page 38); U.S. Pat. No. 5,440,021 (Example 2, col 49-52): WO094/28931 (pages 56-58): WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta subunit of MHC class II molecule (Ia antigen) that binds peptides and presents them to CD4+T lymphocytes); 273 aa. pl: 6.56, MW: 30820.TM: 1 [P] Gene Chromosome: 6p21.3, Genbank accession No. NP_002111.1); Tonnelle et al (1985) *EMBO J.* 4(11):2839-2847; Jonsson et al (1989) *Immunogenetics* 29(6):411-413; Beck et al (1992) *J. Mo. Biol.* 228:433-441; Strausberg et al (2002) *Proc. Natl. Acad. Sci USA* 99:16899-16903; Servenius et al (1987) *J. Biol. Chem.* 262:8759-8766; Beck et al (1996) *J. Mol. Biol.* 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) *Immunogenetics* 30(1):66-68; Larhammar et al (1985) *J. Biol. Chem.* 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pl: 7.63, MW: 47206 TM: 1 [P] Gene Chromosome: 17p13.3, Genbank accession No. NP_002552.2); Le et al (1997) *FEBS Lett.* 418(1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO02003/029277 (page 82)

(32) CD72 (B-cell differentiation antigen CD72, Lyb-2); 359 aa, pl: 8.66, MW: 40225, TM: 1 [P] Gene Chromosome: 9p13.3, Genbank accession No. NP_001773.1); WO2004042346 (claim 65); WO2003/026493 (pages 51-52, 57-58); WO2000/75655 (pages 105-106); Von Hoegen et al (1990) J. Immunol. 144(12):4870-4877; Strausberg et al (2002) *Proc. Natl. Acad. Sci USA* 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pl: 6.20, MW: 74147 TM: 1 [P] Gene Chromosome: 5q12, Genbank accession No. NP_005573.1); US2002/193567; WO97/07198 (claim 11, pages 39-42); Miura at al (1996) *Genomics* 38(3):299-304; Miura et al (1998) *Blood* 92:2815-2822; WO2003/083047; WO97/44452 (claim 8, pages 57-61); WO2000112130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa, pl: 5.28, MW: 46925 TM: 1 [P] Gene Chromosome: 1q21-1q22, Genbank accession No. NP_443170.1); WO2003/077836; WO2001/38490 (claim 6, FIG. 18E-1-18-E-2); Davis et al (2001) *Proc. Natl. Acad. Sci USA* 98(17):9772-9777; WO02003/089624 (claim 8); EP1347046 (claim 1); WO2003/089624 (claim 7)

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pl: 6.88, MW: 106468, TM: 1 [P] Gene Chromosome: 1q21, Genbank accession No. Human: AF343662, AF343663, AF343664, AF343665, AF369794, AF397453. AK090423, AK090475, AL834187, AY358085; Mouse:AK089756, AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004/074320; JP2004113151; WO2003/042661; WO2003/009814; EP1295944 (pages 69-70); WO2002130268 (page 329); WO2001190304: US2004/249130; US2004/022727; WO2004/063355; US2004/197325; US2003/232350; US2004/005563; US2003/124579; Horie et al (2000) *Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J Cancer. October* 15; 94(2):178-84.

(37) CD33 (CD33 molecule, SIGLEC-3, SIGLEC3, p67; CD33 antigen (gp67); gp67; myeloid cell surface antigen CD33; sialic acid binding Ig-like lectin 3; sialic acid-binding Ig-like lectin); Nucleotide: Genbank accession no. M_23197; Genbank version no. NM_23197.1 GI:180097; Genbank record update date: Jun. 23, 2010 08:47 AM: Polypeptide: Genbank accession no. AAA51948; Genbank version no. AAA51948.1 GI:188098; Genbank record update date: Jun. 23, 2010 08:47 AM; Simmons D., et al *J. Immunol.* 141 (8), 2797-2800 (1988); Antibodies: H195 (Lintuzumab)-Raza A., et al *Leuk Lymphoma.* 2009 August; 50(8):1336-44; U.S. Pat. No. 6,759,045 (Seattle Genetics/Immunomedics): mAb OKT9: Sutherland, D. R. et al. *Proc Natl. Acad Sci USA* 78(7): 4515-4519 1981, Schneider, C., et al *J Biol Chem* 257, 8516-8522 (1982); mAb E6: Hoogenboom, H. R., et al *J Immunol* 144, 3211-3217 (1990); U.S. Pat. No. 6,590,088 (Human Genome Sciences)—for example, SEQ ID NOs: 1 and 2 and ATCC accession no. 97521; U.S. Pat. No. 7,557,189 (Immunogen)—for example, an antibody or fragment thereof comprising a heavy chain variable region which comprises three CDRs having the amino acid sequences of SEQ ID NOs:1-3 and a light chain variable region comprising three CDRs having the amino acid sequences of SEQ ID NOs:4-6.

(38) LGR5/GPR49; Nucleotide: Genbank accession no. NM_003667; Genbank version no. NM_003667.2 GI:24475886; Genbank record update date: Jul. 22, 2012 03:38 PM; Polypeptide: Genbank accession no. NP 003658; Genbank version no. NP_003658.1 GI:4504379; Genbank record update date: Jul. 22, 2012 03:38 PM.

The parent antibody may also be a fusion protein comprising an albumin-binding peptide (ABP) sequence (Dennis et al. (2002) "Albumin Binding As A General Strategy For Improving The Pharmacokinetics Of Proteins" *J Biol Chem.* 277:35035-35043; WO 01/45746). Antibodies of the invention include fusion proteins with ABP sequences taught by:

(i) Dennis et al (2002) *J Biol Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumour related antigen $\alpha_v\beta_6$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

In a preferred embodiment, the substituents described herein (which include optional substituents) are limited to those groups that are not reactive to a cell binding agent. The link to the cell binding agent in the present case is formed from the bridge between the two PBD moieties through a linker group to the cell binding agent. Reactive functional groups located at other parts of the PBD structure may be capable of forming additional bonds to the cell binding agent (this may be referred to as crosslinking). These additional bonds may alter transport and biological activity of the conjugate. Therefore, in some embodiment, the additional substituents are limited to those lacking reactive functionality.

In one embodiment, the substituents are selected from the group consisting of R, OR, SR, NRR', $NO_2$, halo, $CO_2R$, COR, $CONH_2$, CONHR, and CONRR'.

In one embodiment, the substituents are selected from the group consisting of R, OR, SR, NRR', $NO_2$, $CO_2R$, COR, $CONH_2$, CONHR, and CONRR'.

In one embodiment, the substituents are selected from the group consisting of R, OR, SR, NRR', $NO_2$, and halo.

In one embodiment, the substituents are selected from the group consisting of R, OR, SR, NRR', and $NO_2$.

Any one of the embodiment mentioned above may be applied to any one of the substituents described herein. Alternatively, the substituents may be selected from one or more of the groups listed below.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

An alkyl group may optionally be interrupted by one or more heteroatoms selected from O, N(H) and S. Such groups may be referred to as "heteroalkyl".

$C_{2-12}$ Heteroalkyl: The term "$C_{2-12}$ heteroalkyl" as used herein, pertains to a monovalent moiety obtained by removing a hydrogen atom from a carbon atom of a hydrocarbon compound having from 2 to 12 carbon atoms, and one or more heteroatoms selected from O, N(H) and S, preferably O and S.

Examples of heteroalkyl groups include, but are not limited to those comprising one or more ethylene glycol units of the type $-(OCH_2CH_2)-$. The terminal of a heteroalkyl group may be the primary form of a heteroatom, e.g. $-OH$, $-SH$ or $-NH_2$. In a preferred embodiment, the terminal is $-CH_3$.

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, $-CH{=}CH_2$), 1-propenyl ($-CH{=}CH-CH_3$), 2-propenyl (allyl, $-CH-CH{=}CH_2$), isopropenyl (1-methylvinyl, $-C(CH_3){=}CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl ($-C{\equiv}CH$) and 2-propynyl (propargyl, $-CH_2-C{\equiv}CH$).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:

cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_5$), methylcyclopentane ($C_6$), dimethylcyclopentane ($C_7$) and methylcyclohexane ($C_7$);

unsaturated monocyclic hydrocarbon compounds:

cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:

norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$); $O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{16}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$) acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$):

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromrene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —OH(OH)(OEt).

Ketal: —CR($OR^1$)($OR^2$), where $R^1$ and $R^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group.

Examples ketal groups include, but are not limited to, —C(Me)$(OMe)_2$, —C(Me)$(OEt)_2$, —C(Me)(OMe)(OEt), —C(Et)$(OMe)_2$, —C(Et)$(OEt)_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): ═O.

Thione (thioketone): ═S.

Imino (imine): ═NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, ═NH, ═NMe, ═NEt, and ═NPh.

Formyl (carbaldehyde, carboxaldehyde): —C(═O)H.

Acyl (keto): —C(═O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$alkyl group. Examples of acyl groups include, but are not limited to, —C(═O)$CH_3$ (acetyl), —C(═O)$CH_2CH_3$ (propionyl), —C(═O)C$(CH_3)_3$ (t-butyryl), and —C(═O)Ph (benzoyl, phenone).

Carboxy (carboxylic acid): —C(═O)OH.

Thiocarboxy (thiocarboxylic acid): —C(═S)SH.

Thiolocarboxy (thiolocarboxylic acid): —C(═O)SH.

Thionocarboxy (thionocarboxylic acid): —C(═S)OH.

Imidic acid: —C(═NH)OH.

Hydroxamic acid: —C(═NOH)OH.

Ester (carboxylate, carboxylic acid ester, oxycarbonyl): —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(═O)$OCH_3$, —C(═O)$OCH_2CH_3$, —C(═O)OC$(CH_3)_3$, and —C(═O)OPh.

Acyloxy (reverse ester): —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(═O)$CH_3$ (acetoxy), —OC(═O)$CH_2CH_3$, —OC(═O)C$(CH_3)_3$, —OC(═O)Ph, and —OC(═O)$CH_2$Ph.

Oxycarboyloxy: —OC(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group.

Examples of ester groups include, but are not limited to, —OC(═O)$OCH_3$, —OC(═O)$OCH_2CH_3$, —OC(═O)OC$(CH_3)_3$, and —OC(═O)OPh.

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —NHC$(CH_3)_2$, —N$(CH_3)_2$, —N$(CH_2CH_3)_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(═O)$NR^1R^2$, wherein $R^1$ and $R^2$ are independently amino substituents, as defined for amino groups. Examples of amido groups include, but are not limited to, —C(═O)$NH_2$, —C(═O)$NHCH_3$, —C(═O)N$(CH_3)_2$, —C(═O)$NHCH_2CH_3$, and —C(═O)N$(CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(═S)$NR^1R^2$, wherein $R^1$ and $R^2$ are independently amino substituents, as defined for amino groups. Examples of amido groups include, but are not limited to, —C(═S)$NH_2$, —C(═S)$NHCH_3$, —C(═S)N$(CH_3)_2$, and —C(═S)$NHCH_2CH_3$.

Acylamido (acylamino): —$NR^1$C(═O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and $R^2$ is an acyl substituent, for example, a $C_{1-7}$ alkyl group, a $C_{3-20}$ heterocyclyl group, or a $C_{5-2}$aryl group, preferably hydrogen or a $C_{1-7}$alkyl group. Examples of acylamide groups include, but are not limited to, —NHC(═O)$CH_3$, —NHC(═O)$CH_2CH_3$, and —NHC(═O)Ph. $R^1$ and $R^2$ may together form a cyclic structure, as in, for example, succinimidyl, maleimidyl, and phthalimidyl:

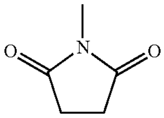

succinimidyl

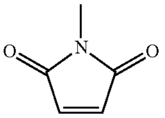

maleimidyl

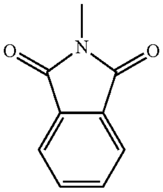

phthalimidyl

Aminocarbonyloxy: —OC(═O)$NR^1R^2$, wherein $R^1$ and $R^2$ are independently amino substituents, as defined for amino groups. Examples of aminocarbonyloxy groups include, but are not limited to, —OC(═O)$NH_2$, —OC(═O)NHMe, —OC(═O)$NMe_2$, and —OC(═O)$NEt_2$.

Ureido: —N(R')CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —$NHCONH_2$, —NHCONHMe, —NHCONHEt, —$NHCONMe_2$, —$NHCONEt_2$, —$NMeCONH_2$, —NMeCONHMe, —NMeCONHEt, —$NMeCONMe_2$, and —$NMeCONEt_2$.

Guanidino: —NH—C(═NH)$NH_2$.

Tetrazolyl: a five membered aromatic ring having four nitrogen atoms and one carbon atom,

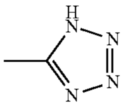

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine (amidino): —C(=NR)$NR_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$alkyl group. Examples of amidine groups include, but are not limited to, —C(=NH)$NH_2$, —C(=NH)$NMe_2$, and —C(=NMe)$NMe_2$.

Nitro: —$NO_2$.

Nitroso: —NO.

Azido: —$N_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —$SCH_3$ and —$SCH_2CH_3$.

Disulfide: —SS—R, wherein R is a disulfide substituent, for example, a $C_{1-7}$alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —$SSCH_3$ and —$SSCH_2CH_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)$CH_3$ and —S(=O)$CH_2CH_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2CH_3$ (methanesulfonyl, mesyl), —S(=O)$_2CF_3$ (triflyl), —S(=O)$_2CH_2CH_3$ (esyl), —S(=O)$_2C_4F_9$ (nonaflyl), —S(=O)$_2CH_2CF_3$ (tresyl), —S(=O)$_2CH_2CH_2NH_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —$SO_2H$.

Sulfonic acid (sulfo): —S(=O)$_2$OH, —$SO_3H$.

Sulfinate (sulfinic acid ester): —S(=O)OR; wherein R is a sulfinate substituent, for example, a $C_{1-7}$alkyl group, a $C_{3-20}$ heterocyclyl group, or a $C_{5-20}$ aryl group, preferably a $C_{1-7}$ alkyl group. Examples of sulfinate groups include, but are not limited to, —S(=O)$OCH_3$ (methoxysulfinyl; methyl sulfinate) and —S(=O)$OCH_2CH_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2OCH_3$ (methoxysulfonyl; methyl sulfonate) and —S(=O)$_2OCH_2CH_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)$CH_3$ and —OS(=O)$CH_2CH_3$CH.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2CH_3$ (mesylate) and —OS(=O)$_2$ $CH_2CH_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2OCH_3$ and —SO(=O)$_2OCH_2CH_3$.

Sulfamyl (sulfamoyl; sulfinic acid amide: sulfinamide): —S(=O)$NR^1R^2$, wherein $R^1$ and $R^2$ are independently amino substituents, as defined for amino groups. Examples of sulfamyl groups include, but are not limited to, —S(=O)$NH_2$, —S(=O)NH($CH_3$), —S(=O)N($CH_3$)$_2$, —S(=O)NH($CH_2CH_3$), —S(=O)N($CH_2CH_3$)$_2$, and —S(=O)NHPh.

Sulfonamido (sulfinamoyl; sulfonic acid amide; sulfonamide): —S(=O)$_2NR^1R^2$, wherein $R^1$ and $R^2$ are independently amino substituents, as defined for amino groups. Examples of sulfonamido groups include, but are not limited to, —S(=O)$_2NH_2$, —S(=O)$_2$NH($CH_3$), —S(=O)$_2$N($CH_3$)$_2$, —S(=O)$_2$NH($CH_2CH_3$), —S(=O)$_2$N($CH_2CH_3$)$_2$, and —S(=O)$_2$NHPh.

Sulfamino: —$NR^1$S(=O)$_2$OH, wherein $R^1$ is an amino substituent, as defined for amino groups. Examples of sulfamino groups include, but are not limited to, —NHS(=O)$_2$ OH and —N($CH_3$)S(=O)$_2$OH.

Sulfonamino: —$NR^1$S(=O)$_2$R, wherein $R^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2CH_3$ and —N($CH_3$)S(=O)$_2$ $C_6H_5$.

Sulfinamino: —$NR^1$S(=O)R, wherein $R^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)$CH_3$ and —N($CH_3$)S(=O)$C_6H_5$.

Phosphino (phosphine): —$PR_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —$PH_2$, —P($CH_3$)$_2$, —P($CH_2CH_3$)$_2$, —P(t-Bu)$_2$, and —P(Ph)$_2$.

Phospho: —P(=O)$_2$.

Phosphinyl (phosphine oxide): —P(=O)$R_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$aryl group. Examples of phosphinyl groups include, but are not limited to, —P(=O)($CH_3$)$_2$, —P(=O)($CH_2CH_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)$(OCH_3)_2$, —P(=O)$(OCH_2CH_3)_2$, —P(=O)$(O\text{-t-Bu})_2$, and —P(=O)$(OPh)_2$.

Phosphoric acid (phosphonooxy): —OP(=O)$(OH)_2$.

Phosphate (phosphonooxy ester): —OP(=O)$(OR)_2$, where R is a phosphate substituent, for example, —H, a $C_{1-7}$, alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)$(OCH_3)_2$, —OP(=O)$(O_2C2CH_3)_2$, —OP(=O)$(O\text{-t-Bu})_2$, and —OP(=O)$(OPh)_2$.

Phosphorous acid: —$OP(OH)_2$.

Phosphite: —$OP(OR)_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —$OP(OCH_3)_2$, —OP $(OCH_2CH_3)_2$, —$OP(O\text{-t-Bu})_2$, and —$OP(OPh)_2$.

Phosphoramidite: —$OP(OR^1)$—$NR^2_2$, where $R^1$ and $R^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$; alkyl group, or a $C_{5-20}$ aryl group. Examples of phosphoramidite groups include, but are not limited to, —$OP(OCH_2CH_3)$—$N(CH_3)_2$, —$OP(OCH_2CH_3)$—$N(i\text{-Pr})_2$, and —OP $(OCH_2CH_2CN)$—$N(i\text{-Pr})_2$.

Phosphoramidate: —OP(=O)$(OR^1)$—$NR^{22}$, where $R^1$ and $R^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $CO_{1-7}$ alkyl group, or a $C_{5-20}$ aryl group. Examples of phosphoramidate groups include, but are not limited to, —OP(=O) $(OCH_2CH_3)$—$N(CH_3)_2$. —OP(=O)$(OCH_2CH_3)$ —$N(i\text{-Pr})_2$, and —OP(=O)$(OCH_2CH_2CN)$—$N(i\text{-Pr})_2$.

Alkylene $C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated $C_{3-12}$ alkylene groups include, but are not limited to, —$(CH_2)_n$— where n is an integer from 3 to 12, for example, —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH$—$_2CH_2CH_2CH_2$— (heptylene).

Examples of branched saturated $C_{3-12}$ alkylene groups include, but are not limited to, —$CH(CH_3)CH_2$—, —CH $(CH_3)CH_2CH_2$—, —$CH(CH_3)CH_2CH_2CH_2$—, —$CH_2CH$ $(CH_3)CH_2$—, —$CH_2CH(CH_3)CH_2CH_2$—, —CH $(CH_2CH_3)$—, —$CH(CH_2CH_3)CH_2$—, and —$CH_2CH$ $(CH_2CH_3)CH_2$—.

Examples of linear partially unsaturated $C_{3-12}$ alkylene groups ($C_{3-12}$ alkenylene, and alkynylene groups) include, but are not limited to, —CH=CH—$CH_2$—, —$CH_2$—CH=$CH_2$—, —CH=CH—$CH_2$—$CH_2$—, —CH=CH—$CH_2$—CH—$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, —CH=CH—$CH_2$—$CH_2$—CH=CH—, and —$CH_2$—C≡C—$CH_2$—.

Examples of branched partially unsaturated $C_{3-12}$ alkylene groups ($C_{3-12}$ alkenylene and alkynylene groups) include, but are not limited to, —$C(CH_3)$=CH—, —$C(CH_3)$=CH—$CH_2$—, —CH=CH—$CH(CH_3)$— and —C≡C—$CH(CH_3)$—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Includes Other Forms

Unless otherwise specified, included in the above are the well known ionic, salt, solvate, and protected forms of these substituents. For example, a reference to carboxylic acid (—COOH) also includes the anionic (carboxylate) form (—$COO^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—$O^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.,* 66, 1-19 (1977).

For example, if the compound is anionic, or has a functional group which may be anionic (e.g. —COOH may be —$COO^-$), then a salt may be formed with a suitable cation. Examples of suitable inorganic cations include, but are not limited to, alkali metal ions such as $Na^+$ and $K^+$; alkaline earth cations such as $Ca^{2+}$ and $Mg^{2+}$, and other cations such as $Al^{+3}$. Examples of suitable organic cations include, but are not limited to, ammonium ion (i.e. $NH_4^+$) and substituted ammonium ions (e.g. $NH_3R^+$; $NH_2R_2^+$; $NHR_3^+$; $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD moiety, which is illustrated below where the solvent is water or an alcohol ($R^AOH$, where $R^A$ is $C_{1-4}$ alkyl):

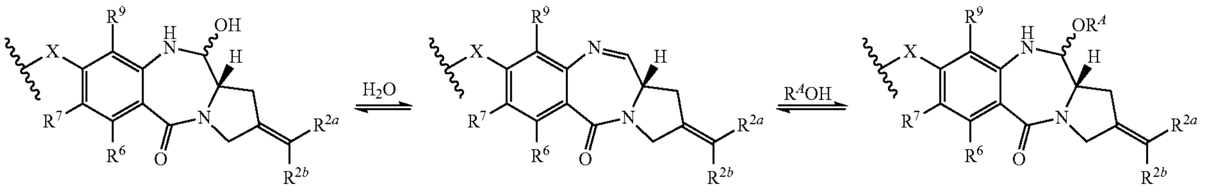

These forms can be called the carbinolamine and carbinolamine ether forms of the PBD (as described in the section relating to $R^{10}$ above). The balance of these equilibria depend on the conditions in which the compounds are found, as well as the nature of the moiety itself.

These particular compounds may be isolated in solid form, for example, by lyophilisation.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, $—OCH_3$, is not to be construed as a reference to its structural isomer, a hydroxymethyl group, $—CH_2OH$. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

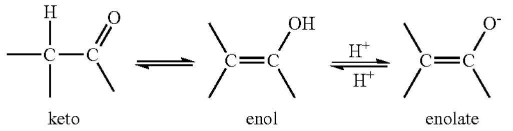

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^{1}H$, $^{2}H$ (D), and $^{3}H$ (T); C may be in any isotopic form, including $^{12}C$, $^{13}C$, and $^{14}C$; O may be in any isotopic form, including $^{16}O$ and $^{18}O$; and the like.

Examples of isotopes that can be incorporated into compounds of the invention include isotopes of hydrogen, carbon, nitrogen, oxygen, phosphorous, fluorine, and chlorine, such as, but not limited to $^{2}H$ (deuterium, D), $^{3}H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of an ADC of the invention.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of *Coleoptera* luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, re-suspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 μl per well) into black 96 well plates. Plates of adherent cell lines are incubated overnight to allow adherence. Suspension cell cultures can be used on the day of seeding.

A stock solution (1 ml) of ADC (20 μg/ml) is made in the appropriate cell culture medium. Serial 10-fold dilutions of stock ADC are made in 15 ml centrifuge tubes by serially transferring 100 μl to 900 μl of cell culture medium.

Four replicate wells of each ADC dilution (100 μl) are dispensed in 96-well black plates, previously plated with cell suspension (100 μl), resulting in a final volume of 200 μl. Control wells receive cell culture medium (100 μl).

If the doubling time of the cell line is greater than 30 hours, ADC incubation is for 5 days, otherwise a four day incubation is done.

At the end of the incubation period, cell viability is assessed with the Alamar blue assay. AlamarBlue (Invitrogen) is dispensed over the whole plate (20 μl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

In Vivo Efficacy

The in vivo efficacy of antibody-drug conjugates (ADC) of the invention can be measured by tumor xenograft studies in mice. For example, the in vivo efficacy of an anti-HER2 ADC of the invention can be measured by a high expressing HER2 transgenic explant mouse model. An allograft is propagated from the Fo5 mmtv transgenic mouse which does not respond to, or responds poorly to, HERCEPTIN® therapy. Subjects were treated once with ADC at certain dose levels (mg/kg) and PBD drug exposure ($\mu g/m^2$); and placebo buffer control (Vehicle) and monitored over two weeks or more to measure the time to tumor doubling, log cell kill, and tumor shrinkage.

Use

The conjugates of the invention may be used to provide a PBD conjugate at a target location.

The target location is preferably a proliferative cell population. The antibody is an antibody for an antigen present in a proliferative cell population.

In one embodiment the antigen is absent or present at a reduced level in a non-proliferative cell population compared to the amount of antigen present in the proliferative cell population, for example a tumour cell population.

The target location may be in vitro, in vivo or ex vivo.

The antibody-drug conjugate (ADC) compounds of the invention include those with utility for anticancer activity. In particular, the compounds include an antibody conjugated, i.e. covalently attached by a linker, to a PBD moiety.

At the target location the linker may not be cleaved. The antibody-drug conjugate (ADC compounds of the invention may have a cytotoxic effect without the cleavage of the linker to release a PBD drug moiety. The antibody-drug conjugates (ADC) of the invention selectively deliver cytotoxic agent to tumor tissue whereby greater selectivity, i.e. a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

In one embodiment, the treatment is of a pancreatic cancer.

In one embodiment, the treatment is of a tumour having $\alpha_v\beta_6$ integrin on the surface of the cell.

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present invention may be used in a method of therapy. Also provided is a method of treatment, comprising administering to a subject in need of treatment a therapeutically-effective amount of a conjugate compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITI NIB®, SU11248, Pfizer), letrozole (FEMARA®, Novartis), imatinib mesylate (GLEEVEC, Novartis), XL-518 (Mek inhibitor, Exelixis, WO 2007/044515), ARRY-886 (Mek inhibitor, AZD6244, Array BioPharma, Astra Zeneca). SF-1126 (PI3K inhibitor, Semafore Pharmaceuticals), BEZ-235 (PI3K inhibitor, Novartis), XL-147 (PI3K inhibitor, Exelixis), PTK7871ZK 222584 (Novartis), fulvestrant (FASLODEX®, AstraZeneca), leucovorin (folinic acid), rapamycin (sirolimus, RAPAMUNE®, Wyeth), lapatinib (TYKERB®. GSK572016, Glaxo Smith Kline), Ionafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, II), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, Iomustine, nimustine, and ranimnustine; antibiotics such as the enediyne antibiotics (e.g. calicheamicin, calicheamicin gamma1I, calicheamicin omegaI1 (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamhine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gerntuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present invention, and for use in accordance with the present invention, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Remington's Pharmaceutical Sciences,*

20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Antibody Drug Conjugates

Antibody drug conjugates may be prepared by several routes, employing organic chemistry reactions, conditions, and reagents known to those skilled in the art, including: (1) reaction of a nucleophilic group of an antibody with a bivalent linker reagent, to form antibody-linker intermediate Ab-L, via a covalent bond, followed by reaction with an activated drug moiety reagent; and (2) reaction of a drug moiety reagent with a linker reagent, to form drug-linker reagent D-L, via a covalent bond, followed by reaction with the nucleophilic of an antibody. Conjugation methods (1) and (2) may be employed with a variety of antibodies, and linkers to prepare the antibody-drug conjugates of the invention.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present invention. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a fetus. In one preferred embodiment, the subject/patient is a human.

In one embodiment, the patient is a population where each patient has a tumour having $\alpha_v\beta_6$ integrin on the surface of the cell.

Synthesis

One possible synthesis route to a dimer intermediate of formula IV is shown below:

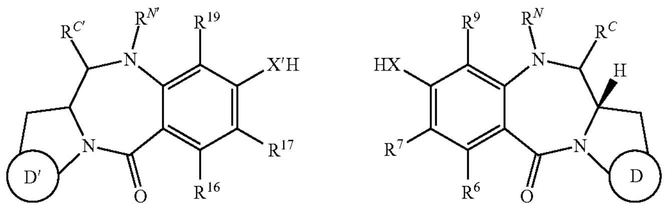

I + II

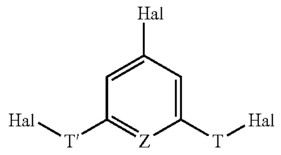

III

-continued
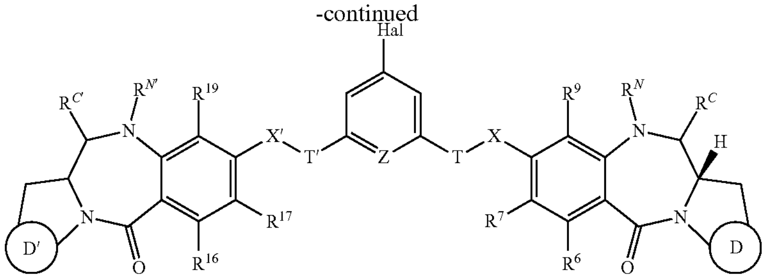
IV
Intermediate IV can be used to make intermediate VII
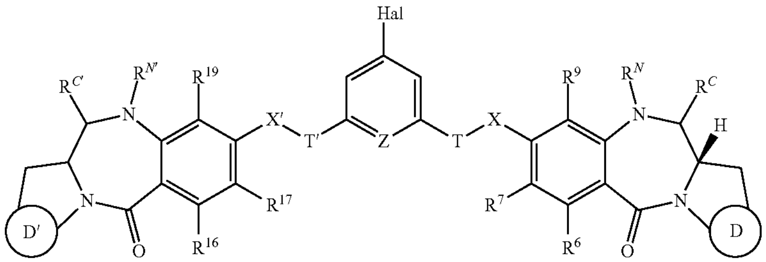
IV
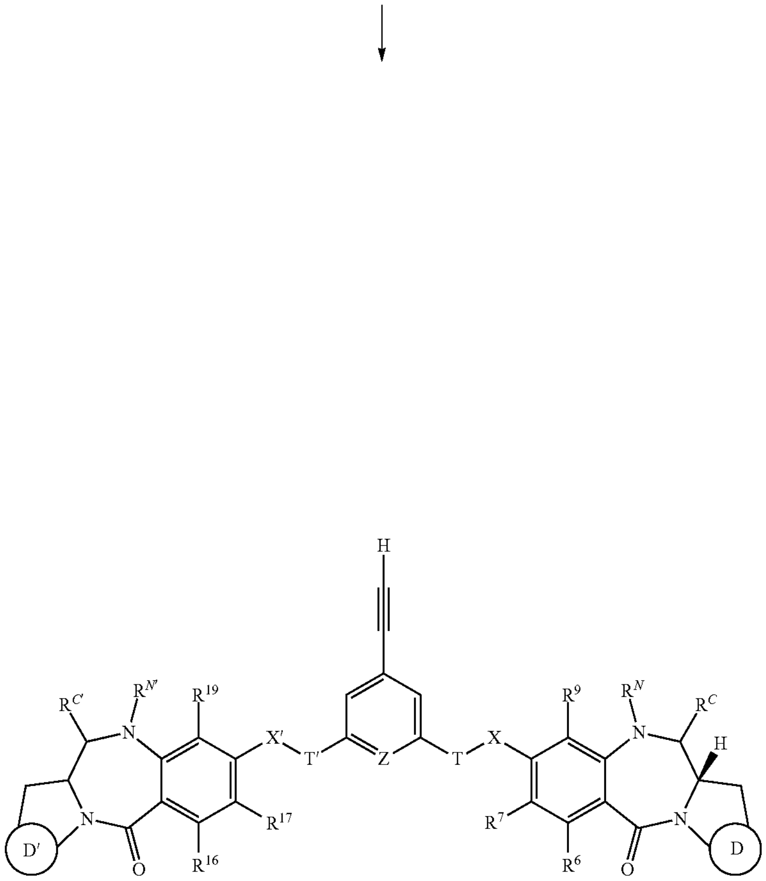
V -continued
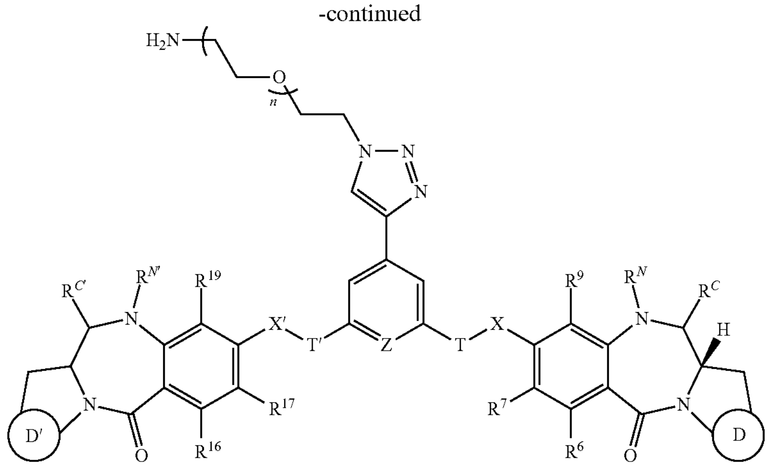
VI
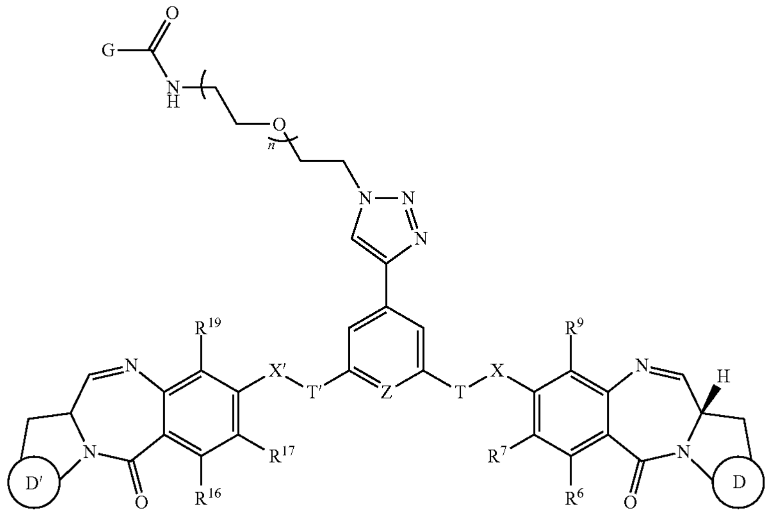
VII
Intermediate IV can be used to make intermediate IX:
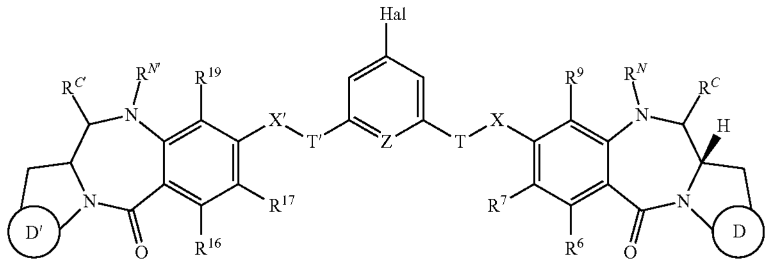
IV -continued
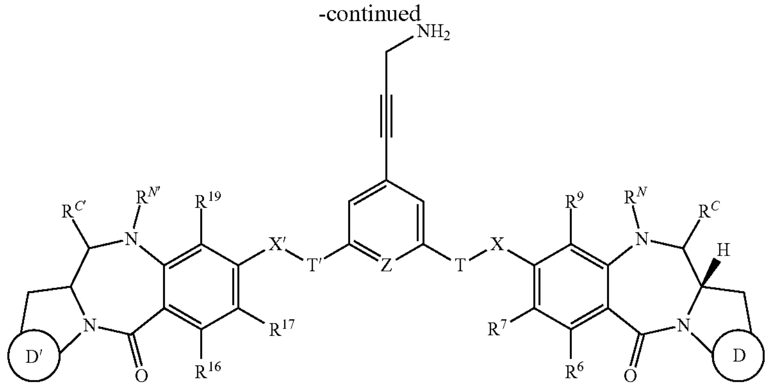
VIII
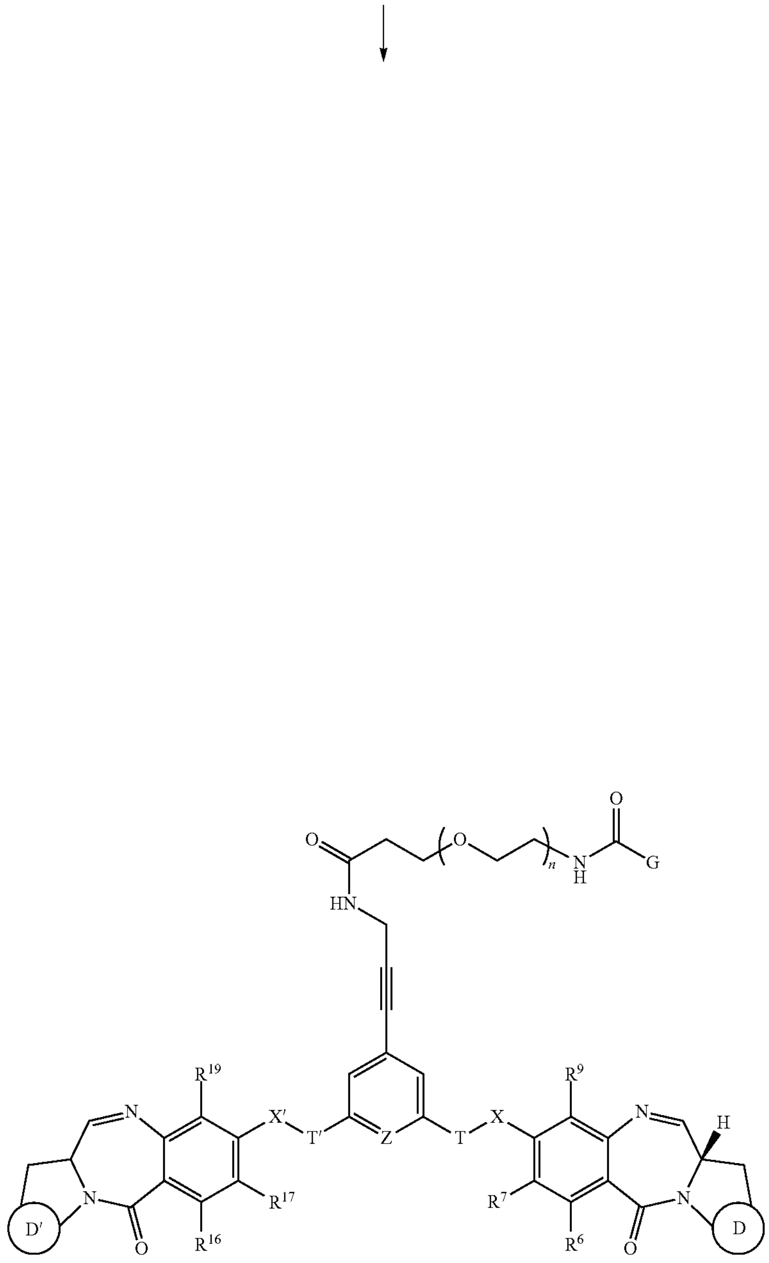
IX Alternatively, intermediate IV can be coupled with intermediate X to make intermediate IX:
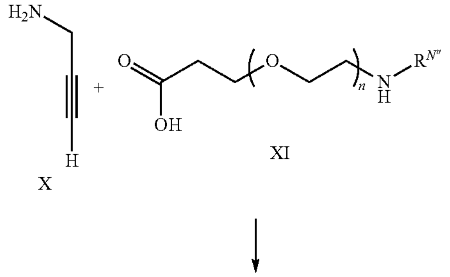
X XI
-continued
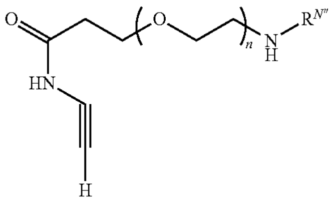
XII
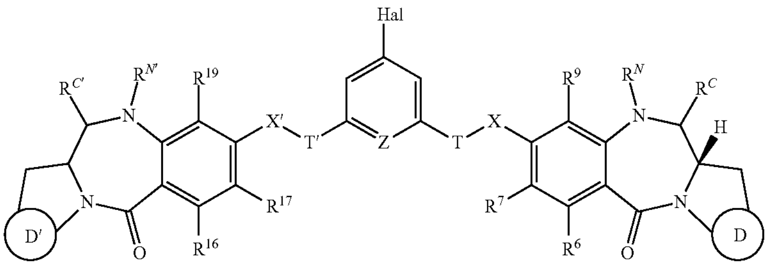
IV
+ XII
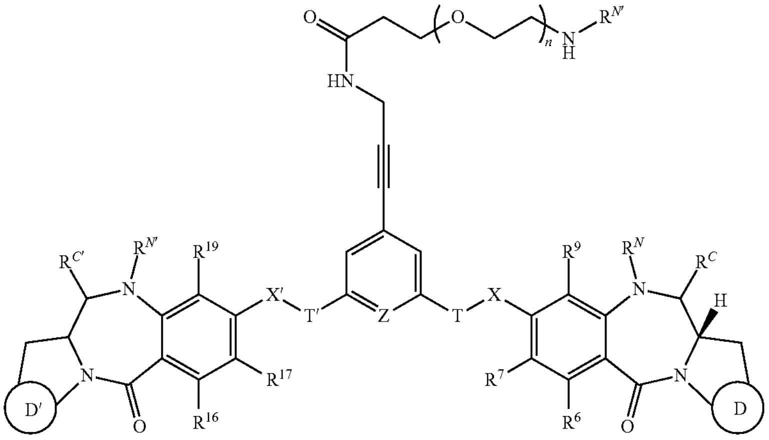
XIII
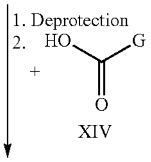
XIV -continued
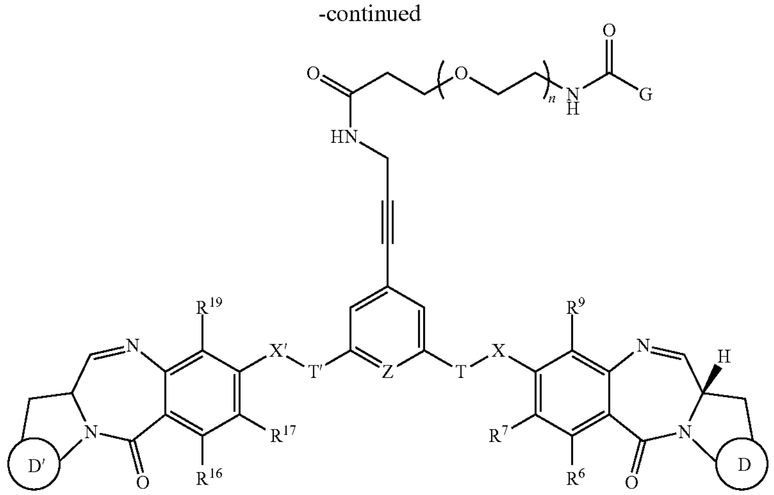
IX
Intermediate IV can be used to make intermediate XVI
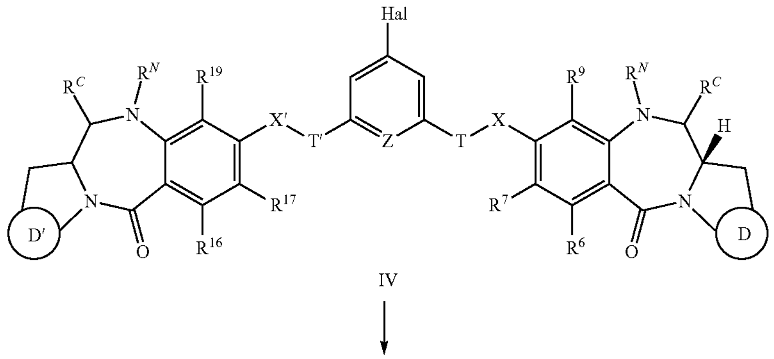
IV
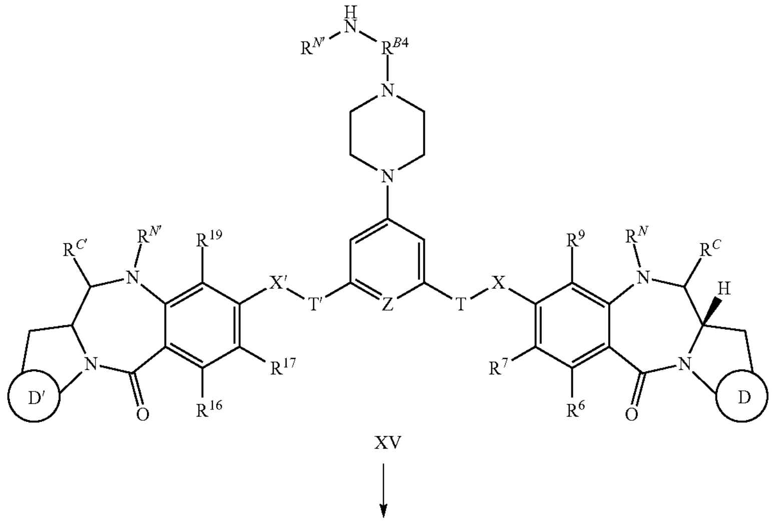
XV -continued
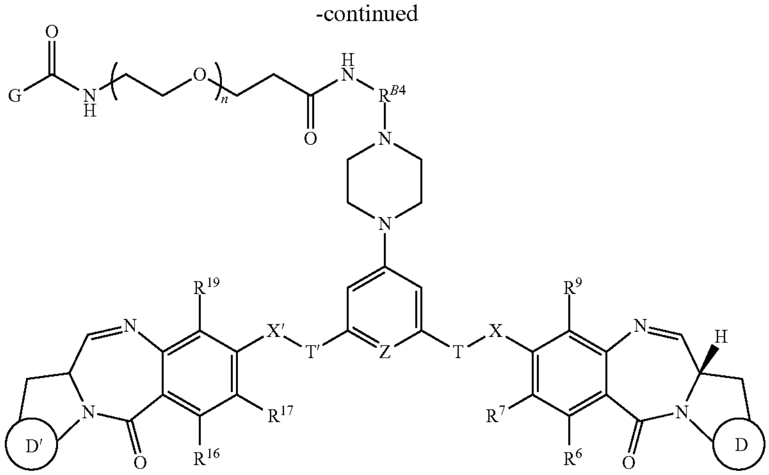
XVI
Intermediate IV can be used to make intermediate XIX
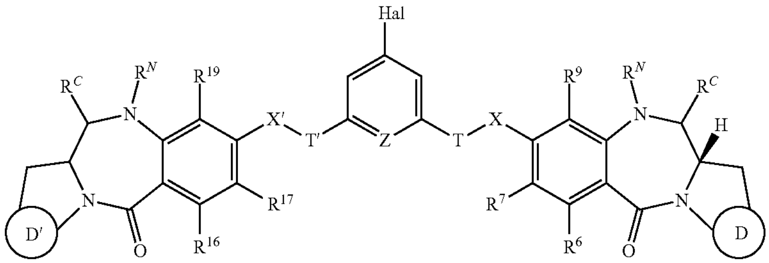
IV
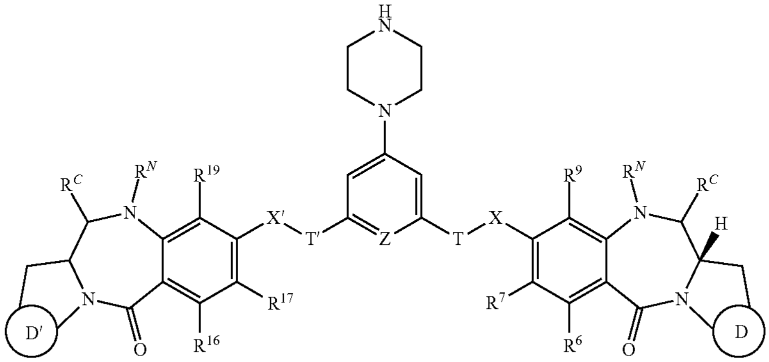
XVII
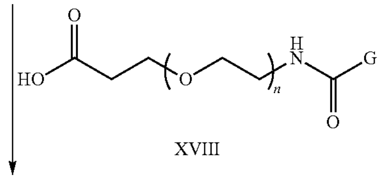
XVIII -continued
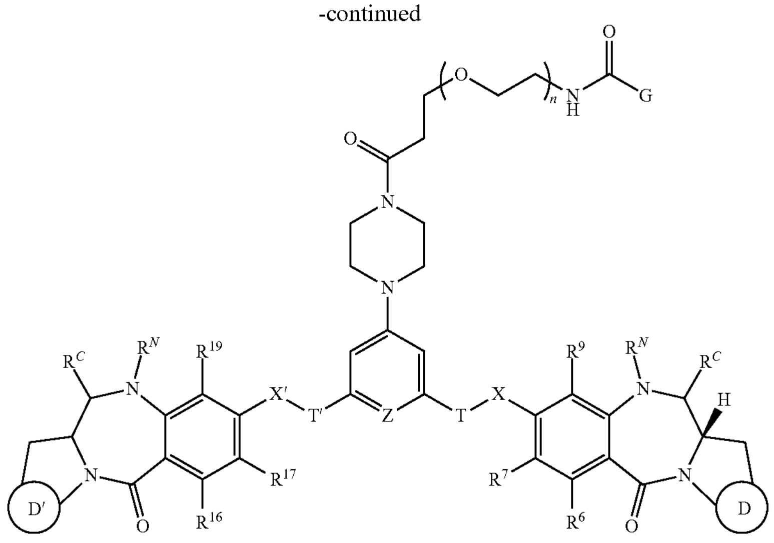
XIX
One possible synthesis route to a dimer intermediate of formula XIV is shown below:
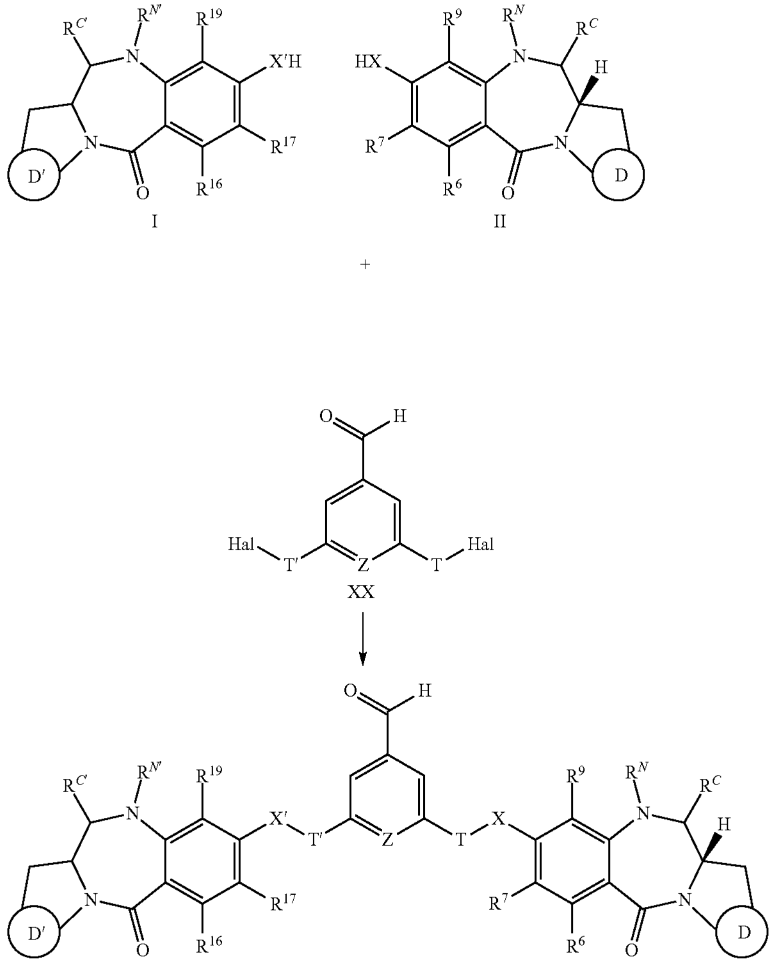
XXI -continued
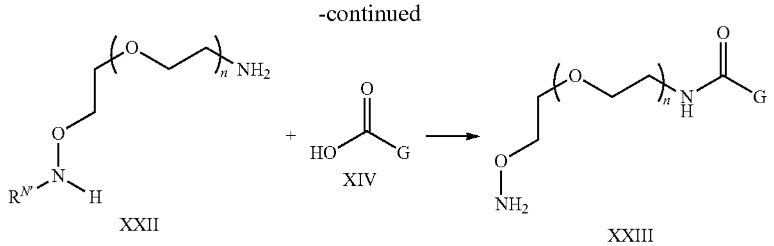
XXII XIV XXIII
XXI + XXIII →
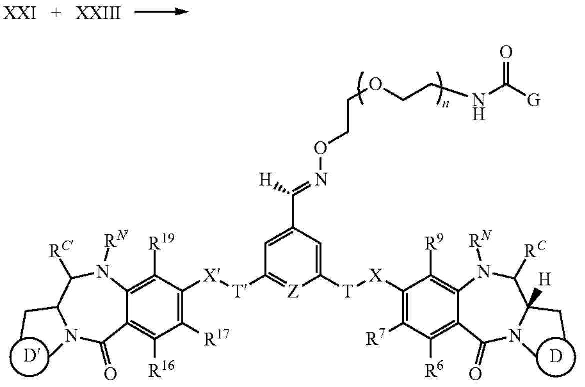
XXIV
Intermediate XXI can be Used to make intermediate XXVII:
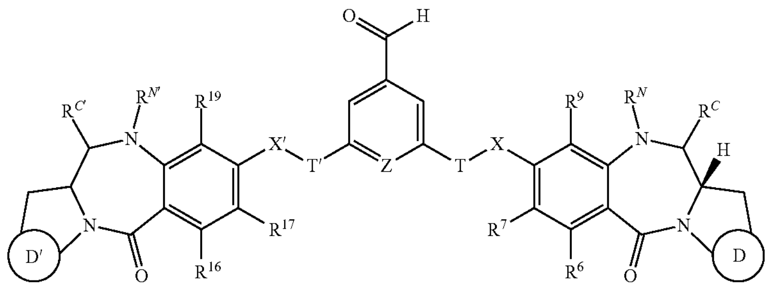
XXI
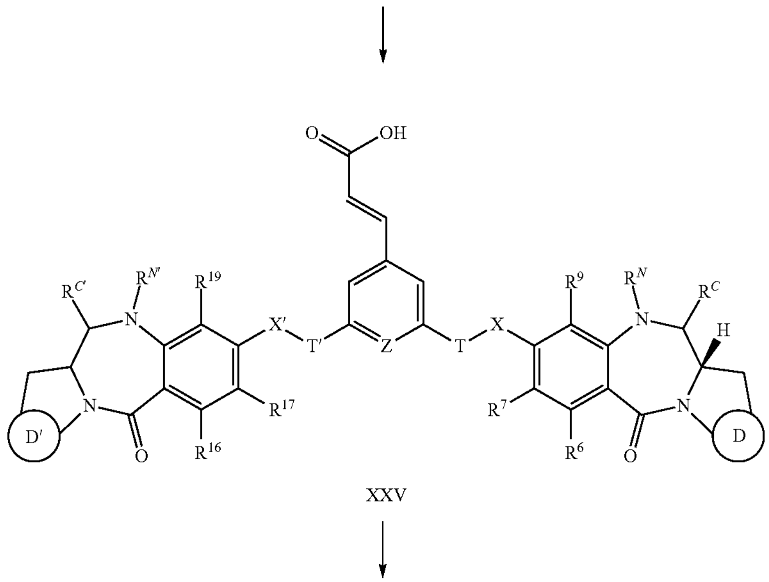
XXV -continued

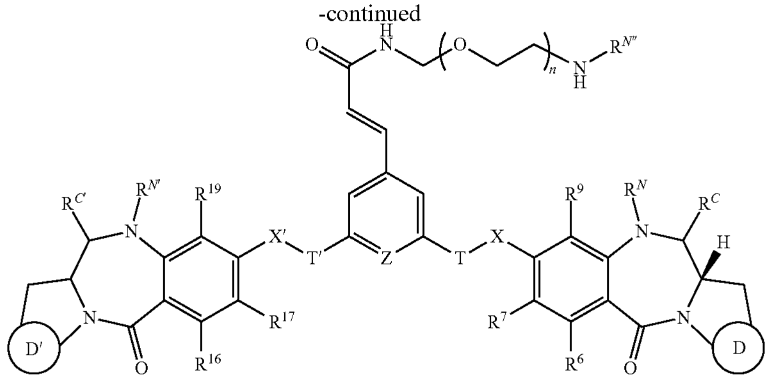

XXVI

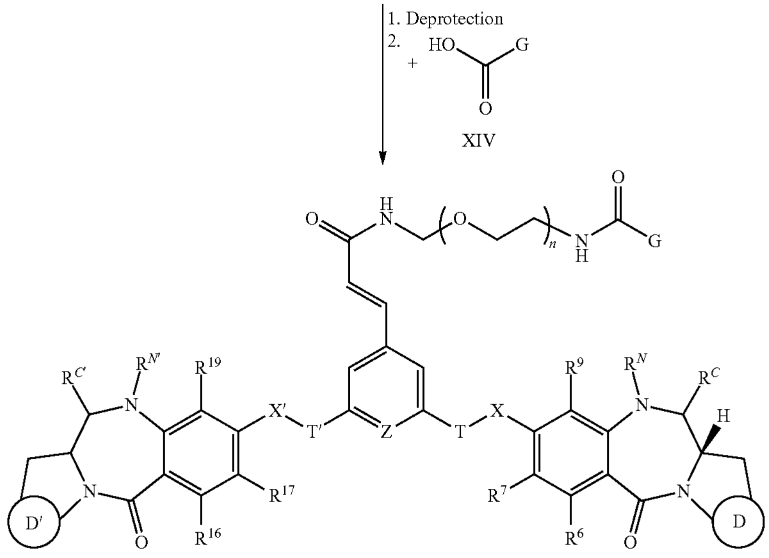

XXVII

In the above schemes, $R^N$, $R^{N'}$, and $R^{N''}$ each independently represent a nitrogen protecting group. $R^C$ and $R^{C'}$ each independently represent OH or $OProt^O$, where $Prot^O$ is a hydroxy protecting group. Protecting groups are well known in the art. $R^N$, $R^{N'}$ and $R^{N''}$ may be, for example, BOG. $Prot^O$ may be THP. It may be the protection of the N10-C11 imine bonds is removed at a different stage in the synthesis methods to that shown above, dependent on the chemistries employed.

In general, the compounds and conjugates can be prepared by first linking two PBD monomers with a phenylene or pyridylene dimer bridge to produce intermediate IV or XXI. The halogen group on the aryl ring in the dimer bridge of intermediate IV may then be used to form the tether (including linker group G or L) to connect the PBD dimer to the cell binding agent.

In more detail, two PBD monomers with —XH and —X'H groups at the C8 position of each PBD monomer (intermediates I and II, respectively) may be rected with -T-Hal and -T'-Hal groups on intermediate II or intermediate XX. Such a method of synthesis allows for the PBD monomers to be different and so the resulting PBD dimer is asymmetrical. Equally, the PBD monomers may be the same.

PBD dimer intermediate IV may be used to provide the compounds and conjugates of the present invention by reacting the aryl halogen group in the bridge in a number of ways.

First, intermediate IV can be used in a Sonogishira cross-coupling reaction to provide an acetylene group on the aryl group of the dimer bridge. Sonogishira cross-coupling reactions are well known in the art for coupling a terminal alkyne with an aryl halide in the presence of a palladium catalyst, such as $Pd(Ph_3)_4$, a copper catalyst, such as CuI, and a base, such as diethylamine.

When acetylene is to be used as the terminal acetylene, one side of the acetylene molecule is typically protected with, for example, TMS in order to prevent cross-linking of the PBD dimers. Once the Sonogishira reaction is complete, the TMS group can be cleaved to provide alkyne intermediate V.

Intermediate V can be reacted with an azido compound to form a triazole derivative in an azide-alkyne Huisgen cycloaddition. Such a reaction may be catalysed by a copper catalyst. To form the compounds and conjugates of the present invention, the azide is bonded to an ethylene group and a variable number of PEG groups. The azide may be terminated with an amine group to react further. Reaction of intermediate V with an amino-azide compound will provide intermediate VI.

The free amine group of intermediate VI can then be reacted with a carboxylic acid group of a linker group for connecting to a cell binding unit to form the amido group linking the PBD dimer to the linker group G or L to provide compound VII.

The linker group/reactive group, G, of intermediate VII can be conjugated to a cell binding agent to provide conjugates of the present invention.

As an alternative Sonogishira reaction, intermediate IV can be coupled to an acetylamine, such as propargylamine in the presence of palladium and copper catalysts and base. Such a reaction provides part of a tether attached to the PBD dimer bridge where the aclyne group is preserved and a free terminal amine is available for further reaction. For example, the reaction of intermediate IV with propargylamine provides intermediate VIII.

The terminal amine of intermediate VIII can be reacted with, for example, a carboxylic acid group attached to a linker/reactive group G (for connecting to a cell binding agent) to provide intermediate IX.

As an alternative synthesis of intermediate IX, the carboxylic acid group of intermediate XI can be reacted with propargylamine to form intermediate XII. Reaction of intermediate IV with intermediate XII in a Sonogoshira reaction yields intermediate XIII.

The protected amine group terminated the variable PEG chain can be deprotected and reacted with the carboxylic acid group of intermediate XIV in order to couple the linker/reactive group G onto the PBD dimer and produce intermediate XIV.

Intermediate IV may also used in a cross-coupling amination reaction, such as a Buchwald-Hartwig amination. A carbon-nitrogen bond is formed via a palladium-catalysed cross-coupling of an amine with an aryl halide. A number of palladium catalysts for use in such cross-coupling reactions are known, such as $Pd(Ph_3)_4$ or RuPhos/RuPhosPd.

Reaction of intermediate IV with a piperizine functionalised with a protected propan-1-amine provides intermediate XV. The protected amine of intermediate XV can be further reacted with, for example, a carboxylic acid group attached to a linker/reactive group, G, for connecting to a cell binding agent to provide intermediate XVI.

Cross-coupling amination reaction, such as a Buchwald-Hartwig amination, of intermediate IV with a partially protected piperazine followed by deprotection (for example with trifluoroacetic acid) provides intermediate XVII.

The deprotected piperazine amine group of intermediate XVII can be reacted with a carboxylic acid group in intermediate XVIII to provide intermediate XIX.

Intermediate XXI can be used to form the oxime intermediate XXIV. For example, a partially protected PEG-diamine, intermediate XXII, may be reacted with the carboxylic acid group of intermediate XIV. Deprotection yields intermediate XIII.

Reaction of intermediates XXI and XXIII yields oxime intermediate XXIV. The syn and anti oximes can be resolved using preparative HPLC.

Intermediate XXI can also be used to form the acrylamide intermediate XXVII. For example, the aldehyde intermediate XXI can be reacted with malonic acid in a Knoevenagel condensation to yield the acrylic acid intermediate XXV. This can be reacted with a partially protected PEG-diamine to yield intermediate XXVI. Deprotectopm and coupling with intermediate XIV yield the acrylamide intermediate XXVII The synthesis of PBD compounds containing two imine moieties is extensively discussed in the following references, which discussions are incorporated herein by reference:

a) WO 00/12508 (pages 14 to 30);
b) WO 2005/023814 (pages 3 to 10);
c) WO 2005/085259 (pages 31 to 39)
d) WO 2011/128650 (pages 2 to 12 and 42 to 51);
e) PCT/EP2012/070232, filed 12 Oct. 2012 (pages 2 to 15 and 49 to 58).

EXAMPLES

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1H$ and $^{13}C$ NMR spectra were acquired at 300 K using a Bruker Avance NMR spectrometer at 400 and 100 MHz, respectively. Chemical shifts are reported relative to TMS (δ=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM. All chemicals and solvents were purchased from Sigma-Aldrich and were used as supplied without further purification.

LC/MS conditions—Method A: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm.

LC/MS conditions—Method B: The HPLC (Waters Alliance 2695) was run using a mobile phase of water (A) (formic acid 0.1%) and acetonitrile (B) (formic acid 0.1%). Gradient: initial composition 5% B held over 1.0 min, then increase from 5% B to 95% B over a 2.5 min period. The composition was held for 0.5 min at 95% B, then returned to 5% B in 0.1 minutes and hold there for 0.9 min. Total gradient run time equals 5 min. Flow rate 3.0 mL/min, 400 μL was split via a zero dead volume tee piece which passes into the mass spectrometer. Wavelength detection range: 220 to 400 nm. Function type: diode array (535 scans). Column: Phenomenex Onyx Monolithic C18 50×4.60 mm.

LC/MS conditions—Method C: Positive mode electrospray mass spectrometry was performed using a Shimadzu Nexera®/Prominence® LCMS-2020. Mobile phases used were solvent A ($H_2O$ with 0.1% formic acid) and solvent B ($CH_3CN$ with 0.1% formic acid). Gradient: Initial composition 5% B held over 0.25 min, then increased from 5% B to 100% B over a 2 min period. The composition was held for 0.50 min at 100% B, then returned to 5% B in 0.05 min and held there for 0.05 min. The total duration of the gradient run was 3.0 min. Flow rate was 0.8 mL/min. Detection was at 214 and 254 nm. Column: Waters Acquity UPLC® BEH Shield RP18 1.7 μm 2.1×50 mm at 50° C.

The preparative HPLC conditions for Examples 2 and 3 were as follows: Reverse-phase ultra-fast high-performance liquid chromatography (UFLC) was carried out on a Shimadzu Prominence® machine using Phenomenex® Gemini NX 5μ C18 columns (at 50° C.) of the following dimensions: 150×4.6 mm for analysis, and 150×21.2 mm for preparative work. Eluents used were solvent A ($H_2O$ with 0.1% formic acid) and solvent B ($CH_3CN$ with 0.1% formic acid). All UFLC experiments were performed with gradient conditions: From 0 to 30 min the composition of B was increased from 0 to 100% and held at 100% B for a further 2 min. The composition of B was decreased from 100% to 0% from 32.0 min to 32.1 min and held at 0% B until 35.0 min. The total duration of the gradient run was 35.0 min. Flow rates used were 1.0 mL/min for analytical, and 20.0 mL/min for preparative HPLC. Detection was at 254 and 280 nm.

LCMS conditions—Method D: Shimazu LCMS-2020, using a mobile phase of water (A) (formic acid 0.1%) and acetonitrile (B) (formic acid 0.1%). Gradient: initial composition 5% B held over 0.25 min, then increase from 5% B to 100% B over a 2 min period. The composition was held for 0.50 min at 100% B, then returned to 5% B in 0.05 minutes and hold there for 0.05 min. Total gradient run time equals 3 min. Flow rate 0.8 mL/min. Wavelength detection range: 190 to 800 nm. Oven temperature: 50° C. Column: Kinetex 2.6u XB-C18 100A 50×2.10 mm.

LC/MS conditions—Method E: Shimazu LCMS-2020, using a mobile phase of water (A) (formic acid 0.1%) and acetonitrile (B) (formic acid 0.1%). Gradient: initial composition 5% B held over 1 min, then increase from 5% B to 100% B over a 9 min period. The composition was held for 2 min at 100% B, then returned to 5% B in 0.10 minutes and hold there for 3 min. Total gradient run time equals 15 min. Flow rate 0.6 mL/min. Wavelength detection range: 190 to 800 nm. Oven temperature: 50° C. Column: Gemini-NX 3u C18 110A 100×2.00 mm.

Synthesis of Intermediates tert-butyl (15-oxo-3,6,9,12-tetraoxa-16-azanonadec-18-yn-1-yl) carbamate (13)

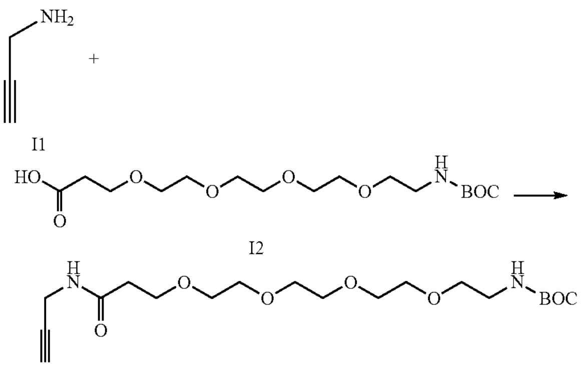

I1

I2

I3

EDCI (263 mg, 1.37 mmol, 1 eq) was added to a solution of propargylamine (88 μL, 1.37 mmol, 1 eq) and t-boc-N-amido-dPEG®$_4$-acid (365.42 mmol, 1.37 mmol, 1 eq) in dichloromethane (10 mL). The reaction was stirred at room temperature for 3 hours after which full conversion was observed by TLC. The reaction mixture was diluted in dichloromethane and washed with water and brine. The organic layer was dried over magnesium sulphate, filtered and excess dichloromethane was removed by rotary evaporation under reduced pressure. The resulting residue was subjected to flash column chromatography (silica gel; gradient, 0% to 10% methanol in dichloromethane). Pure fractions were collected and combined and excess eluent was removed by rotary evaporation under reduced pressure to give the product I3 (490 mg, 89%). $^1$H NMR (400 MHz, $CDCl_3$) δ 6.90 (s, 1H), 5.06 (d, J=23.2 Hz, 1H), 4.03 (dd, J=5.3, 2.5 Hz, 2H), 3.72 (t, J=5.7 Hz, 2H), 3.69-3.57 (m, 12H), 3.53 (t, J=5.1 Hz, 2H), 3.30 (d. J=5.0 Hz, 2H), 2.49 (t, J=5.7 Hz, 2H), 2.20 (t, J=2.5 Hz, 1H), 1.43 (s, 9H).

Example 1

(a) (11S,11aS,11'S,11a'S)-di-tert-butyl 8,8'-(((5-halo-1,3-phenylene)bis(methylene))bis(oxy))bis(7-methoxy-5-oxo-1-((tetrahydro-2H-pyran-2-yl)oxy)-2,3,11,11a-tetrahydro-1H pyrrolo[2,1-c][1,4] benzodiazepine-10(5H)-carboxylate) (2a, 2b, 2c)

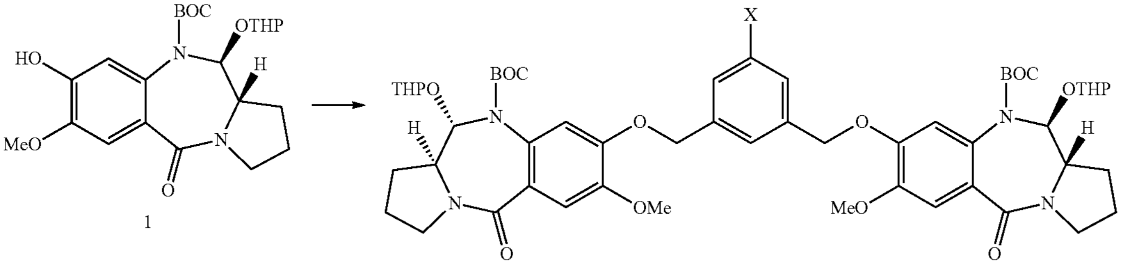

1

2a: X = I
2b: X = Br
2c: X = Cl (i) (11S,11aS,11'S,11a'S)-di-tert-butyl 8,8'-(((5-iodo-1,3-phenylene)bis(methylene))bis(oxy))bis(7-methoxy-5-oxo-11-((tetrahydro-2H-pyran-2-yl)oxy)-2,3,11,11a-tetrahydro-1H pyrrolo[2,1-c][1,4]benzodiazepine-10(5H)-carboxylate) (2a)

1,3-bis(bromomethyl)-5-iodobenzene (906 mg. 2.34 mmol) was added to a stirred solution of Boc/THP-protected PBD capping unit 1 (2.1 g, 4.68 mmol), TBAI (86 mg, 0.234 mmol) and $K_2CO_3$ (647 mg, 4.68 mmol) in dry DMF (30 mL). The reaction mixture was heated to 60° C. and stirred under an argon atmosphere for 3 hours at which point analysis by LC/MS revealed substantial product formation at retention time 4.00 min (ES+) m/z 1125 ($[M+H]^+$; ~50% relative intensity). The reaction mixture was allowed to cool to room temperature and the DMF was removed by evaporation in vacuo. The resulting residue was partitioned between water (50 mL) and EtOAc (50 mL) and the aqueous phase was extracted with EtOAc (3×15 mL). The combined organic layers were washed with water (2×20 mL), brine (40 mL), dried ($MgSO_4$), filtered and evaporated in vacuo to provide the crude product. Purification by flash chromatography (gradient elution: 50:50 v/v EtOAc/hexane to 100% EtOAc) gave the bis-ether 2a as a while foam (2.05 g, 78% yield): $^1$H NMR (400 MHz, $CDCl_3$) (mixture of 3 diastereoisomers) δ 7.78-7.74 (m, 2H), 7.50 (d, 1H, J=4.76 Hz), 7.26 (s, 1H), 7.22 (s, 1H), 6.87 (s, 1H), 6.51 (s, 1H), 5.80 (d, 1H, J=8.52 Hz), 5.70 (d, 1H, J=9.44 Hz), 5.16-4.95 (m, 6H), 3.93-3.87 (m, 8H), 3.74-3.40 (m, 8H), 2.22-1.99 (m, 8H), 1.79-1.22 (m, 30H); $^{13}$C NMR (100 MHz, $CDCl_3$) (mixture of 3 diastereoisomers) δ 167.4, 167.2, 154.9, 149.6, 149.4, 149.2, 148.8, 139.6, 139.4, 135.6 (×2), 129.8, 129.6, 127.9, 127.4, 125.0, 116.0, 115.8, 111.0, 110.4, 100.8, 95.8, 94.8, 91.2, 88.2, 81.4, 80.9, 70.4, 70.0, 64.9, 63.4, 60.2, 60.0, 56.2, 56.1 (×2), 46.3, 31.4, 30.9, 29.2, 28.9, 28.2, 28.1, 25.3, 23.3, 23.2, 20.9, 19.9.

(ii) (11aS,11'S,11a'S)-di-tert-butyl 8,8'-(((5-bromo-1,3-phenylene)bis(methylene))bis(oxybis(methylene))bis(oxy)bis(7-methoxy-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (2b)

1-bromo-3,5-bis(bromomethyl)benzene (331 mg, 0.97 mmol) was added to a stirred solution of Boc/THP-protected PBD capping unit 1 (876 mg, 1.95 mmol), TBAI (36 mg, 97.4 μmol) and $K_2CO_3$ (270 mg, 1.95 mmol) in dry DMF (16 mL). The reaction mixture was heated to 60° C. and stirred under an argon atmosphere for 2.5 hours at which point analysis by LC/MS revealed substantial product formation at retention time 4.00 min (ES+) m/z 1079 ($[M+H]^+$; ~95% relative intensity). The reaction mixture was allowed to cool to room temperature and the DMF was removed by evaporation in vacuo. The resulting residue was partitioned between water (25 mL) and DCM (25 mL) and the aqueous phase was extracted with DCM (3×10 mL). The combined organic layers were washed with water (20 mL), brine (30 mL), dried ($MgSO_4$), filtered and evaporated in vacuo to provide the crude product. Purification by flash chromatography (gradient elution: 50:50 v/v EtOAc/hexane to 100% EtOAc) gave the bis-ether 2b as a white foam (725 mg, 69% yield): $^1$H NMR (400 MHz, $CDCl_3$) (mixture of 3 diastereoisomers) δ 7.57-7.53 (m, 2H), 7.50 (d, 1H, J=4.92 Hz), 7.27 (s, 1H), 7.22 (s, 1H), 6.87 (s, 1H), 6.51 (s, 1H), 5.80 (d, 1H, J=7.88 Hz), 5.70 (d, 1H, J=9.36 Hz), 5.18-4.94 (m, 6H), 3.93-3.85 (m. 8H), 3.75-3.40 (m, 8H), 2.14-1.99 (m, 8H), 1.79-1.22 (m, 30H); $^{13}$C NMR (100 MHz, $CDCl_3$) (mixture of 3 diastereoisomers) δ 167.4, 167.2, 154.9, 149.6, 149.4, 149.2, 148.8, 139.6, 139.4, 129.8, 127.9, 128.0, 127.4, 124.2, 123.2, 116.0, 115.8, 111.0, 110.4, 100.9, 95.8, 91.3, 88.2, 81.3, 80.9, 70.5, 70.1, 64.9, 63.4, 60.2, 60.0, 56.2, 56.1, 46.4, 31.4, 30.9, 29.2, 28.9, 28.2, 28.1, 25.3, 23.3, 23.1, 20.9, 19.9.

(iii) (11S,11aS,11'S,11a'S)-di-tert-butyl 8,8'-(((5-chloro-1,3-phenylene)bis(methylene))bis(oxy))bis(7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (2c)

1,3-bis(bromomethyl)-5-chorobenzene (470 mg, 1.57 mmol) was added to a stirred solution of Boc/THP-protected PBD capping unit 1 (1.41 g, 3.15 mmol), TBAI (58 mg, 0.16 mmol) and $K_2CO_3$ (435 mg, 3.15 mmol) in dry DMF (20 mL). The reaction mixture was heated to 60° C. and stirred under an argon atmosphere for 2 hours at which point analysis by LC/MS (Method A) revealed substantial product formation at retention time 1.94 min (ES+) m/z 1033 ($[M+H]^+$; ~50% relative intensity). The reaction mixture was allowed to cool to room temperature and the DMF was removed by evaporation in vacuo. The resulting residue was partitioned between water (50 mL) and EtOAc (50 mL) and the aqueous phase was extracted with EtOAc (3×15 mL). The combined organic layers were washed with water (2×20 mL), brine (40 mL), dried ($MgSO_4$), filtered and evaporated in vacuo to provide the crude product. Purification by flash chromatography (gradient elution: 50:50 v/v EtOAc/hexane to 100% EtOAc) gave the bis-ether 2c as a white foam (825 mg, 51% yield).

(b) (11S,11aS,11'S,11a'S)-di-tert-butyl 8,8'-(((5-ethynyl-1,3-phenylene)bis(methylene))bis(oxy))bis(7-methoxy-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (4)

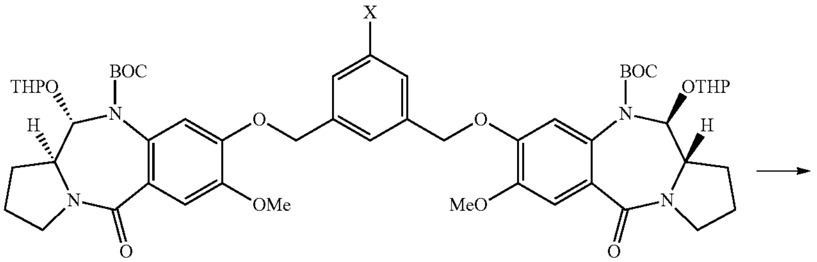

2a: X = I
2b: X = Br

-continued

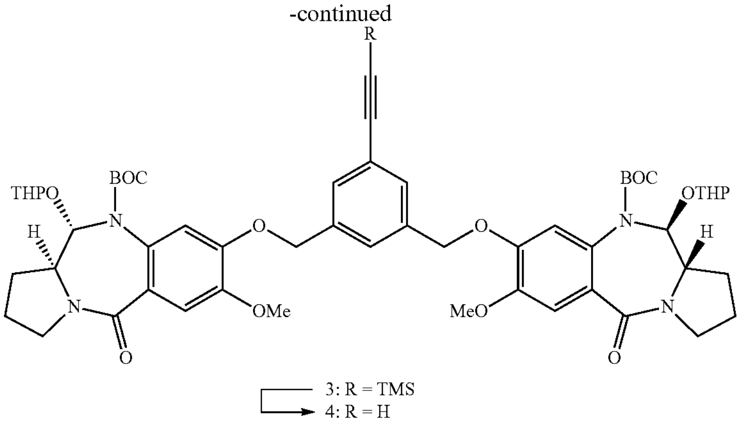

(i) (11S,11aS,11'S,11a'S)-di-tert-butyl 8,8'-(((5-((trimethylsilyl)ethynyl)-1,3-phenylene)bis(methylene))bis(oxy))bis(7-methoxy-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (3)

(ii) (11S,11aS,11'S,11a'S)-di-tert-butyl 8,8'-(((5-ethynyl-1,3-phenylene)bis(methyne))bis(oxy))bis(7-methoxy-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (4)

A catalytic amount of $Pd(PPh_3)_4$ (14.9 mg, 12.9 μmol) was added to a mixture of the bis-ether 2a (721 mg, 0.64 mmol), TMS-acetylene (273 μL, 190 mg, 1.93 mmol), CuI (4.9 mg, 25.8 μmol), diethylamine (1.33 mL, 942 mg, 12.9 mmol) and oven-dried 4 Å molecular sieve pellets in dry DMF (4.8 mL) in an oven-dried sealable vessel. The mixture was degased and flushed with argon 3 times then heated in a microwave at 100° C. for 1.5 hours at which point analysis by LC/MS (Method A) revealed complete consumption of starting material and substantial product formation at retention time 4.27 min (ES+) m/z 1096 ($[M+H]^+$; ~35% relative intensity). Peak at retention time 3.82 min (ES+) m/z 1023 ($[M+H]^+$; ~35% relative intensity) observed which corresponds to TMS-cleavage under LC/MS conditions (Method A). The reaction mixture was allowed to cool to room temperature and was then filtered through a sinter to remove the sieves (washed with DMF). The filtrate was evaporated in vacuo and the resulting residue subjected to flash chromatography (gradient elution: 50:50 v/v EtOAc/hexane to 100% EtOAc) to provide the TMS-acetylene 3 as a yellow foam (656 mg, 93% yield): $^1H$ NMR (400 MHz, $CDCl_3$) (mixture of 3 diastereoisomers) δ 7.52-7.46 (m, 3H), 7.26 (s, 1H), 7.21 (s, 1H), 6.87 (s, 1H), 6.51 (s, 1H), 5.80 (d, 1H, J=8.68 Hz), 5.69 (d, 1H, J=9.36 Hz), 5.18-4.94 (m, 6H), 3.93-3.86 (m, 8H), 3.73-3.40 (m, 8H), 2.13-1.97 (m, 8H), 1.78-1.22 (m, 30H), 0.22, 0.23 and 0.24 (sx3, 9H); $^{13}C$ NMR (100 MHz, $CDCl_3$) δ 167.6, 167.4, 155.2, 155.0, 149.9, 149.6, 149.2, 148.8, 137.8, 137.6, 130.2, 129.9, 129.7, 127.8, 127.2, 125.8, 124.4, 116.0, 115.8, 111.0, 110.4, 104.4, 101.0, 95.8, 91.4, 88.3, 81.4, 81.0, 71.0, 70.6, 65.0, 63.5, 60.3, 60.1, 56.2, 46.4, 31.0, 29.2, 29.0, 28.2, 25.4, 23.4, 23.3, 21.1, 20.0, 0.28, 0.09, 0.00, −0.28.

Solid $K_2CO_3$ (296 mg, 2.14 mmol) was added to a stirred solution of the TMS-protected compound 3 (1.17 g, 1.07 mmol) in MeOH (20 mL). After 3 hours stirring at room temperature the reaction was deemed to be complete as judged by LC/MS (Method A) [desired product peak at retention time 3.82 min (ES+) m/z 1023 ($[M+H]^+$; ~30% relative intensity)]. The MeOH was removed by evaporation in vacuo and the resulting residue was partitioned between water (25 mL) and EtOAc (25 mL). The layers were separated and the aqueous phase was extracted with EtOAc (3×15 mL). The combined organic layers were washed with water (3×30 mL), brine (40 mL), dried ($MgSO_4$), filtered and evaporated in vacuo to provide the crude product. Purification by flash chromatography (gradient elution: 50:50 v/v EtOAc/hexane to 100% EtOAc) gave the acetylene 4 as an orange foam (1.02 g, 94% yield: $^1H$ NMR (400 MHz, $CDCl_3$) (mixture of 3 diastereoisomers) δ 7.55-7.52 (m, 3H), 7.26 (s, 1H), 7.22 (s, 1H), 6.88 (s, 1H), 6.51 (s, 1H), 5.80 (d, 1H, J=8.68 Hz), 5.69 (d. 1H, J =9.48 Hz), 5.18-4.94 (m, 6H), 3.93-3.86 (m, 8H), 3.73-3.40 (m, 8H), 3.09 and 3.08 (sx3, 1H), 2.13-1.97 (m, 8H), 1.78-1.22 (m, 30H); $^{13}C$ NMR (100 MHz, $CDCl_3$) (mixture of 3 diastereoisomers) δ 167.5, 167.3, 155.2, 149.7, 149.5, 149.1, 148.8, 137.8, 137.7, 130.3, 129.8, 129.6, 127.8, 127.2, 126.1, 123.2, 115.9, 115.7, 110.9, 110.4, 100.9, 100.0, 95.7, 91.3, 88.2, 82.9, 81.3, 80.9, 78.0, 70.7, 70.4, 64.9, 63.4, 60.2, 60.0, 56.1, 46.3, 31.4, 30.9, 29.2, 28.9, 28.1 (×2), 25.3, 23.3, 23.2, 20.9, 19.9.

(c) (11S,11aS,11'S,11a'S)-di-tert-butyl 8,8'-(((5-(1-(2-(2-(2-(2-aminoethoxy)ethoxy)ethoxy)ethyl)-1H-1,2,3-triazol-4-yl)-1,3-phenylene)bis(methylene))bis(oxy))bis(7-methoxy-5-oxo-1-((tetrahydro-2H-pyran-2-yl)oxy)-2,3,11,11a-tetrahydro-1H-pyrrolo[2,1-c][1,4]benzodiazepine-10(5H)-carboxylate) (5)

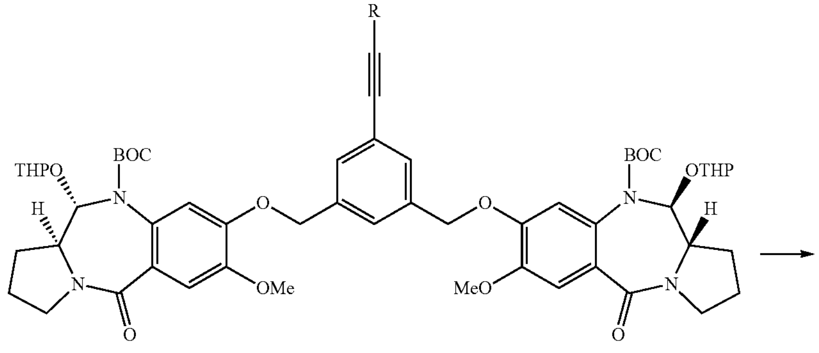

4

R = H

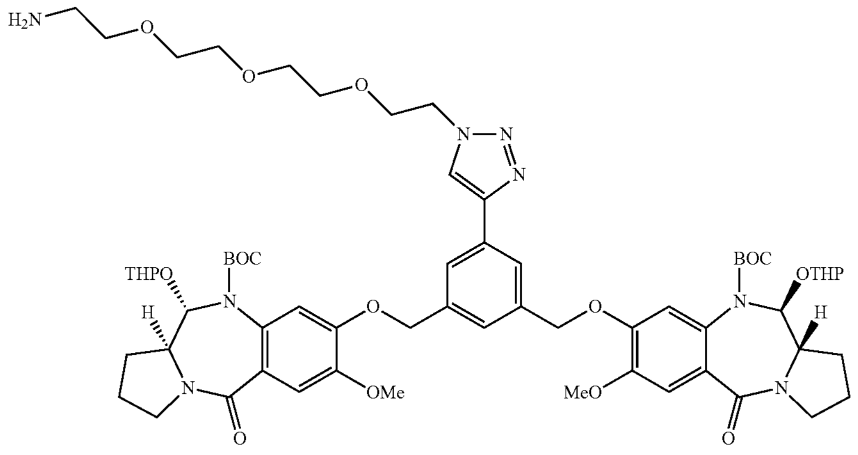

5

Solid $CuSO_4.5H_2O$ (10.3 mg, 41.4 μmol) and (+)-sodium L-ascorbate (33.0 mg, 0.17 mmol) were added to a stirred solution of 11-Azido-3,6,9-trioxaundecan-1-amine (181 mg, 164 μL. 0.83 mmol) and the alkyne 4 (846 mg, 0.83 mmol) in tert-BuOH (5 mL) and $H_2O$ (5 mL) at room temperature. A colour change from yellow to green was observed as the reaction progressed. After stirring for 1.5 hours analysis by LC/MS (Method A) revealed a substantial of amount of desired product formed corresponding to peak at retention time 3.02 min (ES+) m/z 1242 ($[M+H]^+$; ~35% relative intensity). [NOTE: On some occasions reaction progress stalled, however, the reaction was driven to completion upon addition of further $CuSO_4.5H_2O$ (0.05 equivalents) and (+)-sodium L-ascorbate (0.2 equivalents)]. The reaction mixture was partitioned (without shaking of the separating funnel) between water (50 mL) and EtOAc (50 mL). The aqueous phase was extracted with EtOAc (3×20 mL) and the combined organic layers were washed with water (20 mL), brine (30 mL), dried ($MgSO_4$), filtered and evaporated in vacuo to provide the crude product 5 as a green foam (817 mg, 80% crude yield). The crude product was carried through to next step without further purification: $^1H$ NMR (400 MHz, $CDCl_3$) (mixture of 3 diastereoisomers) δ 7.98-7.83 (m, 3H), 7.55-7.48 (br s, 1H), 7.31-7.22 (m, 2H). 6.96 (br s, 1H), 6.57 (s, 1H). 5.85-5.78 (m, 1H), 5.72-5.68 (m, 1H), 5.18-4.94 (m, 6H), 4.60-4.50 (m, 2H), 3.93-3.80 (m, 12H), 3.73-3.40 (m, 12H), 2.13-1.80 (m, 8H), 1.71-1.10 (m, 30H).

(d) (11S,11aS,11'S,11a'S)-di-tert-butyl 8,8'-(((5-(1-(18-(2,5-dioxo-2,5-dihydro-1H-pyrrol-1-yl)-13-oxo-3,6,9-trioxa-12-azaoctadecyl)-1H-1,2,3-triazo-4-yl)-1,3-phenylene)bis(methylene))bis(oxy))bis(7-methoxy-5-oxo-11-((tetrahydro-2H-pyran-2-yl)oxy)-2,3,11,11a-tetrahydro-1H-pyrrolo[2,1-c][1,4]benzodiazepine-10(5H)-carboxylate) (6)

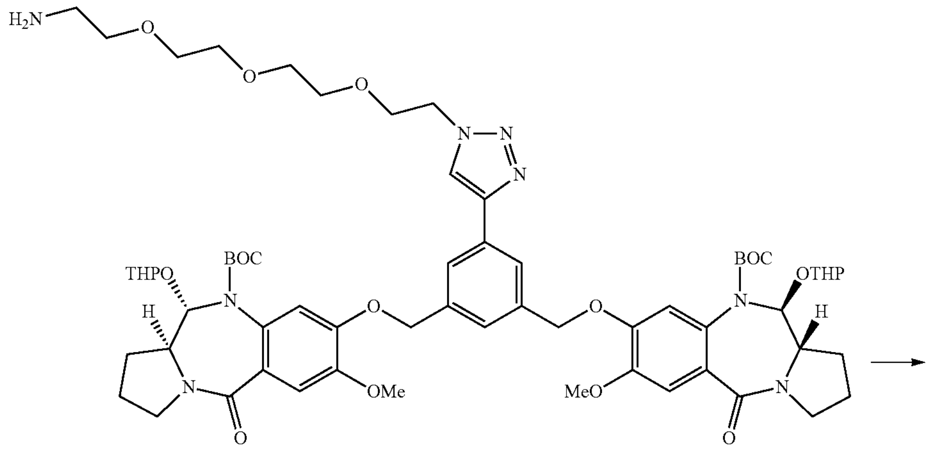

5

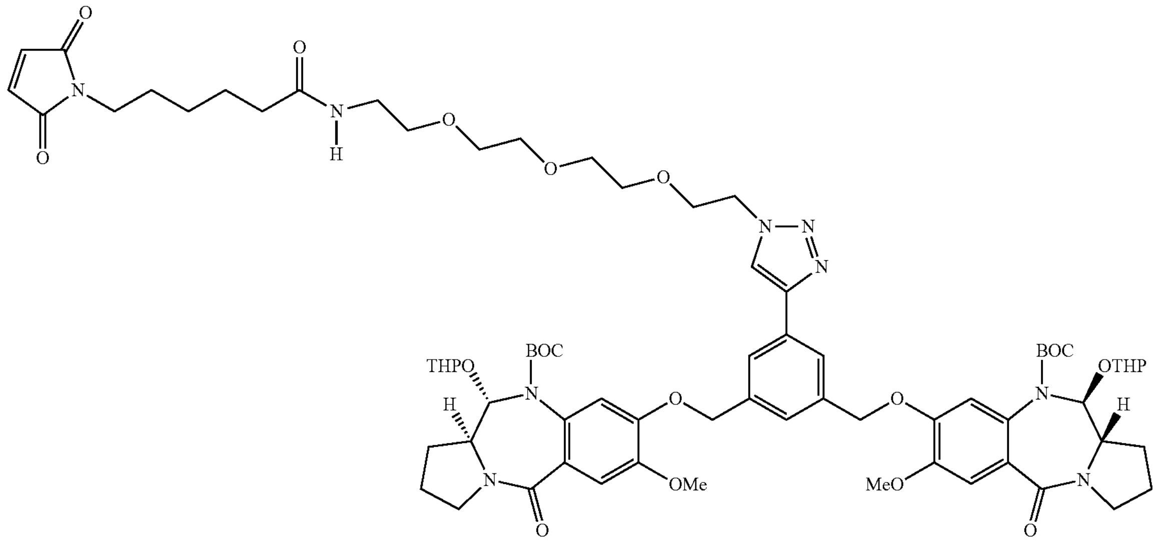

6

Solid 6-maleimidohexanoic acid N-hydroxysuccinimide ester (136 mg, 0.44 mmol) was added to a stirred solution of the primary amine 5 (523 mg, 0.42 mmol) in dry DCM (10 mL) at room temperature. Progress was monitored by LC/MS (Method A) and after 3 days stirring the reaction proceeded no further, a substantial amount of desired product was observed at retention time 3.48 min (ES+) m/z 1434 ($[M+H]^+$; ~30% relative intensity) accompanied by a shoulder peak at retention time 3.40 min and unreacted starting material at retention time 3.02 min. The reaction mixture was treated with silica gel and the solvent removed by evaporation in vacuo. The resulting residue was subjected to flash chromatography (gradient elution: 100% DCM to 97:3 v/v DCM/MeOH) to give the maleimide 6 as a white foam (253 mg, 42% yield): $^1$H NMR (400 MHz, $CDCl_3$) (mixture of 3 diastereoisomers) δ 8.05-7.99 (nm, 1H), 7.92-7.87 (m, 2H), 7.56, 7.55 and 7.53 (sx3, 1H), 7.26 and 7.22 (sx2, 2H), 6.94 (s, 1H), 6.66 (s, 2H), 6.58 (s, 1H), 6.04 (brs, 1H), 5.80 (d, 1H, J=6.88 Hz), 5.70 (d, 1H, J=9.16 Hz), 5.24-4.94 (m, 6H), 4.60 (t, 2H, J=4.68 Hz), 3.95-3.86 (m, 10H), 3.69-3.37 (m, 22H), 2.15-1.97 (m, 10H), 1.75-1.22 (m, 36H); $^{13}$C NMR (100 MHz, $CDCl_3$) (mixture of 3 diastereoisomers) δ 172.8, 170.8, 167.6, 167.4, 149.1, 137.9, 134.1, 129.8, 124.2, 115.8, 115.6, 110.3, 95.8, 71.1, 70.8, 70.6, 70.5 (x2), 70.2, 69.9, 69.5, 63.4, 60.2, 56.1, 53.4, 50.5, 46.4, 39.1, 37.7, 36.3, 31.4, 30.9, 29.2, 28.9, 28.3, 28.1, 26.4, 25.3 (x2), 25.1, 23.3, 23.2, 19.9.

(e) N-(2-(2-(2-(2-(4-(3,5-bis((((S)-7-methoxy-5-oxo-2,3,5,11a-tetrahydro-1H-pyrrolo[2,1-c][1,4]benzodiazepin-8-yl)oxy)methyl)phenyl)-1H-1,2,3-triazol-1-yl)ethoxy)ethoxy)ethoxy)ethoxy)ethyl)-6-(2,5-dioxo-2,5-dihydro-1H-pyrrol-1-yl)hexanamide (7)
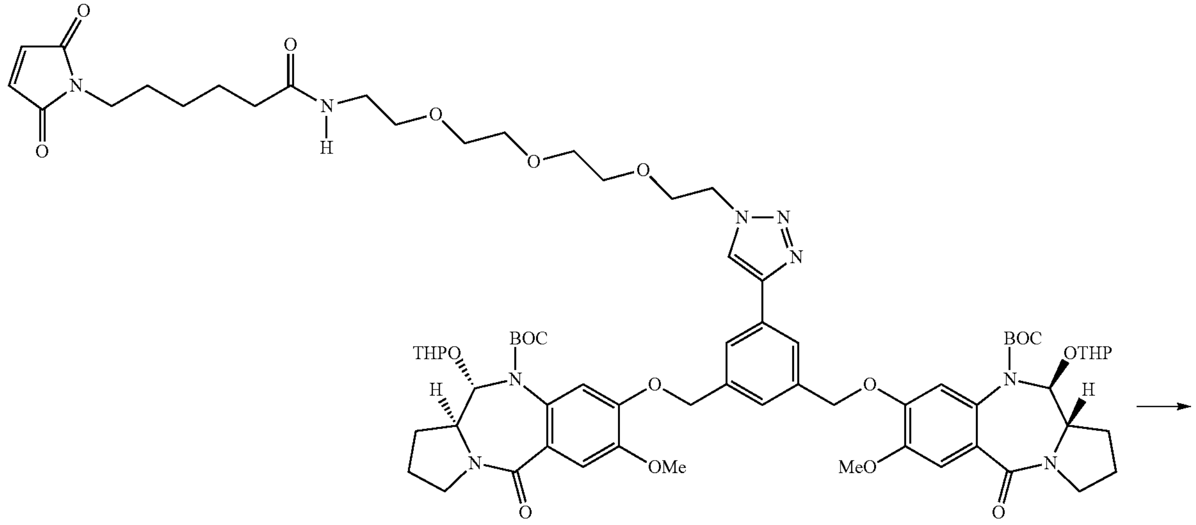
6
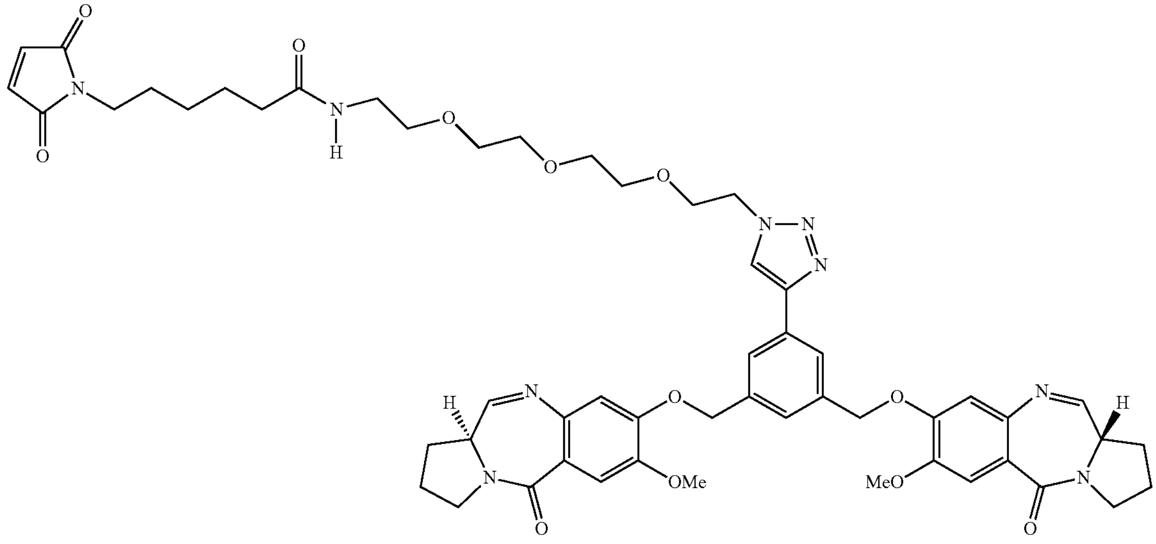
7

A solution of 95:5 v/v TFA/$H_2O$ (3 mL) was added to a sample of the Boc/THP-protected compound 6 (253 mg, 0.18 mmol) at 0° C. (ice/acetone). After stirring at 0° C. for 1 hour the reaction was deemed complete as judged by LC/MS (Method A), desired product peak at retention time 2.63 min (ES+) m/z 1030 ($[M+H]^+$; ~30% relative intensity). The reaction mixture was kept cold and added drop wise to a chilled saturated aqueous solution of $NaHCO_3$ (50 mL). The mixture was extracted with DCM (3×15 mL) and the combined organic layers washed with brine (20 mL), dried ($MgSO_4$), filtered and evaporated in vacuo to provide the crude product. Purification by flash chromatography (gradient elution: 100% $CHCl_3$ to 97:3 v/v $CHCl_3$/MeOH) gave the title compound as an orange foam (127 mg, 70% yield).

Example 2

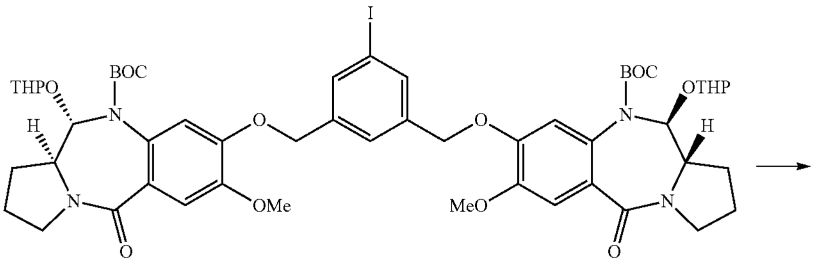

2a

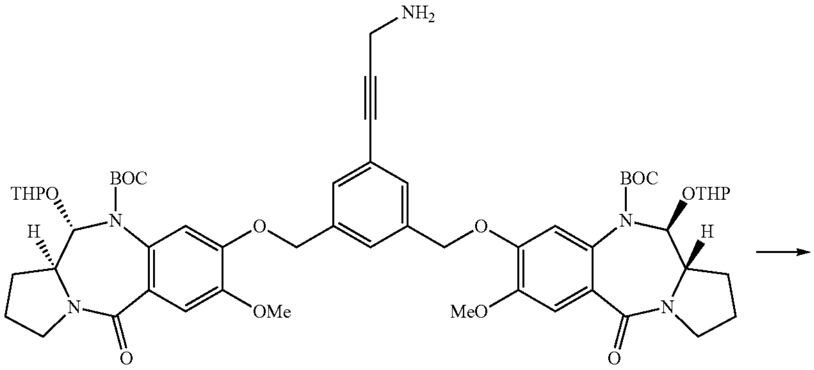

8

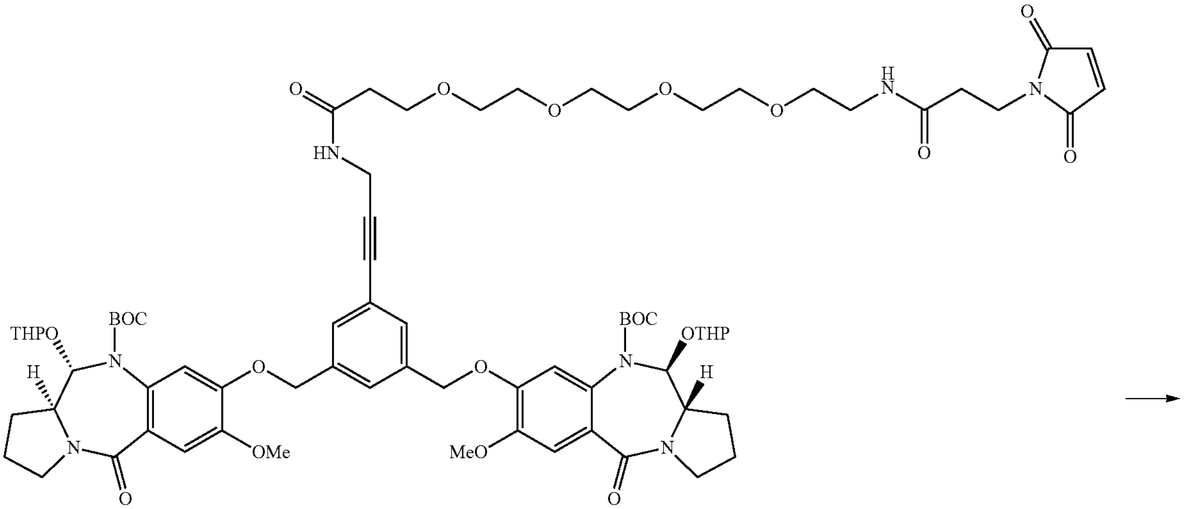

9

-continued

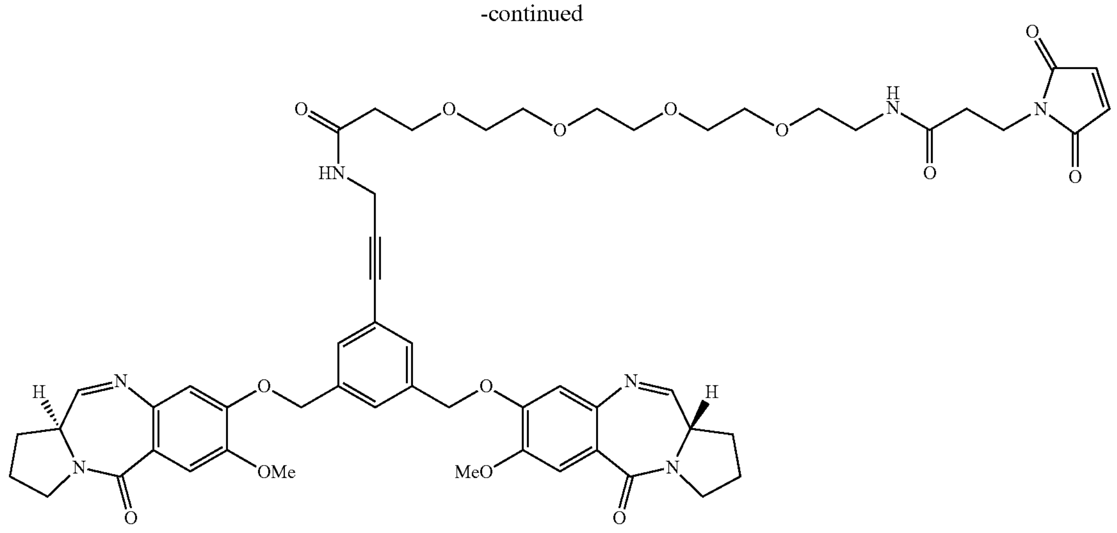

10

(a) (11S,11aS,11'S,11a'S)-di-tert-butyl 8,8'-((5-(3-aminoprop-1-yn-1-yl)-1,3-phenylene)bis(methylene))bis(oxy))bis(7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (8)

A catalytic amount of $Pd(PPh_3)_4$(2.05 mg, 1.75 μmol) was added to a mixture of the bis-ether 2a (100 mg, 0.089 mmol), propargylamine (17 μL, 15 mg, 0.26 mmol), CuI (0.65 mg, 3.5 μmol), diethylamine (18 μL, 13 mg, 1.75 mmol) and oven-dried 4 Å molecular sieve pellets in dry DMF (1.5 mL) in an oven-dried sealable vessel. The mixture was degased and flushed with argon 3 times then heated at 100° C. for 2 hours in the sealed vessel. At this point, analysis by LC/MS (Method C) revealed complete consumption of starting material and substantial product formation at retention time 1.36 min (ES+) nm/z 1052.95 ($[M+H]^+$; 100% relative intensity). The reaction mixture was allowed to cool to room temperature and was then filtered through a sinter to remove the sieves (washed with DMF). The filtrate was evaporated in vacuo to provide unstable crude product 8, which was used immediately in the next step without purification or analysis.

(b) (11S,11aS,11'S,11a'S)-di-tert-butyl 8,8'-(((5-(1-(2,5-dioxo-2,5-dihydro-1H-pyrrol-1-yl)-3,19-dioxo-7,10,13,16-tetraoxa-4,20-diazatricos-22-yn-23-yl)-1,3-phenylene)bis(methylene))bis(oxy))bis(7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (9)

MAL-dPEG®4-acid (37 mg, 0.089 mmol) was added to a stirred solution of EDCI (17 mg, 0.089 mmol) and the crude primary amine 8 in dry DCM (4 mL) at room temperature. The reaction mixture was stirred under an argon atmosphere for 3 hours at which point analysis by LC/MS (Method C) showed a substantial amount of desired product at retention time 1.69 min (ES+) m/z 1450.55 ($[M+H]^+$; ~10% relative intensity), 1498 ($[M+Na]^+$; ~80% relative intensity). The reaction mixture was diluted with DCM (30 mL) and washed with $H_2O$ (3×10 mL), brine (20 mL), dried ($MgSO_4$), filtered and evaporated in vacuo to provide the crude product. Purification by flash chromatography (gradient elution: 100% DCM to 96:4 v/v DCM/MeOH) gave maleimide 9 as a foam (80 mg, 62% yield over 2 steps).

(c) N-(3-(3,5-bis((((S)-7-methoxy-5-oxo-2,3,5,11a-tetrahydro-1H-benzo[e]pyrrolo[1,2-a][1,4]diazepin-8-yl)oxy)methyl)phenyl)prop-2-yn-1-yl)-1-(3-(2,5-dioxo-2,5-dihydro-1H-pyrrol-1-yl)propanamido)-3,6,9,12-tetraoxapentadecan-15-amide (10)

A solution of 95:5 v/v TFA/$H_2O$ (1 mL) was added to a sample of the Boc/THP-protected compound 9 (80 mg, 55 μmol) at 0° C. (ice/acetone). After stirring at 0° C. for 1 hour, the reaction was deemed complete as judged by LC/MS (Method C), desired product peak at retention time 1.24 min (ES+) m/z 1046.35 ($[M+H]^+$; 100% relative intensity). The reaction mixture was kept cold and added drop wise to a chilled saturated aqueous solution of $NaHCO_3$ (50 mL). The mixture was extracted with DCM (3×15 mL) and the combined organic layers washed with brine (40 mL), dried ($MgSO_4$), filtered and evaporated in vacuo to provide the crude product. Purification by flash chromatography (gradient elution: 100% $CHCl_3$ to 96:4 v/v $CHCl_3$/MeOH) gave 10 as an orange solid (9 mg, 16% yield).

Example 3
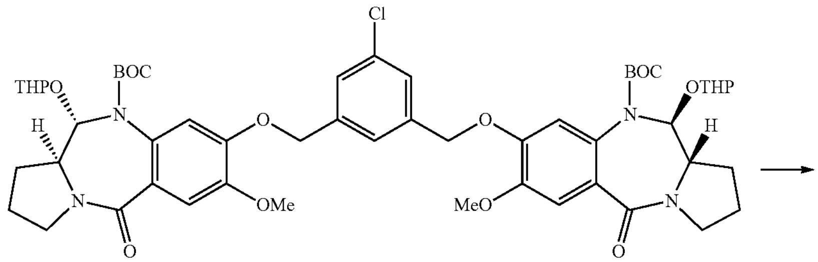
2c
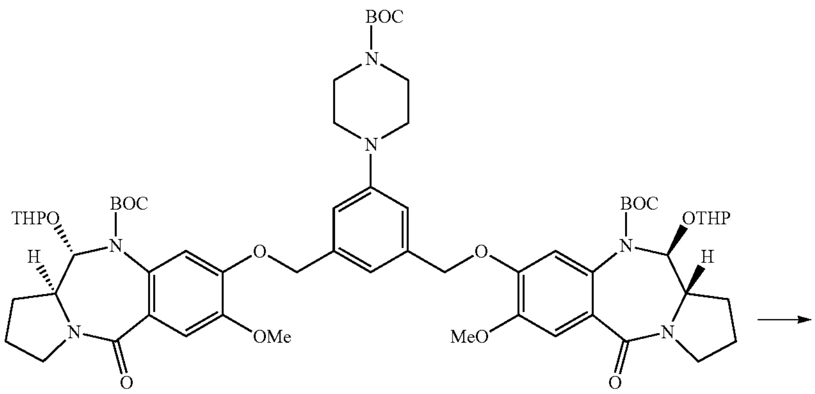
11
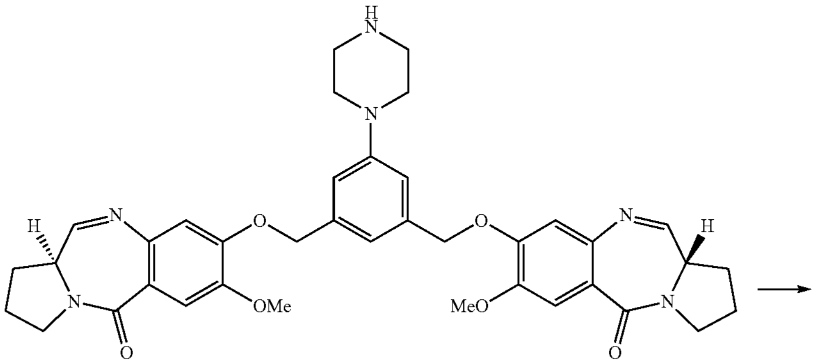
12

-continued

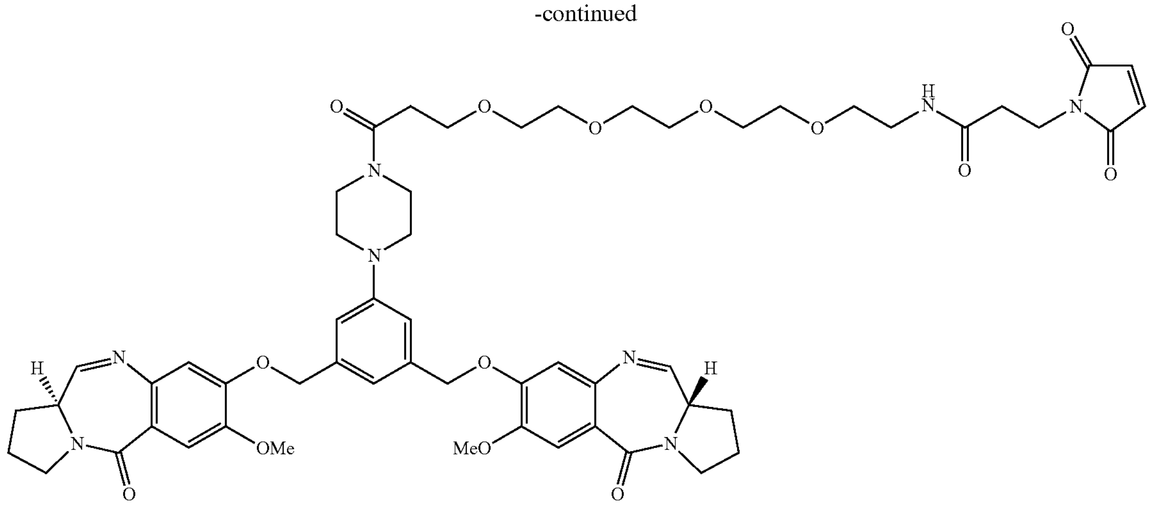

13

(a) (11S,11aS,11'S,11a'S)-di-tert-butyl 8,8'-(((5-(4-(tert-butoxycarbonyl)piperazin-1-yl)-1,3-phenylene) bis(methylene))bis(oxy))bis(7-methoxy-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate) (11)

A catalytic amount of RuPhosPd (15.8 mg, 0.019 mmol) was added to a mixture of the bis-ether 2c (200 mg, 0.19 mmol), 1-Boc-piperazine (39.6 mg, 0.21 mmol), $CsCO_3$ (157 mg, 0.48 mmol) and RuPhos (9 mg, 0.019 mmol) in dry THF (4 mL) in an oven-dried sealable vessel. The mixture was degased and flushed with argon 3 times then heated in a preheated drysyn at 85° C. for 2h letting the pressure to build up in the vial. At this point, analysis by LC/MS (Method C) revealed complete consumption of starting material and substantial product formation at retention time 1.97 min (ES+) m/z 1083.45 ($[M+H]^+$; 5% relative intensity). The reaction mixture was allowed to cool to room temperature and diluted with ethyl acetate (50 mL) The organics were washed with $H_2O$ (2×25 mL) and brine (25 mL) before being dried over $MgSO_4$, filtered and the volatiles removed under reduced pressure. The crude material was purified by silica gel chromatography column (gradient elution: 100% $CHCl_3$ to 9:1 v/v $CHCl_3$/MeOH) and isolated pure as a white foam (210 mg, 91% yield).

(b) (11aS,11a'S)-8,8'(((5-(piperazin-1-yl)-1,3-phenylene)bis(methylene))bis(oxy))bis(7-methoxy-2,3-dihydro-1H-benzo[e]pyrrolo[1,2-a][1,4]diazepin-5 (11aH)-one) (12)

A solution of 95:5 v/v TFA/$H_2O$ (1 mL) was added to a sample of the Boc/THP-protected compound 11 (100 mg, 0.084 mmol) at 0° C. (ice/water). After stirring at 0° C. for 1 hour, the reaction was deemed complete as judged by LC/MS (Method C), desired product peak at retention time 1.02 min (no ionisation observed for this compound). The reaction mixture was kept cold and added drop wise to a chilled saturated aqueous solution of $NaHCO_3$ (50 mL). The mixture was extracted with DCM (3×15 mL) and the combined organic layers washed with brine (40 mL), dried ($MgSO_4$), filtered and evaporated in vacuo to provide the crude product which was used as such in the next step.

(c) N-(15-(4-(3,5-bis((((S)-7-methoxy-5-oxo-2,3,5,11a-tetrahydro-1H-benzo[e]pyrrolo[1,2-a][1,4]diazepin-8-yl)oxy)methyl)phenyl)piperazin-1-yl)-15-oxo-3,6,9,12-tetraoxapentadecyl)-3-(2,5-dioxo-2,5-dihydro-1H-pyrrol-1-yl)propanamide (13)

MAL-dPEG®4-acid (35 mg, 0.084 mmol) was added to a stirred solution of EDCI (16 mg, 0.084 mmol) and the crude primary amine 12 in dry DCM (3 mL) at room temperature. The reaction mixture was stirred under an argon atmosphere for 3 hours at which point analysis by LC/MS (Method C) showed a substantial amount of desired product at retention time 1.24 min (ES+) m/z 1077.40 ($[M+H]^+$; 90% relative intensity). The reaction mixture was diluted with DCM (30 mL) and washed with $H_2O$ (3×10 mL), brine (20 mL), dried ($MgSO_4$), filtered and evaporated in vacuo to provide the crude product. Purification by preparatory UPLC (gradient elution: 87:13 v/v $H_2O/CH_3CN$ to 15:75 v/v $H_2O/CH_3CN$ over 11 min) gave final product 13 as a light brown oil (4.7 mg, 5% yield over 2 steps).

Example 4

(a) (S)-(2-amino-5-methoxy-4-((triisopropylsilyl) oxy)phenyl)(2-(((tert-butyldimethylsilyl)oxy) methyl)-4-methyl-2,3-dihydro-1H-pyrrol-1-yl) methanone (17)

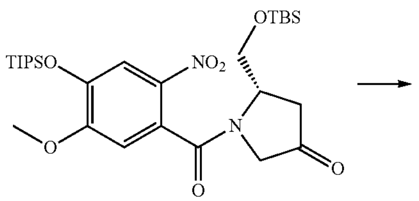

14

-continued

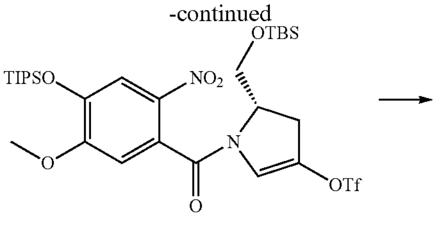

15

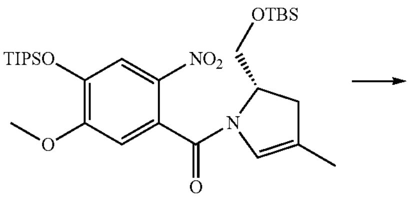

16

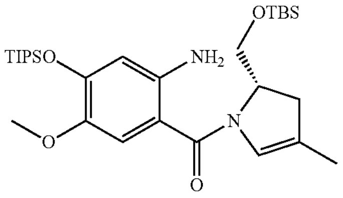

17

(i) (S)-5-(((tert-butyldimethylsilyl)oxy)methyl)-1-(5-methoxy-2-nitro-4-((triisopropylsilyl)oxy)benzoyl)-4,5-dihydro-1H-pyrrol-3-yl trifluoromethanesulfonate (15)

Triflic anhydride (26 mL, 155 mmol, 3 eq) was injected (temperature controlled) to a vigorously stirred suspension of ketone 14 (30 g, 52 mmol, 1 eq) in dry dichloromethane (500 mL) in the presence of 2,6-lutidine (24 mL, 207 mmol, 4 eq, dried over sieves) at −50° C. (acetone/dry ice bath). The reaction mixture was allowed to stir for 1 hour. Water was added to the still cold reaction mixture and the organic layer was separated and washed with saturated sodium bicarbonate, brine and magnesium sulphate. The organic phase was filtered and excess solvent was removed by rotary evaporation under reduced pressure. The residue was subjected to column flash chromatography (silica gel; 5% ethyl acetate/hexane). Pure fractions were collected and combined, and excess eluent was removed by rotary evaporation under reduced pressure afforded the product 15 (31.5 g, 86%). LC/MS, method B, 4.32 min (ES+) m/z (relative intensity) 712.89 ([M+H]$^+$; 100); $^1$H NMR (400 MHz, $CDCl_3$) δ 7.71 (s, 1H), 6.75 (s, 1H), 6.05 (d, J=1.8 Hz, 1H), 4.78 (dd, J=9.8, 5.5 Hz, 1H), 4.15-3.75 (m, 5H), 3.17 (ddd, J=16.2, 10.4, 2.3 Hz, 1H), 2.99 (ddd, J=16.3, 4.0, 1.6 Hz, 1H), 1.45-1.19 (m, 3H), 1.15-1.08 (m, 18H), 1.05 (s, 6H), 0.95-0.87 (m, 9H), 0.15-0.08 (m, 6H).

(ii) (S)-(2-(((tert-butyldimethylsilyl)oxy)methyl)-4-methyl-2,3-dihydro-1H-pyrrol-1-yl)(5-methoxy-2-nitro-4-((triisopropylsilyl)oxy)phenyl) methanone (16)

Triphenylarsine (1.71 g, 5.60 mmol, 0.4 eq) was added to a mixture of triflate 15 (10.00 g, 14 mmol, 1 eq), methylboronic acid (2.94 g, 49.1 mmol, 3.5 eq), silver oxide (13 g, 56 mmol, 4 eq) and potassium phosphate tribasic (17.8 g, 84 mmol, 6 eq) in dry dioxane (80 mL) under an argon atmosphere. The reaction was flushed with argon 3 times and bis(benzonitrile)palladium(II) chloride (540 mg, 1.40 mmol, 0.1 eq) was added. The reaction was flushed with argon 3 more times before being warmed instantaneously to 110° C. After 10 minutes the reaction was cooled to room temperature and filtered through a pad celite. The solvent was removed by rotary evaporation under reduced pressure. The resulting residue was subjected to column flash chromatography (silica gel; 10% ethyl acetate/hexane). Pure fractions were collected and combined, and excess eluent was removed by rotary evaporation under reduced pressure afforded the product 16 (4.5 g, 55%). LC/MS, method B, 4.27 min (ES+) m/z (relative intensity) 579.18 ([M+H]$^+$; 100); $^1$H NMR (400 MHz, $CDCl_3$) δ 7.70 (s, 1H), 6.77 (s, 1H), 5.51 (d, J=1.7 Hz, 1H), 4.77-4.59 (m, 1H), 3.89 (s, 3H), 2.92-2.65 (m, 1H), 2.55 (d, J=14.8 Hz, 1H), 1.62 (d, J=1.1 Hz, 3H), 1.40-1.18 (m, 3H), 1.11 (s, 9H), 1.10 (s, 9H), 0.90 (s, 9H), 0.11 (d, J=2.3 Hz, 6H).

(iii) (S)-(2-amino-5-methoxy-4-((triisopropylsilyl)oxy)phenyl(2-(((tert-butyldimethylsilyl)oxy)methyl)-4-methyl-2,3-dihydro-1H-pyrrol-1-yl)methanone (17)

Zinc powder (5.6 g, 86 mmol, 5 eq) was added to a solution of compound 3 (10 g, 17.3 mmol) in 5% formic acid in methanol v/v (100 mL) at around 15° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 10% ethyl acetate in hexane). The pure fractions were collected and combined and excess solvent was removed by rotary evaporation under reduced pressure to afford the product 17 (5.1 g, 80%). LC/MS, method B, 4.23 min (ES+) m/z (relative intensity) 550.21 ([M+H]$^+$; 100); $^1$H NMR (400 MHz, $CDCl_3$) δ 7.28 (s, 1H), 6.67 (s, 1H), 6.19 (s, 1H), 4.64-4.53 (m, J=4.1 Hz, 1H), 4.17 (s, 1H), 3.87 (s, 1H), 3.77-3.69 (m, 1H), 3.66 (s, 3H), 2.71-2.60 (m, 1H), 2.53-2.43 (m, 1H), 2.04-1.97 (m, J=11.9 Hz, 1H), 1.62 (s, 3H), 1.26-1.13 (m, 3H), 1.08-0.99 (m, 18H), 0.82 (s, 9H), 0.03-0.03 (m, J=6.2 Hz, 6H).

(b) (11S,11aS)-tert-butyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (22)

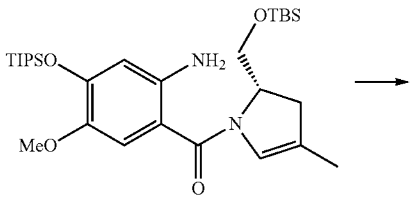

17

-continued

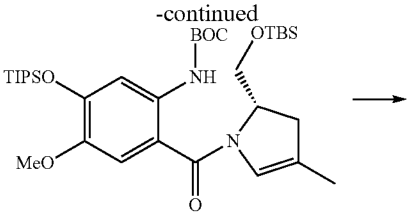

18

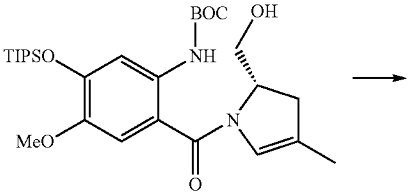

19

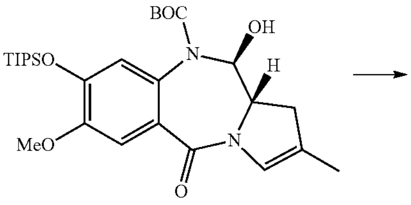

20

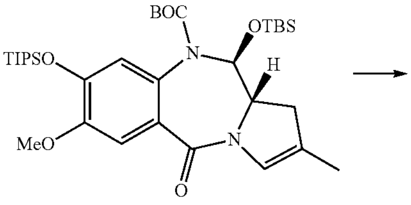

21

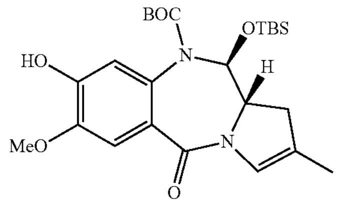

22

(i) (S)-tert-butyl (2-(2-(((tert-butyldimethylsilyl) oxy)methyl)-4-methyl-2,3-dihydro-1H-pyrrole-1-carbonyl)-4-methoxy-5-((triisopropylsilyl)oxy)phenyl)carbamate (18)

Di-tert-butyl dicarbonate (2.8 g, 12.90 mmol, 1.2 eq) was melted with amine 17 (5.9 g, 10.75 mmol) at 100° C. After 10 minutes, full conversion was observed and the residue was subjected to flash column chromatography (silica gel; 5% ethyl acetate in hexane). The pure fractions were collected and combined and excess solvent was removed by rotary evaporation under reduced pressure to afford the product 18 (6 g, 86%). $^1$H NMR (400 MHz, $CDCl_3$) δ 8.22 (s. 1H), 7.72 (s, 1H), 6.72 (s, 1H), 6.15 (s, 1H), 4.63 (s, 1H), 3.91 (s, 1H), 3.79 (s, 1H), 3.73 (s, 3H), 2.71 (dd, J=16.1, 10.2 Hz, 1H), 2.60-2.46 (m, 1H), 1.64 (s, 3H), 1.46 (s, 9H), 1.33-1.15 (m, 3H), 1.10 (s, 9H), 1.08 (s, 9H), 0.87 (s, 9H), 0.02 (s, 6H).

(ii) (S)-tert-butyl (2-(2-(hydroxymethyl)-4-methyl-2,3-dihydro-1H-pyrrole-1-carbonyl)-4-methoxy-5-((triisopropylsilyl)oxy)phenyl)carbamate (19)

18 (9.87 g, 15.2 mmol) was dissolved in a 7:1:1:2 mixture of acetic acid/methanol/tetrahydrofuran/water (168:24:24:48 mL) and allowed to stir at room temperature. After 1 hour, complete conversion was observed. Solvent was removed by rotary evaporation under reduced pressure. The residue was diluted with ethyl acetate and washed sequentially with water (2×500 mL), saturated aqueous sodium bicarbonate (200 mL) and brine. The organic phase was dried over magnesium sulphate, filtered and excess ethyl acetate removed by rotary evaporation under reduced pressure to afford the desired product 19 (7.91 g, 97%). LC/MS, Method C, 2.13 min (ES+) m/z (relative intensity) 1092.45 [[2M+Na]$^+$; $^1$H NMR (400 MHz, $CDCl_3$) δ 7.93 (s, 1H), 7.60 (s, 1H), 6.74 (s, 1H), 6.11 (s, 1H), 4.69 (br, 1H), 4.55 (br, 1H), 3.84-3.76 (m, 2H), 3.74 (s, 3H), 2.84 (dd, J=16.6, 10.3 Hz, 1H), 2.19 (dd, J=16.4, 4.0 Hz, 1H), 1.67 (s, 3H), 1.46 (s, 9H), 1.32-1.19 (m, 3H), 1.09 (s, 9H), 1.08 (s, 9H).

(iii) (11S,11aS)-tert-butyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (20)

Dimethyl sulphoxide (2.3 mL, 32.2 mmol, 2.5 eq) was added dropwise to a solution of oxalyl chloride (1.3 mL, 15.5 mmol, 1.2 eq) in dry dichloromethane (70 mL) at −78° C. (dry ice/acetone bath) under an atmosphere of argon. After 10 minutes, a solution of 19 (6.9 g, 12.9 mmol) in dry dichloromethane (50 mL) was added slowly with the temperature still at −78° C. After 15 minutes, triethylamine (9 mL, dried over 4A molecular sieves, 64.5 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 20 (4.36 g, 63%). LC/MS, Method C, 2.01 min (ES+) m/z (relative intensity) 1087.45 ([2M+Na]$^+$); $^1$H NMR (400 MHz, $CDCl_3$) δ 7.17 (s, 1H), 6.70 (d, 1H), 6.65 (s, 1H), 5.74-5.61 (m, 1H), 4.03 (s, 1H), 3.82 (s, 3H), 3.75 (td, J=9.9, 3.3 Hz, 1H), 2.94 (dd, J=17.1, 10.2 Hz, 1H), 2.57 (d, J=18.5 Hz, 1H), 1.75 (d, J=7.5 Hz, 3H), 1.37 (s, 9H), 1.30-1.19 (m, 3H), 1.08 (s, 9H), 1.06 (s, 9H).

(iv) (11S,11aS)-tert-butyl 11-((tert-butyldimethylsilyl)oxy)-7-methoxy 2-methyl-5-oxo-8-((triisopropylsilyl)oxy)-11,11a-dihydro-1H-benzo[e]pyrrolo[1,2-a][1,4]diazepine-10(5H)-carboxylate (21)

Tert-butyldimethylsilyltriflate (6.5 mL, 28.39 mmol, 3 eq) was added to a solution of compound 20 (5.04 g, 9.46 mmol) and 2,6-lutidine (4.4 mL, 37.86 mmol, 4 eq) in dry dichloromethane (60 mL) at 0° C. under argon. After 10 minutes, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure to give the product 21 (5.18 g, 85%). $^1$H NMR (400 MHz, $CDCl_3$) δ 7.17 (s, 1H), 6.67 (s, 1H), 6.63 (s, 1H), 5.79 (d, J=8.9 Hz, 1H), 3.84 (s, 3H), 3.65 (td, J=9.9, 3.8 Hz, 1H), 2.89 (dd, J=16.9, 10.3 Hz, 1H), 2.35 (d, J=16.7 Hz, 1H), 1.75 (s, 3H), 1.31 (s, 9H), 1.28-1.18 (m, 3H), 1.09 (s, 9H), 1.08 (s, 9H), 0.85 (s, 9H), 0.25 (s, 3H), 0.18 (s, 3H).

(v) (11S,11aS)-tert-butyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (22)

Lithium acetate (800 mg, 7.73 mmol) was added to a solution of compound 21 (5 g, 7.73 mmol) in wet dimethylformamide (50 mL, 50:1 DMF/water). After 2 hours, the reaction was complete and the reaction mixture was diluted with ethyl acetate (250 mL) and washed with aqueous citric acid solution (pH~3), water and brine. The organic layer was dried over magnesium sulphate, filtered and excess ethyl acetate was removed by rotary evaporation under reduced pressure. The resulting residue was subjected to flash column chromatography (silica gel; gradient. 25% to 50% ethyl acetate in hexane). Pure fractions were collected, combined and excess eluent was removed by rotary evaporation under reduced pressure to give the product 22 (3.14 g, 83%). LC/MS, Method C, (1.92 min (ES+) m/z (relative intensity) 491.25 ([M+H]$^+$). $^1$H NMR (400 MHz, $CDCl_3$) δ 7.20 (s, 1H), 6.68 (s, 2H), 6.08 (s, 1H), 5.81 (d, J=8.9 Hz, 1H), 3.91 (s, 3H), 3.71 (td, J=9.8, 3.8 Hz, 1H), 2.89 (dd, J=16.9, 10.3 Hz, 1H), 2.36 (d, J=16.9 Hz, 1H), 1.75 (s, 3H), 1.31 (s, 9H), 0.85 (s, 9H), 0.23 (s, 3H), 0.21 (s, 3H).

(c) (11S,11aS,11'S,11a'S)-di-tert-butyl 8,8'(((5-(1-amino-5-oxo-3,6,9,12-tetraoxa-16-azanonadec-18-yn-19-yl)-1,3-phenylene)bis(methylene))bis(oxy))bis(11-hydroxy-7-methoxy-2-methyl-5-oxo-11,11a-dihydro-1H-benzo[e]pyrrolo[1,2-a][1,4]diazepine-10(5H)-carboxylate) (25)

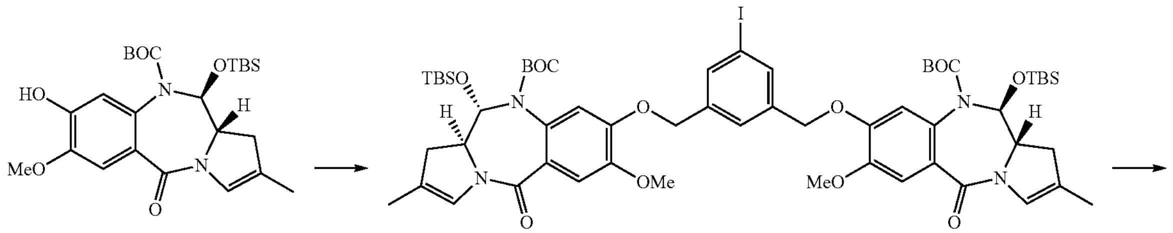

22

23

+

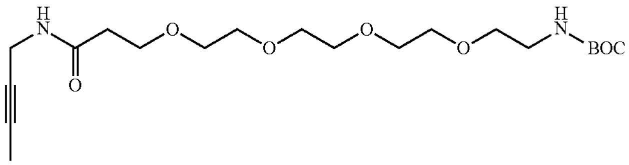

I3

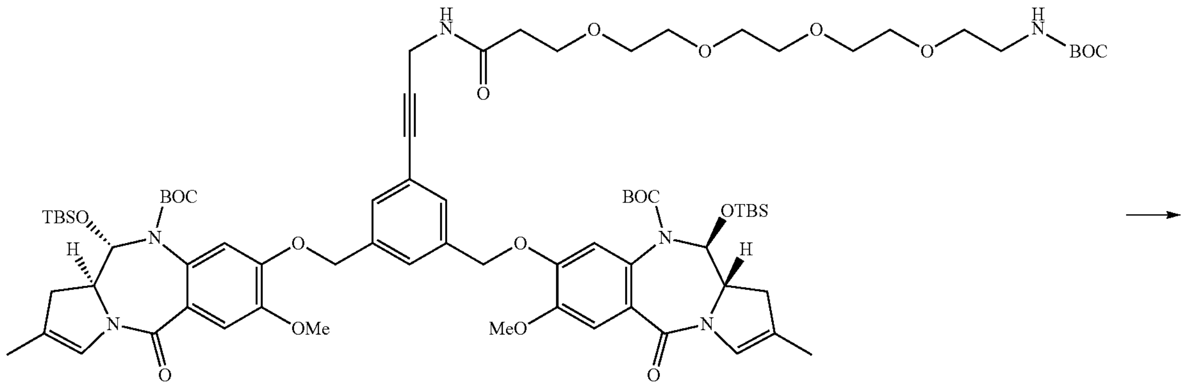

24

-continued

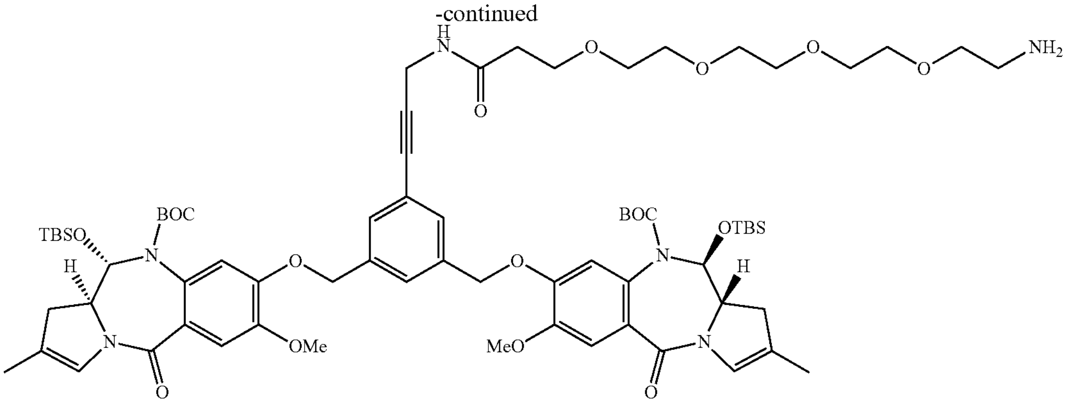

25

(i) (11S,11aS,11'S,11a'S)-di-tert-butyl 8,8'-((5-iodo-1,3-phenylene)bis(methylene))bis(oxy))bis(11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate) (23)

1,3-bis(bromomethyl)-5-iodobenzene (400 mg, 1.02 mmol) was added to a stirred solution of 22 (1 g, 2.04 mmol, 2 eq), TBAI (38 mg, 0.102 mmol, 0.1 eq) and $K_2CO_3$(282 mg. 2.04 mmol, 2 eq) in dry DMF (10 mL). The reaction mixture was heated to 60° C. and stirred under an argon atmosphere for 2 hours at which point analysis by TLC showed full conversion. The reaction mixture was allowed to cool to room temperature and the DMF was removed by rotary evaporation under reduced pressure. The resulting residue was diluted in EtOAc and washed with water, brine. The organic layer was dried over magnesium sulphate, filtered and excess ethyl acetate was removed by rotary evaporation under reduced pressure. The resulting residue was subjected to flash column chromatography (silica gel; gradient, 50% to 80% ethyl acetate in hexane). Pure fractions were collected and combined and excess eluent was removed by rotary evaporation under reduced pressure to give the product 22 (1.27 g, quant.). LC/MS, Method C, (2.38 min (ES+) m/z (relative intensity) 1232.35. ([M+Na]$^+$), $^1$H NMR (400 MHz, $CDCl_3$) δ 7.75 (s, 2H), 7.50 (s, 1H), 7.24 (s, 2H), 6.67 (s, 2H), 6.51 (s, 2H), 5.78 (d, J=8.8 Hz, 2H), 5.03 (dd, J=34.2, 12.8 Hz, 4H), 3.93 (s, 6H), 3.68 (td, J=9.8, 3.7 Hz, 2H), 2.89 (dd, J=16.9, 10.3 Hz, 2H), 2.34 (d, J=17.0 Hz, 2H), 1.75 (s, 6H), 1.22 (d, J=8.5 Hz, 16H), 0.84 (s, 18H), 0.22 (s, 6H), 0.16 (s, 6H).

(ii) (11S,11aS,11'S,11a'S)-di-tert-butyl 8,8'-(((5-(2,2-dimethyl-4,20-dioxo-3,8,11,14,17-pentaoxa-5,21-diazatetracos-23-yn-24-yl)-1,3-phenylene)bis(methylene))bis(oxy))bis(11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate) (24)

A catalytic amount of $Pd(PPh_3)_4$(22.8 mg, 19.9 μmol, 0.02 eq) was added to a mixture of 23 (1.2 g, 0.995 mmol, 1 eq), 13 (400 mg, 0.995 mmol, 1 eq), CuI (7.6 mg, 39.6 μmol, 0.04 eq), diethylamine (0.20 mL, 1.99 mmol, 2 eq) and oven-dried 4 Å molecular sieve pellets in dry DMF (1 mL). The mixture was degased and flushed with argon 3 times then heated in a microwave at 100° C. for 10 minutes. DMF was removed by rotary evaporation under reduced pressure. The reaction mixture was diluted in ethyl acetate and washed with water and brine. The organic layer was dried over magnesium sulphate filtered and excess ethyl acetate was removed by rotary evaporation under reduced pressure. The resulting residue was subjected to flash column chromatography (silica gel; 5% methanol in dichloromethane). Pure fractions were collected and combined and excess eluent was removed by rotary evaporation under reduced pressure to give the product 24 (1.17 g. 79%). LC/MS, Method D, (2.43 min (ES+) m/z (relative intensity) no ionisation; $^1$H NMR (400 MHz, $CDCl_3$) δ 7.49 (s, 1H), 7.47 (s, 2H), 7.24 (s, 2H), 6.68 (s, 2H), 6.56 (s, 2H), 5.79 (d, J=8.9 Hz, 2H), 5.04 (dd, J=28.9, 12.3 Hz, 4H), 4.25 (d, J=5.4 Hz, 2H), 3.93 (s, 6H), 3.79-3.56 (m, 16H), 3.52 (t, J=5.2 Hz, 2H), 3.29 (d, J=5.0 Hz, 2H), 2.97-2.83 (m, 2H), 2.51 (t, J=5.7 Hz, 2H), 2.35 (d, J=16.1 Hz, 2H), 1.76 (s, 6H), 1.43 (s, 9H), 1.22 (s, 18H), 0.85 (s, 18H), 0.22 (s, 6H), 0.17 (s, 6H).

(iii) (11S,11aS,11'S,11a'S)-di-tert-butyl 8,8'-(((5-(1-amino-15-oxo-3,6,9,12-tetraoxa-16-azanonadec-18-yn-19-yl)-1,3-phenylene)bis(methylene))bis(oxy))bis(11-hydroxy-7-methoxy-2-methyl-5-oxo-11,11a-dihydro-1H-benzo[e]pyrrolo[1,2-a][1,4]diazepine-10(5H)-carboxylate) (25)

Tert-butyldimethylsilyltriflate (0.77 mL, 3.37 mmol, 10 eq) was added to a solution of compound 24 (500 g, 0.337 mmol) and 2,6-lutidine (0.51 mL, 4.38 mmol, 12 eq) in dry dichloromethane (10 mL). The reaction was stirred for 12 hours at ambient temperature. The reaction mixture was washed with saturated aqueous ammonium chloride and brine. The organic phase was dried over magnesium sulphate, filtered and excess solvent was removed by rotary evaporation under reduced pressure to give the TBS carbamate intermediate. The residue was dissolved in tetrahydrofuran (10 mL) and a mixture of tetra-n-butylammonium fluoride (1M, 1.7 mL, 1.685 mmol, 5 eq) and acetic acid (0.1 mL, 1.685 mmol, 5 eq) was added. The reaction mixture was stirred 3 hours at room temperature; then washed with water, saturated aqueous sodium bicarbonate and brine. The organic phase was dried over magnesium sulphate, filtered and excess solvent was removed by rotary evaporation under reduced pressure to give 25 as crude. LC/MS, Method D, (1.27 min (ES+) m/z (relative intensity) 1155.30. ([M+H]$^+$)).

(d) N-(3-(3,5-bis(((S)-7-methoxy-2-methy-5-oxo-5,11a-dihydro-1H-benzo[e]pyrrolo[1,2-a][1,4]diazepin-8-yl)oxy)methyl)phenyl)prop-2-yn-1-yl)-1-(3-(2,5-dioxo-2,5-dihydro-1H-pyrrol-1-yl)propanamido)-3,6,9,12-tetraoxapentadecan-5-amide 27 [SG3376]
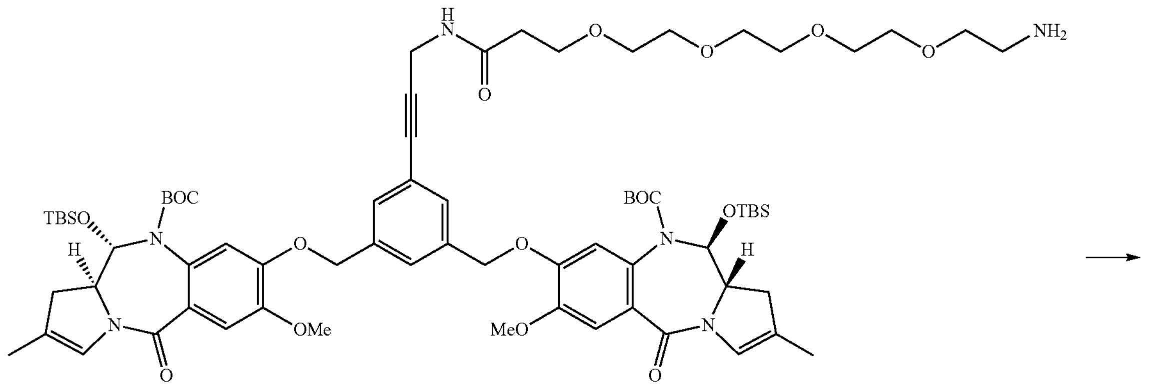
25
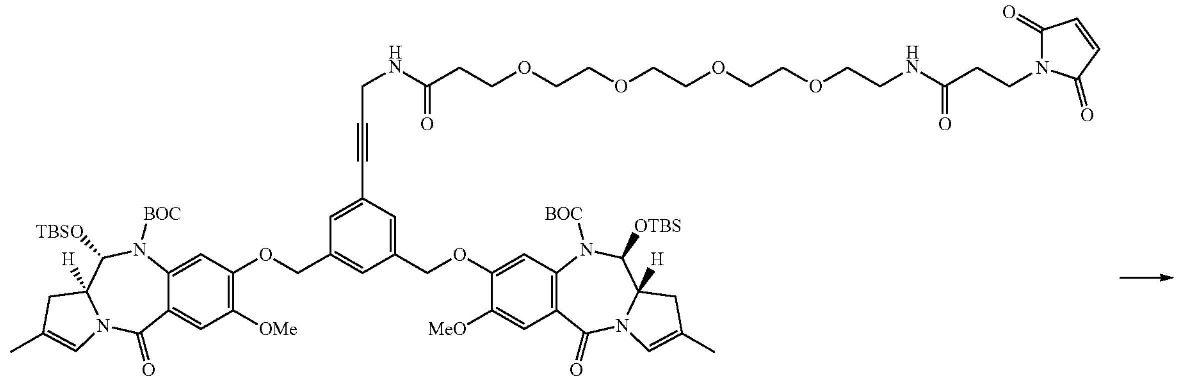
26
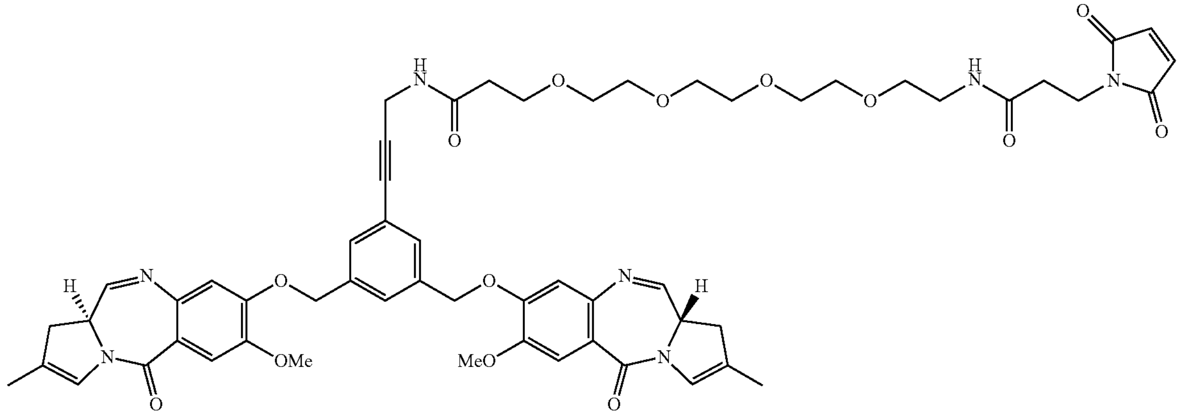
27

(i) (11S,11aS,11'S,11a'S)-di-tert-buty 8,8'-(((5-(1-(2,5-dioxo-2,5-dihydro-1H-pyrrol-1-yl-3,19-dioxo-7,10,13,16-tetraoxa-4,20-diazatricos-22-yn-23-yl)-1,3-phenylene)bis(methylene))bis(oxy))bis(11-hydroxy-7-methoxy-2-methy-5-oxo-11,11a-dihydro-1H-benzo[e]pyrrolo[1,2-a][1,4]diazepine-10(5H)-carboxylate) 26

EDCI (65 mg, 0.34 mmol, 1 eq) was added to a solution of crude 25 (0.34 mmol, 1 eq) and 3-maleimidopropionic acid (57.5 mg, 0.34 mmol, 1 eq) in dichloromethane (10 mL). The reaction was stirred at room temperature for 12 hours after which full conversion was observed by LCMS. The reaction mixture was diluted in dichloromethane and washed with water and brine. The organic layer was dried over magnesium sulphate filtered and excess dichloromethane was removed by rotary evaporation under reduced pressure to give compound 26 as crude. LC/MS, Method D, (1.49 min (ES+) r/z (relative intensity) no ionisation).

(ii) N-(3-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)prop-2-yn-1-yl)-1-(3-(2,5-dioxo-2,5-dihydro-1H-pyrrol-1-yl)propanamido)-3,6,9,12-tetraoxapentadecan-15-amide 27

Trifluoroacetic acid (9.5 mL) was added to a mixture of crude 26 (0.337 mmol) in water (0.5 mL) at 0° C. The reaction was stirred 2 hours at 0° C. Then the reaction mixture was added dropwise in cold saturated aqueous sodium bicarbonate. The reaction mixture was extracted with dichloromethane. The organic layer was then washed with brine, dried over magnesium sulphate filtered and excess dichloromethane was removed by rotary evaporation under reduced pressure. The resulting residue was subjected to flash column chromatography (silica gel; gradient; 2 to 5% methanol in dichloromethane). Pure fractions were collected and combined and excess eluent was removed by rotary evaporation under reduced pressure to give the product 27 (70.4 mg, 20%). LC/MS, Method E, (4.96 min (ES+) m/z (relative intensity) 1070.25. ([M+H]$^+$); $^1$H NMR (400 MHz, $CDCl_3$) δ 7.78 (d, J=4.0 Hz, 2H), 7.52 (s, 2H), 7.44 (s, 2H), 7.40 (s, 1H), 7.02-6.93 (m, 1H), 6.88 (s, 1H), 6.77 (s, 2H), 6.74 (s, 2H), 6.65 (s, 2H), 5.22-5.01 (m, 4H), 4.31-4.15 (m, 4H), 3.94 (s, 6H), 3.89-3.72 (nm, 4H), 3.65-3.54 (m, 10H), 3.54-3.45 (m, 4H), 3.43-3.34 (m, 2H), 3.25-3.12 (m, 2H), 2.94 (dd, J=27.0, 10.2 Hz, 2H), 2.51 (dd, J=13.6, 6.7 Hz, 4H), 1.83 (s, 6H).

(e) N-(3-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)prop-2-yn-1-yl)-1-(2-iodoacetamido)-3,6,9,12-tetraoxapentadecan-15-amide 29 [SG3378]

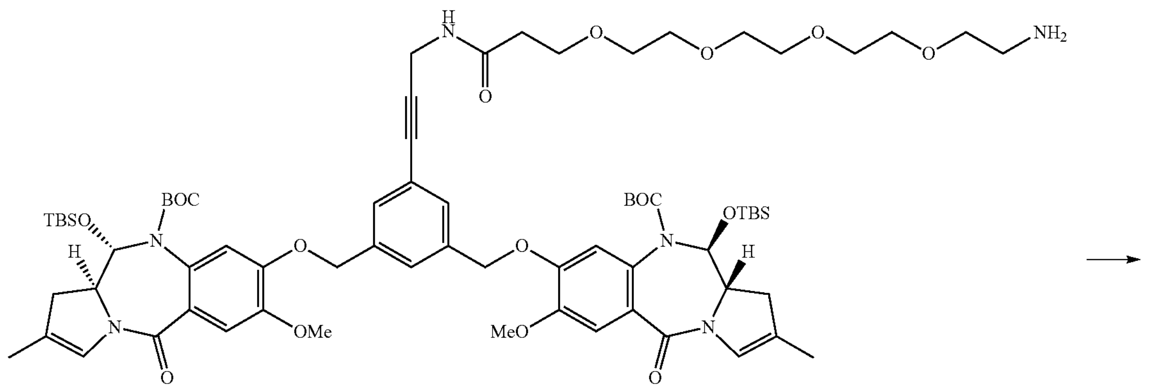

25

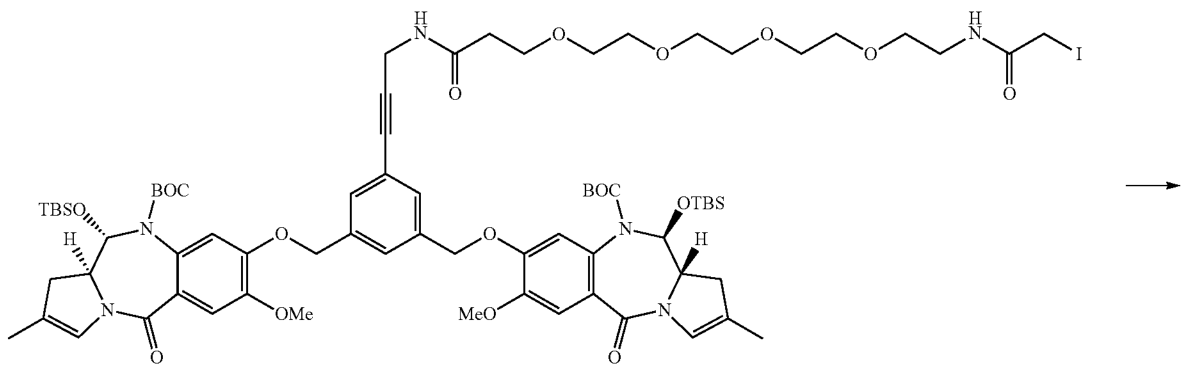

28

-continued

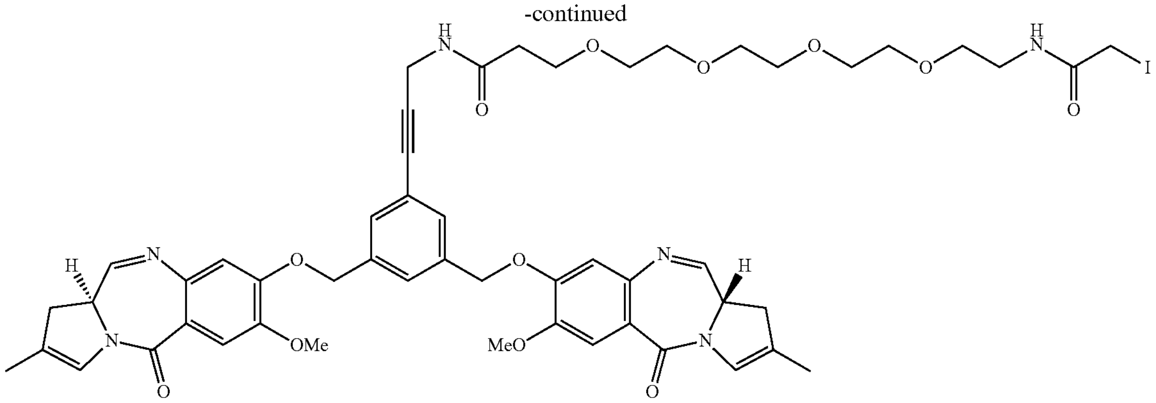

29

(i) (11S,11aS,11'S,11a'S)-di-tert-buty 8,8'-(((5-(1-iodo-2,18-dioxo-6,9,12,15-tetraoxa-3,19-diazadocos-21-yn-22-yl)-1,3-phenylene)bis(methylene))bis(oxy))bis(11-hydroxy-7-methoxy-2-methyl-5-oxo-11,11a-dihydro-1H-benzo[e]pyrrolo[1,2-a][1,4]diazepine-10(5H)-carboxylate) 28

Iodoacetic anhydride (53 mg, 0.150 mmol, 1 eq) was added to a solution of crude 25 (0.150 mmol, 1 eq) in dichloromethane (5 mL). The reaction was stirred at room temperature for 20 minutes after which full conversion was observed by LCMS. The reaction mixture was diluted in dichloromethane and washed with water. The organic layer was dried over magnesium sulphate filtered and excess dichloromethane was removed by rotary evaporation under reduced pressure to give compound 28 as crude. LC/MS, Method D, (1.50 min (ES+) m/z (relative intensity) no ionisation).

(ii) N-(3-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)prop-2-yn-1-yl)-1-(2-iodoacetamido)-3,6,9,12-tetraoxapentadecan-15-amide 29

Trifluoroacetic acid (0.45 mL) was added to a mixture of crude 28 (0.337 mmol) in water (0.05 mL) at 0° C. The reaction was stirred 30 minutes at 0° C. Then the reaction mixture was added dropwise in cold saturated aqueous sodium bicarbonate. The reaction mixture was extracted with dichloromethane. The organic layer was then washed with brine, dried over magnesium sulphate filtered and excess dichloromethane was removed by rotary evaporation under reduced pressure. The resulting residue was subjected to flash column chromatography (silica gel; gradient; 2 to 5% methanol in dichloromethane). Pure fractions were collected and combined and excess eluent was removed by rotary evaporation under reduced pressure to give the product 29 (4.23 mg, 5%). LC/MS, Method D, (1.35 min (ES+) m/z (relative intensity) 1087.20 ($[M+H]^+$); $^1$H NMR (400 MHz, $CDCl_3$) δ 7.79 (d, J=4.0 Hz, 2H), 7.53 (s, 2H), 7.45 (s, 3H), 7.07 (br, 1H), 6.94 (br, 1H), 6.78 (s, 2H), 6.73 (s, 2H), 5.15 (q, J=12.6 Hz, 4H), 4.32-4.19 (m, 4H), 3.96 (s, 6H), 3.76 (dd, J=12.0, 6.4 Hz, 2H), 3.69 (s, 2H), 3.64 (d, J=3.6 Hz, 8H), 3.60 (s, 4H), 3.55-3.49 (m, 2H), 3.42 (dd, J=10.3, 5.2 Hz, 2H), 3.23-3.11 (m, 2H), 3.00-2.89 (m, 2H), 2.53 (t, J=5.7 Hz, 2H), 1.83 (s, 6H).

Example 5

(a) (11S,11aS,11'S,11a'S)-di-tert-butyl 8,8'(((5-(1-(20-amino-3,6,9,12,15,18-hexaoxaicosyl)-1H-1,2,3-triazol-4-yl)-1,3-phenylene)bis(methylene))bis(oxy))bis(11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate) 32

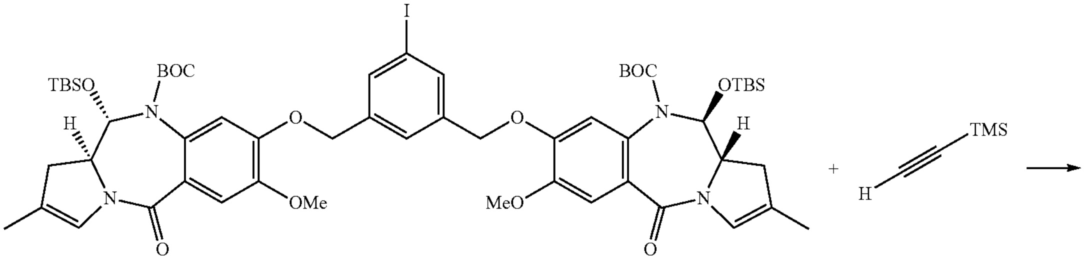

23

-continued

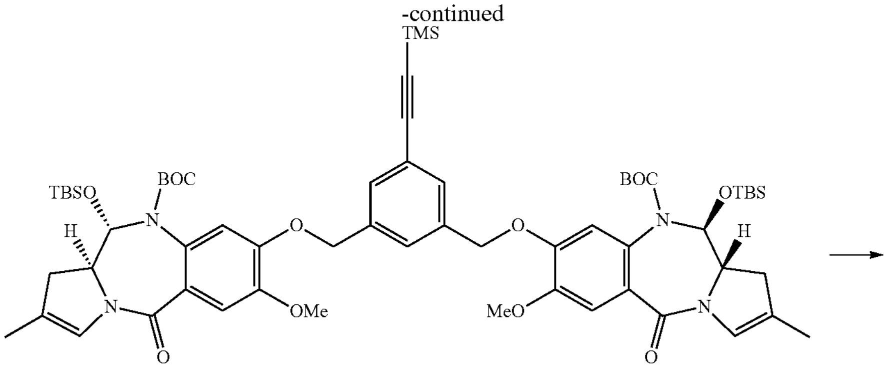

30

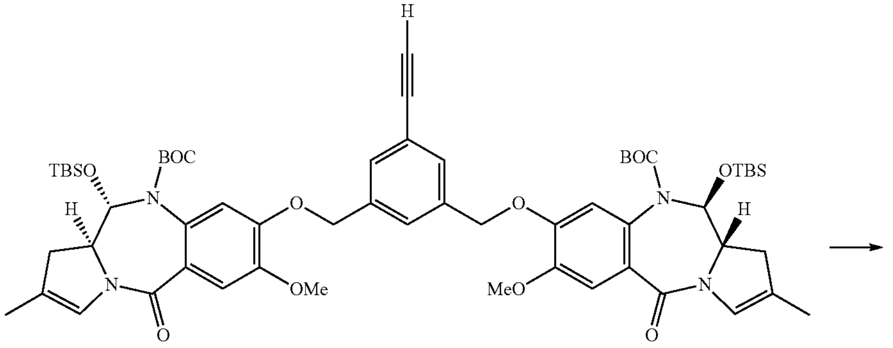

31

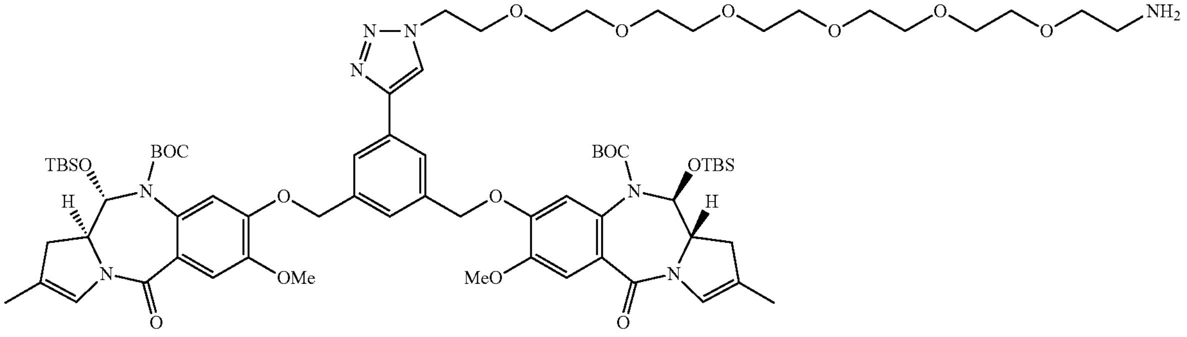

32

(i) (11S,11aS,11'S,11a'S)-di-tert-butyl 8,8'-(((5-((trimethylsilyl)ethynyl)-1,3-phenylene)bis(methylene))bis(oxy))bis(11-((tert-butylmethylsilyl)oxy)-7-methoxy-2-methyl-5-oxo-11,11a-dihydro-1H-benzo[e]pyrrolo[1,2-a][1,4]diazepine-10(5H)-carboxylate) 30

A catalytic amount of $Pd(PPh_3)_4$ (11 mg, 0.01 mmol, 0.002 eq) was added to a mixture of 23 (600 mg, 0.496 mmol), TMS-acetylene (0.21 mL, 1.488 mmol, 3 eq), CuI (4.0 mg, 0.02 mmol, 0.04 eq), diethylamine (0.1 mL, 0.992 mmol, 2 eq) and oven-dried 4 Å molecular sieve heated in a microwave at 100° C. for 10 minutes. DMF was removed by rotary evaporation under reduced pressure. The reaction mixture was diluted in ethyl acetate and washed with water and brine. The organic layer was dried over magnesium sulphate filtered and excess ethyl acetate was removed by rotary evaporation under reduced pressure. The resulting residue was subjected to flash column chromatography (silica gel: 50% ethyl acetate in hexane). Pure fractions were collected and combined and excess eluent was removed by rotary evaporation under reduced pressure to give the product 30 (530 mg, 91%). LC/MS, Method C, (2.45 min (ES+); no ionisation); $^1H$ NMR (400 MHz, $CDCl_3$) δ 7.52 (s, 1H), 7.49 (s, 2H), 7.23 (s, 2H), 6.67 (s, 2H), 6.54 (s, 2H), 5.78 (d, J=8.8 Hz, 2H), 5.06 (dd, J=41.6, 12.8 Hz, 4H), 3.93 (s, 6H), 3.68 (td, J=9.8, 3.7 Hz, 2H), 2.90 (dd, J=17.0, 10.4 Hz, 2H), 2.35 (d, J=17.0 Hz, 2H), 1.76 (s, 6H), 1.20 (s, 18H), 0.84 (s, 18H), 0.22 (s, 15H), 0.17 (s, 6H).

(ii) (11S,11aS,11'S,11a'S)-di-tert-butyl 8,8'-(((5-ethynyl-1,3-phenylene)bis)(methylene))bis(oxy))bis(11-((tert-butyldimethylsily)oxy)-7-methoxy-2-methyl-5-oxo-11,11a-dihydro-1H-benzo[e]pyrrolo[1,2-a][1,4]diazepine-10(5H)-carboxylate) 31

Solid $K_2CO_3$ (124 mg, 0.90 mmol, 2 eq) was added to a stirred solution of the TMS-protected compound 30 (530 mg, 0.449 mmol) in MeOH (10 mL). After 1 hour stirring at room temperature the reaction was complete. Methanol was removed by rotary evaporation under reduced pressure. The reaction mixture was diluted in dichloromethane and washed with water and brine. The organic layer was dried over magnesium sulphate filtered and excess dichloromethane was removed by rotary evaporation under reduced pressure to give the product 31 (477 mg, 95%). LC/MS, Method C, (2.32 min (ES+); no ionisation); $^1$H NMR (400 MHz, $CDCl_3$) δ 7.53 (s, 3H), 7.24 (s, 2H), 6.68 (s, 2H), 6.54 (s, 2H), 5.79 (d, J=8.7 Hz, 2H), 5.07 (dd, J=33.2, 12.8 Hz, 4H), 3.93 (s, 6H), 3.69 (td, J=9.7, 3.6 Hz, 2H), 3.08 (s, 1H), 2.90 (dd, J=16.9, 10.3 Hz, 2H), 2.35 (d, J=16.8 Hz, 2H), 1.76 (s, 6H), 1.25-1.13 (m, 18H), 0.85 (s, 18H), 0.22 (s, 6H), 0.16 (m, 6H).

(iii) (11S,11aS,11'S,11a'S)-di-tert-buty 8,8'-(((5-(1-(20-amino-3,6,9,12,15,18-hexaoxaicosyl)-1H-1,2,3-triazol-4-yl)-1,3-phenylene)bis(methylene))bis(oxy)) bis(1-((tert-butyldimethylsilyl)oxy)-7-methoxy-2-methy-5-oxo-11,11a-dihydro-1H-benzo[e]pyrrolo[1,2-a][1,4]diazepine-10(5H)-carboxylate) 32

Solid $CuSO_4.5H_2O$ (5 mg, 0.021 mmol. 0.05 eq) and (+)-sodium L-ascorbate (17.0 mg, 0.086 mmol, 0.2 eq) were added to a stirred solution of 20-azido-3,6,9,12,15,18-hexaoxaicosan-1-amine (151 mg, 0.43 mmol, 1 eq) and the alkyne 31 (477 mg, 0.43 mmol 1 eq) in tert-BuOH (5 mL) and $H_2O$ (5 mL) at room temperature. The mixture was degased and flushed with argon. After stirring for 2 hours, the reaction was complete. The reaction mixture was diluted in ethyl acetate and washed with water and brine. The organic layer was dried over magnesium sulphate filtered and excess ethyl acetate was removed by rotary evaporation under reduced pressure to give the product 32 (640 mg, quant). LC/MS, Method C, (1.67 min (ES+) m/z (relative intensity) 1457.35 ([M+H]+)); $^1$H NMR (400 MHz, $CDCl_3$) δ 8.10 (s, 1H), 7.93 (br, 3H), 7.54 (s, 1H), 7.25 (s, 2H), 6.68 (s, 2H), 6.62 (s, 2H), 5.79 (d, J=8.6 Hz, 2H), 5.14 (dd, J=30.6, 11.8 Hz, 4H), 4.68-4.59 (m, 2H), 4.00-3.94 (m, 2H), 3.94 (s, 6H), 3.75-3.47 (m, 24H), 2.91 (dd, J=16.9, 10.3 Hz, 2H), 2.35 (d, J=16.7 Hz, 2H), 1.76 (s, 6H), 1.31-1.11 (m, 18H), 0.85 (d, J=8.1 Hz, 18H), 0.20 (s, 6H), 0.16 (s, 6H).

(b) N-(20-(4-(3,5-bis((((S)-7-methoxy-2-methyl-5-oxo-5,11a-dihydro-1H-benzo[e]pyrrolo[1,2-a][1,4] diazepin-8-yl)oxy)methyl)phenyl)-1H-1,2,3-triazol-1-yl)-3,6,9,12,15,18-hexaoxaicosyl)-3-(2,5-dioxo-2,5-dihydro-1H-pyrrol-1-yl)propanamide (34) [SG3387]

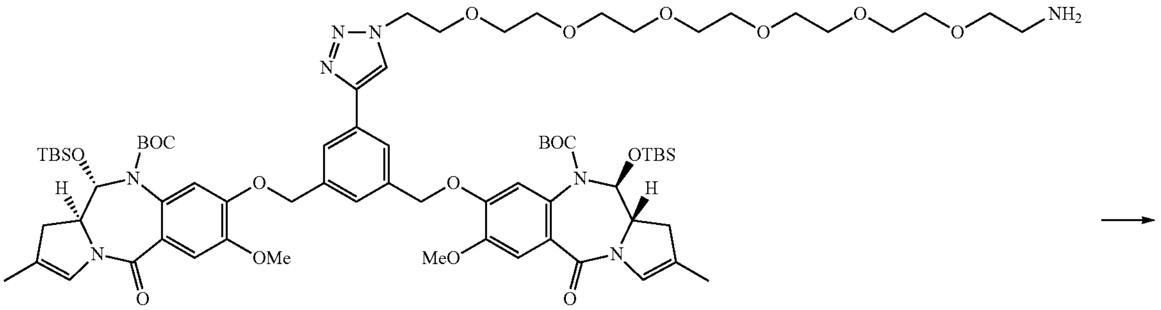

32

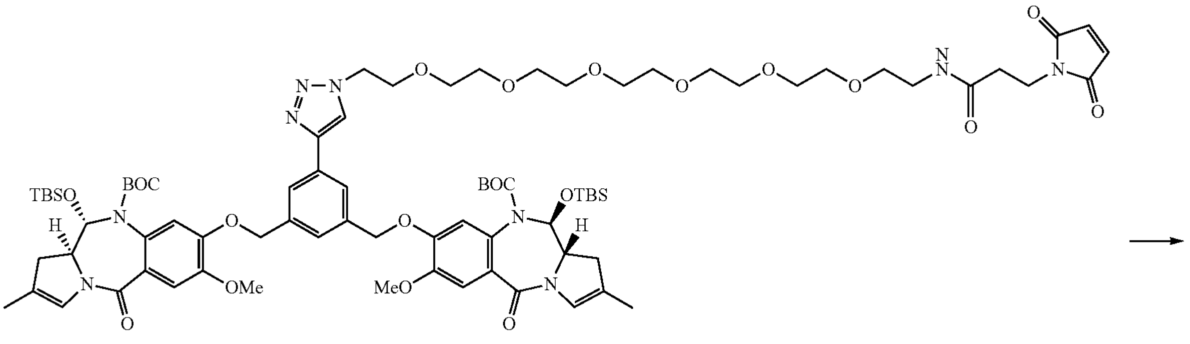

33

-continued

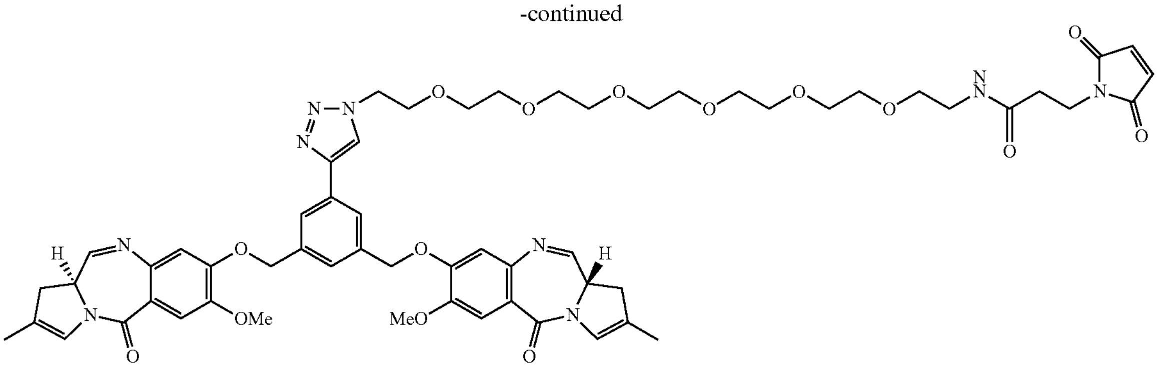

34

(i) (11S,11aS,11'S,11a'S)-di-tert-butyl 8,8'-(((5-(1-(24-(2,5-dioxo-2,5-dihydro-11H-pyrrol-1-yl)-22-oxo-3,6,9,12,15,18-hexaoxa-21-azatetracosyl)-1H-1,2,3-triazol-4-yl)-1,3-phenylene)bis(methylene))bis(oxy))bis(11-((ter-butyldimethylsily)oxy)-7-methoxy-2-methyl-5-oxo-11,11a-dihydro-11H-benzo[e]pyrrolo[1,2-a][1,4]diazepine-10(5H)-carboxylate) 33

EDCI (40 mg, 0.21 mmol, 1 eq) was added to a solution of 32 (300 mg, 0.206 mmol, 1 eq) and 3-maleimidopropionic acid (35 mg, 0.21 mmol, 1 eq) in dichloromethane (10 mL). The reaction was stirred at room temperature for 12 hours after which full conversion was observed by LCMS. The reaction mixture was diluted in dichloromethane and washed with water and brine. The organic layer was dried over magnesium sulphate filtered and excess dichloromethane was removed by rotary evaporation under reduced pressure to give compound 33 as crude (320 mg, quant), LC/MS, Method C, (2.13 min (ES+) m/z (relative intensity) 1609.55 ($[M+H]^+$).

(ii) N-(20-(4-(3,5-bis((((S)-7-methoxy-2-methyl-5-oxo-5,11a-dihydro-1H-benzo[e]pyrrolo[1,2-a][1,4]diazepin-8-yl)oxy)methy)phenyl)-1H-1,2,3-triazol-1-yl)-3,6,9,9,12,15,18-hexaoxaicosyl)-3-(2,5-dioxo-2,5-dihydro-1H-pyrrol-1-yl)propanamide 34

Trifluoroacetic acid (19 mL) was added to a mixture of crude 33 (0.186 mmol) in water (1 mL) at 0° C. The reaction was stirred 30 minutes at 0° C. Then the reaction mixture was added dropwise in cold saturated aqueous sodium bicarbonate (~2 L). The reaction mixture was extracted with dichloromethane (~1 L). The organic layer was then washed with brine, dried over magnesium sulphate, filtered and excess dichloromethane was removed by rotary evaporation under reduced pressure. The resulting residue was subjected to flash column chromatography (silica gel; gradient; 2 to 10% methanol in dichloromethane). Pure fractions were collected and combined and excess eluent was removed by rotary evaporation under reduced pressure to give the product 34 (56 mg, 26%). LC/MS, Method E, (4.99 min (ES+) m/z (relative intensity) 1144.35 ($[M+H]^+$); $^1H$ NMR (400 MHz, $CDCl_3$) δ 8.01 (s, 1H), 7.86 (s, 2H), 7.75 (d, J=3.9 Hz, 2H), 7.50 (s, 2H), 7.48 (s, 1H), 6.81 (s, 2H), 6.71 (s, 2H), 6.65 (s, 2H), 6.39 (br, 1H), 5.21 (q, J=12.4 Hz, 4H), 4.58 (t, J=4.8 Hz, 2H), 4.25-4.17 (m, 2H), 3.96-3.87 (m, 8H), 3.85-3.77 (m, 2H), 3.65-3.43 (m, 22H), 3.37 (dd, J=9.9, 4.8 Hz, 2H), 3.20-3.08 (m, 2H), 2.92 (dd, J=16.9, 4.6 Hz, 2H), 2.49 (t, J=7.2 Hz, 2H), 1.81 (s, 6H).

(c) N-(20-(4-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)-1H-1,2,3-triazol-1-yl)-3,6,9,12,15,18-hexaoxaicosyl)-2-iodoacetamide 36 [SG3389]

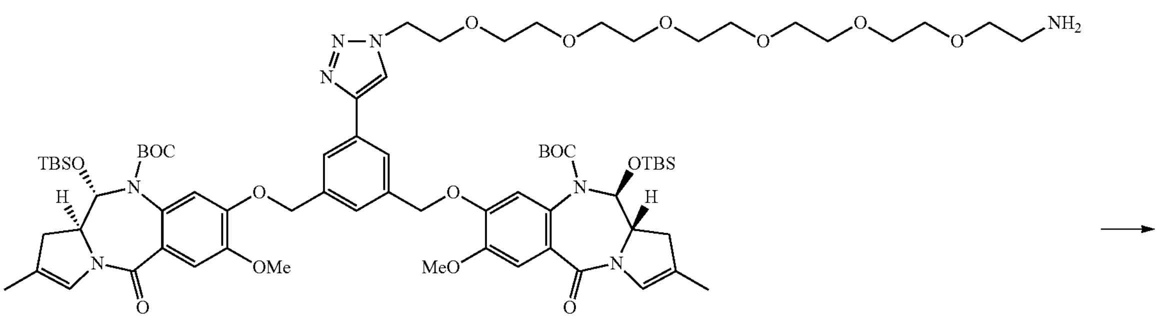

32

-continued

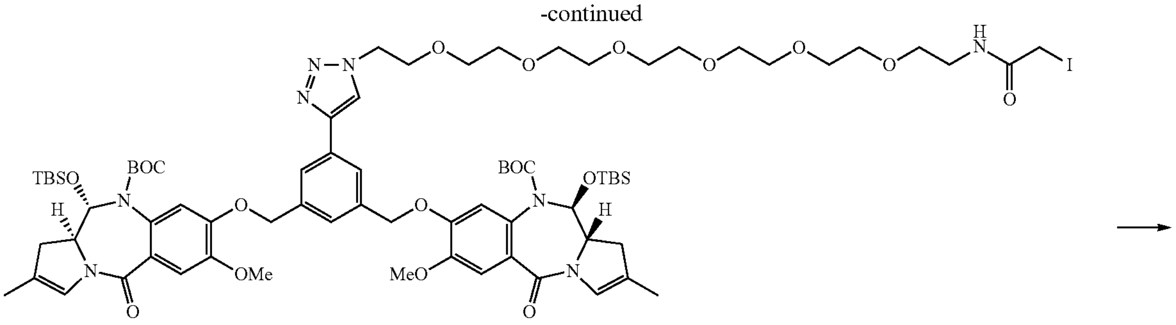

35

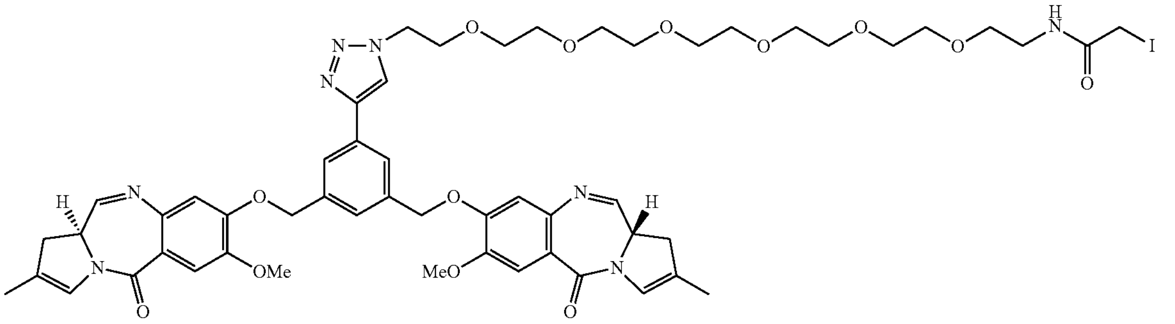

36

(i) (11S,11aS,11'S,11'S)-di-tert-butyl 8,8'-(((5-(1-(1-iodo-2-oxo-6,9,12,15,18,21-hexaoxa-3-azatricosan-23-yl)-1H-1,2,3-triazol-4-yl)-1,3-phenylene)bis(methylene))bis(oxy))bis(11-((tert-butyldimethylsily)oxy)-7-methoxy-2-methyl-5-oxo-11,11a-dihydro-1H-benzo[e]pyrrolo[1,2-a][1,4]diazepine-10(5H)-carboxylate)35

Iodoacetic anhydride (37 mg, 0.103 mmol, 1 eq) was added to a solution of 32 (150 mg, 0.103 mmol, 1 eq) in dichloromethane (5 mL). The reaction was stirred at room temperature for 20 minutes after which full conversion was observed by LCMS. The reaction mixture was diluted in dichloromethane and washed with water. The organic layer was dried over magnesium sulphate filtered and excess dichloromethane was removed by rotary evaporation under reduced pressure to give compound 35 as crude.

LC/MS, Method C, (2.17 min (ES+) m/z (relative intensity) 1625.35 ([M+H]$^+$).

(ii) N-(20-(4-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)-1H-1,2,3-triazol-1-yl)-3,6,9,12,15,18-hexaoxaicosyl)-2-iodoacetamide 36

Trifluoroacetic acid (4.95 mL) was added to a mixture of crude 35 (0.103 mmol) in water (0.05 mL) at 0° C. The reaction was stirred 30 minutes at 0° C. Then the reaction mixture was added dropwise in cold saturated aqueous sodium bicarbonate (200 mL). The reaction mixture was extracted with dichloromethane. The organic layer was then washed with brine, dried over magnesium sulphate, filtered and excess dichloromethane was removed by rotary evaporation under reduced pressure. The resulting residue was subjected to flash column chromatography (silica gel; gradient; 2 to 10% methanol in dichloromethane). Pure fractions were collected and combined and excess eluent was removed by rotary evaporation under reduced pressure to give the product 36 (32 mg, 27%). LC/MS, Method E, (5.16 min (ES+) m/z (relative intensity) 1161.10 ([M+H]$^+$); $^1$H NMR (400 MHz, CDCl) δ 8.03 (s, 1H), 7.87 (s, 2H), 7.76 (d, J=3.9 Hz, 2H), 7.51 (s. 2H), 7.48 (s, 1H), 6.95 (br, 1H), 6.82 (s, 2H), 6.72 (s, 2H), 5.21 (q, J=12.4 Hz, 4H), 4.59-4.58 (m, 2H), 4.24-4.20 (m, 2H), 3.96-3.87 (m, 8H), 3.70 (s, 2H), 3.66-3.47 (m, 22H), 3.41 (dd, J=10.3, 5.2 Hz, 2H), 3.19-3.07 (m, 2H), 2.98-2.85 (m, 2H), 1.78 (d, J=22.4 Hz, 6H).
Example 6
N-(20-(4-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)-1H-1,2,3-triazol-1-yl)-3,6,9,12,15,18-hexaoxaicosyl)pent-4-ynamide (38)
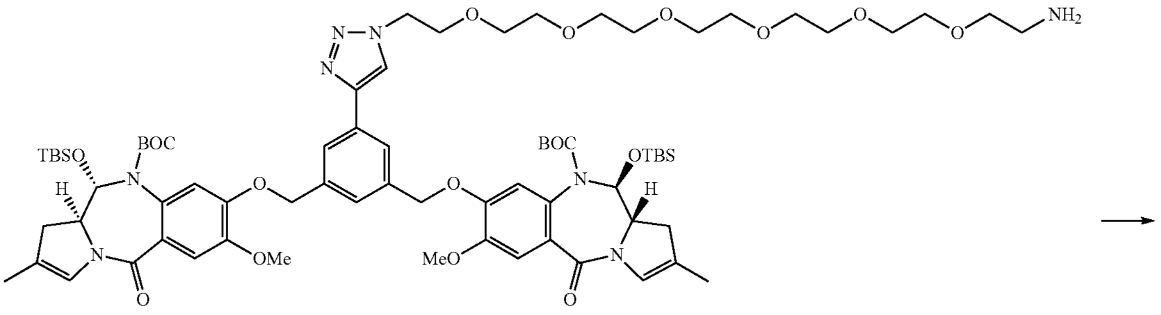
32
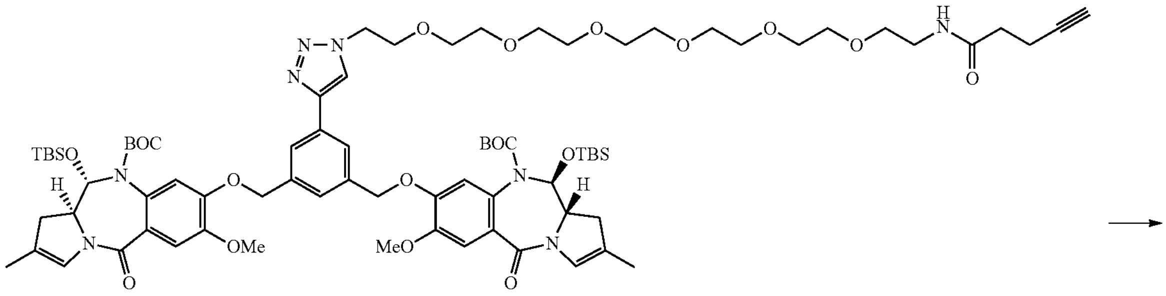
37
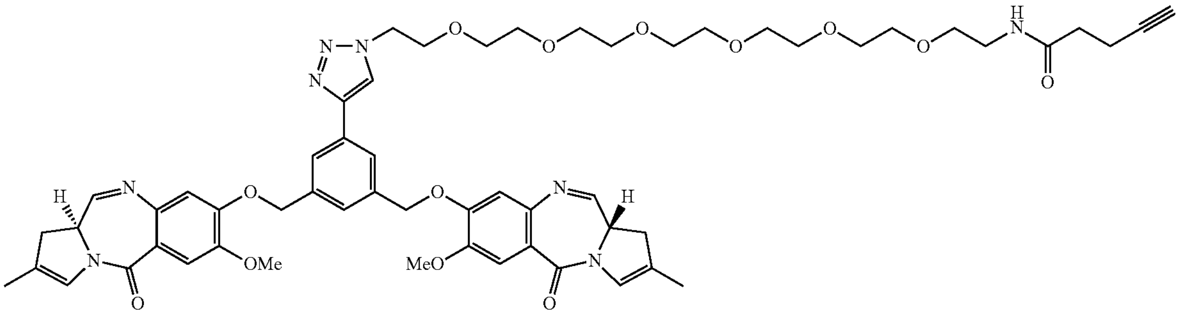
38

(i) (11S,11aS,11'S,11a'S)-di-tert-butyl 8,8'-(((5-(1-(22-oxo-3,6,9,12,15,18-hexaoxa-21-azahexacos-25-yn-1-yl)-1H-1,2,3-triazol-4-yl)-1,3-phenylene)bis(methylene))bis(oxy))bis(11-((tert-butyldimethylsilyl)oxy)-7-methoxy-2-methyl-5-oxo-11,11a-dihydro-1H-benzo[e]pyrrolo[1,2-a][1.4]diazepine-10(5H)-carboxylate) 37

EDCI (20 mg, 0.103 mmol, 1 eq) was added to a solution of 32 (150 mg, 0.103 mmol, 1 eq) and pent-4-ynoic acid (20 mg, 0.103 mmol, 1 eq) in dichloromethane (5 mL). The reaction was stirred at room temperature for 12 hours after which full conversion was observed by LCMS. The reaction mixture was diluted in dichloromethane and washed with water and brine. The organic layer was dried over magnesium sulphate filtered and excess dichloromethane was removed by rotary evaporation under reduced pressure to give compound 37 as crude. LC/MS, method C, (2.16 min (ES+) m/z (relative intensity) no ionisation).

(ii) N-(20-(4-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)-1H-1,2,3-triazol-1-yl)-3,6,9,12,15,18-hexaoxaicosyl)pent-4-ynamide 38

Trifluoroacetic acid (4.95 mL) was added to a mixture of crude 37 (0.103 mmol) in water (0.05 mL) at 0° C. The reaction was stirred 30 minutes at 0° C. Then the reaction mixture was added dropwise in cold saturated aqueous sodium bicarbonate (200 mL). The reaction mixture was extracted with dichloromethane. The organic layer was then washed with brine, dried over magnesium sulphate, filtered and excess dichloromethane was removed by rotary evaporation under reduced pressure. The resulting residue was subjected to flash column chromatography (silica gel; gradient; 2 to 10% methanol in dichloromethane). Pure fractions were collected and combined and excess eluent was removed by rotary evaporation under reduced pressure to give the product 38 (40 mg, 36%). LC/MS, method E, (5.11 min (ES+) m/z (relative intensity) 1073.30 ($[M+H]^+$); $^1H$ NMR (400 MHz, $CDCl_3$) δ 8.01 (s, 1H), 7.87 (s, 2H), 7.77 (d, J=3.8 Hz, 2H), 7.52 (s, 2H), 7.49 (s, 1H), 6.82 (s, 2H), 6.72 (s, 2H), 6.42 (s, 1H), 5.22 (q, J=12.3 Hz, 4H), 4.59 (t, J=4.8 Hz, 2H), 4.28-4.17 (m, 2H), 3.99-3.88 (m, 8H), 3.57 (dt, J=9.5, 8.0 Hz. 22H), 3.50-3.39 (m, 2H), 3.20-3.07 (m, 2H), 2.93 (dd, J=16.7, 3.9 Hz, 2H), 2.51 (t, J=6.1 Hz, 2H), 2.39 (t, J=7.2 Hz, 2H), 2.01 (dd, J=11.6, 5.4 Hz, 1H), 1.82 (s, 6H).

Example 7

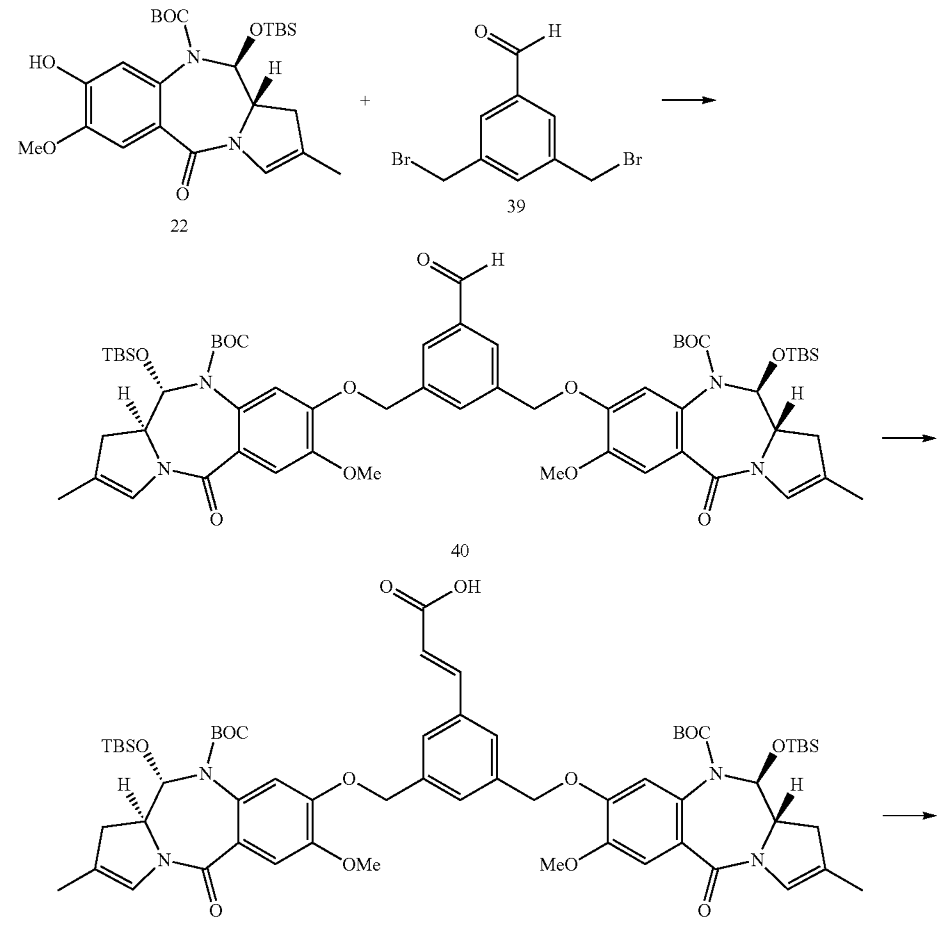

22

39

40

41

-continued
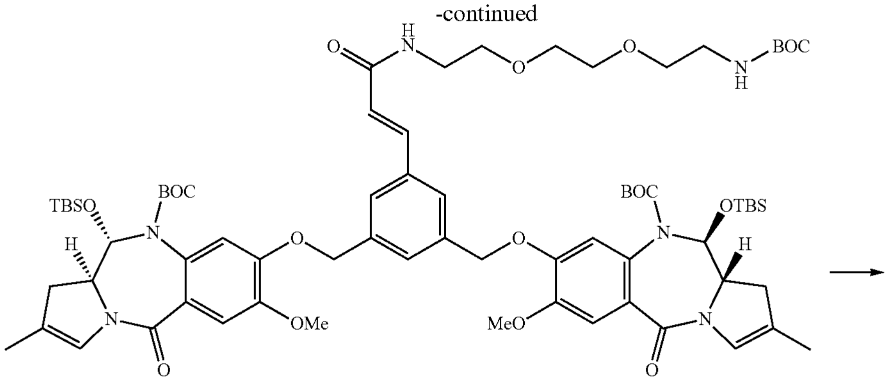
42
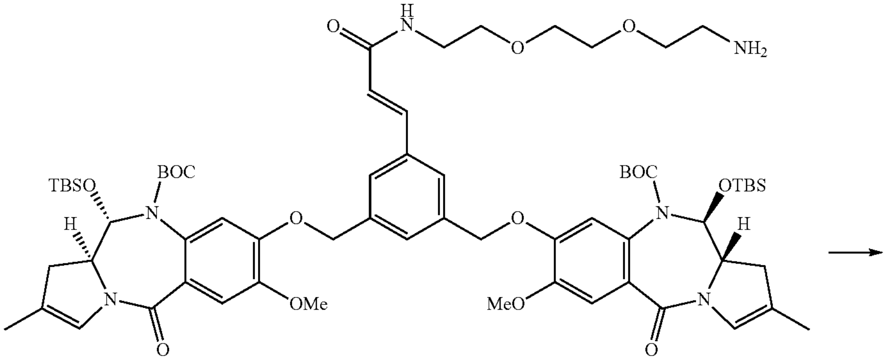
43
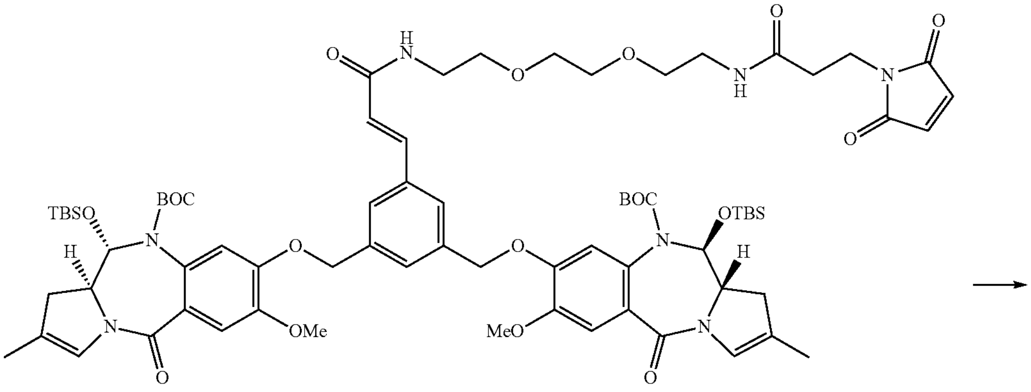
44
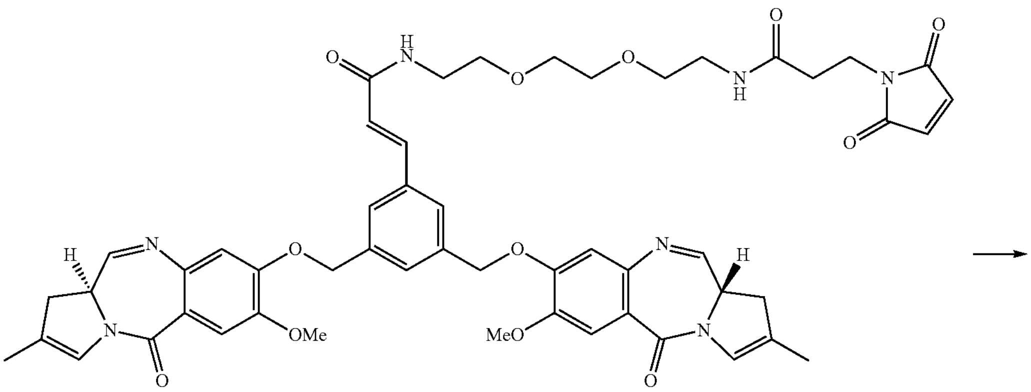
45

(i) di-tert-butyl 8,8'-(((5-formyl-1,3-phenylene)bis(methylene))bis(oxy))(11S,11aS,11'S,11a'S)-bis(11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate) 40

3,5-bis(bromomethyl)benzaldehyde 39 (30 mg, 0.102 mmol) was added to a stirred solution of 22 (100 mg, 0.204 mmol, 2 eq), TBAI (7 mg, 0.02 mmol, 0.1 eq) and $K_2CO_3$ (28 mg, 0.204 mmol, 2 eq) in dry DMF (2 mL). The reaction mixture was heated to 60° C. and stirred under an argon atmosphere for 4 hours and 12 hours at ambient temperature. The mixture was diluted in EtOAc and washed with water, brine. The organic layer was dried over magnesium sulphate, filtered and excess ethyl acetate was removed by rotary evaporation under reduced pressure. The resulting residue was subjected to flash column chromatography (silica gel; gradient, 50% to 70% ethyl acetate in hexane). Pure fractions were collected and combined and excess eluent was removed by rotary evaporation under reduced pressure to give the product 40 (90 mg, 79%). LC/MS, method C, (2.27 min (ES+) m/z (relative intensity) 1111.35. ($[M+H]^+$), $^1H$ NMR (400 MHz, $CDCl_3$) δ 10.05 (s, 1H), 7.95 (s, 2H), 7.86 (s, 1H), 7.26 (s, 2H), 6.69 (s, 2H), 6.58 (s, 2H), 5.80 (d, J=8.5 Hz, 2H), 5.17 (s, 4H), 3.94 (s, 6H), 3.72-3.68 (m, 2H), 2.91 (dd, J=16.7, 10.3 Hz, 2H), 2.36 (d, J=17.4 Hz, 2H), 1.77 (s, 6H), 1.25 (s, 18H), 0.84 (s, 18H), 0.22 (s, 6H), 0.15 (s, 6H).

(ii) (E)-3-(3,5-bis((((11S,11aS)-10-(tert-butoxycarbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)methyl)phenyl)acrylic acid 41

Malonic acid (14 mg, 0.138 mmol, 2.2 eq) and compound 40 were dissolved in a mixture of piperidine (1 μL) and pyridine (0.1 mL). The reaction mixture was heated to 95° C. and stirred under an argon atmosphere for 2 hours. The mixture was diluted in EtOAc and washed with water, brine. The organic layer was dried over magnesium sulphate, filtered and excess ethyl acetate was removed by rotary evaporation under reduced pressure. The resulting residue was subjected to flash column chromatography (silica gel: gradient. 50% to 100% ethyl acetate in hexane followed by 2% MeOH in EtOAc). Pure fractions were collected and combined and excess eluent was removed by rotary evaporation under reduced pressure to give the product 41 (50 mg, 53%). LC/MS, method C, (2.21 min (ES+) m/z (relative intensity) 1153.35. ($[M+H]^+$), $^1H$ NMR (400 MHz, $CDCl_3$) δ 7.73 (d, J=15.9 Hz, 1H), 7.58 (s, 2H), 7.55 (s, 1H), 7.26 (s, 2H), 6.68 (s, 2H), 6.54 (s, 2H), 6.46 (d, J=16.0 Hz, 1H), 5.77 (d, J=8.6 Hz, 2H), 5.11 (dd, J=27.4, 12.3 Hz, 4H), 3.94 (s, 6H), 3.68 (dd, J=8.9, 6.4 Hz, 2H), 2.89 (dd, J=16.8, 10.3 Hz, 2H), 2.34 (d, J=16.7 Hz, 2H), 1.75 (s, 6H), 1.29-1.09 (m, 18H), 0.82 (s, 18H), 0.21 (s, 6H), 0.13 (s, 6H).

(iii) di-tert-butyl 8,8'-(((5-((E)-2,2-dimethyl-4,15-dioxo-3,8,11-trioxa-5,14-diazaheptadeca-16-en-17-yl)-1,3-phenylene)bis(methylene))bis(oxy))(11S,11aS,11'S,11a'S)-bis(11-((tert-butyldimethylsilyl)oxy)-7-methoxy-2-methyl-5-oxo-11,11a-dihydro-1H-benzo[e]pyrrolo[1,2-a][1,4]diazepine-10 (5H)-carboxylate) 42

EDCI (9 mg, 0.045 mmol, 1 eq) was added to a solution of 41 (50 mg, 0.043 mmol, 1 eq) and tert-butyl (2-(2-(2-aminoethoxy)ethoxy)ethyl)carbamate (11 mg, 0.045 mmol, 1 eq) in dichloromethane (2 mL). The reaction was stirred at room temperature for 1 hour after which full conversion was observed by LCMS. The reaction mixture was diluted in dichloromethane and washed with water and brine. The organic layer was dried over magnesium sulphate filtered and excess dichloromethane was removed by rotary evaporation under reduced pressure to give compound 42 as crude. LC/MS, method C, (2.29 min (ES+) m/z (relative intensity) 1384.35($[M+H]^+$)).

(iv) di-tert-butyl 8,8'-(((5-((E)-3-((2-(2(2-(2-aminoethoxy)ethoxy)ethyl)amino)-3-oxoprop-1-en-1-yl)-1,3-phenylene)bis(methylene))bis(oxy))(11S,11aS,11'S,11a'S)-bis(11-((tert-butyldimethylsily)oxy)-7-methoxy-2-methyl-5-oxo-11,11a-dihydro-1H-benzo[e]pyrrolo[1,2-a][1,4]diazepine-10(5H)-carboxylate) 43

Tert-butyldimethylsilyltriflate (0.10 mL, 0.43 mmol, 10 eq) was added to a solution of compound 42 (0.043 mmol) and 2,6-lutidine (0.07 mL, 0.56 mmol, 13 eq) in dry dichloromethane (2 mL). The reaction was stirred for 2 hours at ambient temperature. The reaction mixture was washed with saturated aqueous ammonium chloride, water and brine. The organic phase was dried over magnesium sulphate, filtered and excess solvent was removed by rotary evaporation under reduced pressure to give a mixture of amine 43 and mono TBS-deprotected compound as crude. LC/MS, method C, (1.72 min (ES+) m/z (relative intensity) 1283.35 ($[M+H]^+$)).

(v) di-tert-butyl 8,8'-(((5-((E)-16-(2,5-dioxo-2,5-dihydro-1H-pyrrol-1-yl)-3,14-dioxo-7,10-dioxa-4,13-diazahexadec-1-en-1-yl)-1,3-phenylene)bis(methylene))bis(oxy)) (11S,11aS,11'S,11a'S)-bis(11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate) 44

EDCI (9 mg, 0.045 mmol, 1 eq) was added to a solution of 43 (0.043 mmol, 1 eq) and 3-maleimidopropionic acid (8 mg, 0.045 mmol, 1 eq) in dichloromethane (2 mL). The reaction was stirred at room temperature for 12 hours after which full conversion was observed by LCMS. The reaction mixture was diluted in dichloromethane and washed with water and brine. The organic layer was dried over magnesium sulphate filtered and excess dichloromethane was removed by rotary evaporation under reduced pressure to give compound 44 as crude, LC/MS, method C, (2.19 min (ES+) m/z (relative intensity) 1435.40($[M+H]^+$).

(vi) (E)-3-(3,5-bis((((S)-7-methoxy-2-methyl-5-oxo-5,11a-dihydro-1H-benzo[e]pyrrolo[1,2-a][1,4]diazepin-8-yl)oxy)methyl)phenyl)-N-(2-(22-(2-(3-(2,5-dioxo-2,5-dihydro-1H-pyrrol-1-yl)propanamido)ethoxy)ethoxy)ethyl)acrylamide 45

Trifluoroacetic acid (4.95 mL) was added to a mixture of crude 44 (0.043 mmol) in water (0.05 mL) at 0° C. The reaction was stirred 1 hour at 0° C. Then the reaction mixture was added dropwise in cold saturated aqueous sodium bicarbonate (100 mL). The reaction mixture was extracted with dichloromethane. The organic layer was then washed with brine, dried over magnesium sulphate, filtered and excess dichloromethane was removed by rotary evaporation under reduced pressure. The resulting residue was subjected to preparative HPLC. Pure fractions were collected and combined and excess eluent was removed by lyophilisation to give the product 45 (4.26 mg, 10%). LC/MS, method C, (1.35 min (ES+) r/z (relative intensity) 968.25 ([M+H]$^+$).

Example 8

General Antibody Conjugation Procedure

Antibodies are diluted to 1-5 mg/mL in a reduction buffer (examples: phosphate buffered saline PBS, histidine buffer, sodium borate buffer, TRIS buffer). A freshly prepared solution of TCEP (tris(2-carboxyethyl)phosphine hydrochloride) is added to selectively reduce cysteine disulfide bridges. The amount of TCEP is proportional to the target level of reduction, within 1 to 4 molar equivalents per antibody, generating 2 to 8 reactive thiols. After reduction for several hours at 37° C., the mixture is cooled down to room temperature and excess drug-linker (7, 10) added as a diluted DMSO solution (final DMSO content of up to 10% volume/volume of reaction mixture). The mixture was gently shaken at either 4° C. or room temperature for the appropriate time, generally 1-3 hours. Excess reactive thiols can be reacted with a 'thiol capping reagent' like N-ethyl maleimide (NEM) at the end of the conjugation. Antibody-drug conjugates are concentrated using centrifugal spin-filters with a molecular weight cut-off of 10 kDa or higher, then purified by tangential flow filtration (TFF) or Fast Protein Liquid Chromatography (FPLC). Corresponding antibody-drug conjugates can be determined by analysis by High-Performance Liquid Chromatography (HPLC) or Ultra-High-Performance Liquid Chromatography (UHPLC) to assess drug-per-antibody ratio (DAR) using reverse-phase chromatography (RP) or Hydrophobic-Interaction Chromatography (HIC), coupled with UV-Visible, Fluorescence or Mass-Spectrometer detection; aggregate level and monomer purity can be analysed by HPLC or UHPLC using size-exclusion chromatography coupled with UV-Visible, Fluorescence or Mass-Spectrometer detection. Final conjugate concentration is determined by a combination of spectroscopic (absorbance at 280, 214 and 330 nm) and biochemical assay (bicinchonic acid assay BCA; Smith, P. K., et al. (1985) *Anal. Biochem.* 150 (1): 76-85; using a known-concentration IgG antibody as reference). Antibody-drug conjugates are generally sterile filtered using 0.2 μm filters under aseptic conditions, and stored at +4° C., −20° C. or −80° C.

Examples of particular conjugations are described below.

Conjugate A (Ab-7, ConjA)

Antibody (Ab) (2.0 mg, 13.3 nanomoles) was diluted into 1.8 mL of a reduction buffer containing 10 mM sodium borate pH 8.4, 2.5 mM EDTA and a final antibody concentration of 1.11 mg/mL. A 10 mM solution of TCEP was added (2 molar equivalent/antibody, 26.6 nanomoles, 2.66 μL) and the reduction mixture was heated at 37° C. for 2.3 hours in a heating block. After cooling down to room temperature, compound 7 was added as a DMSO solution (3.5 molar equivalent/antibody, 46.7 nanomoles, in 0.2 mL DMSO). The solution was mixed for 1 hour at room temperature then the conjugation was quenched by addition of N-ethyl maleimide (1 micromole, 10 μL at 100 mM) followed 15 minutes later by N-acetyl cystein (1.5 micromoles, 15 μL at 100 mM), then injected into a AKTA™FPLC using a GE Healthcare XK16/70 column packed with Superdex 200 PG, eluting with 1.5 mL/min of sterile-filtered Phosphate-buffered saline (PBS). Fractions corresponding to ConjA monomer peak were pooled, concentrated using a 15 mL Amicon Ultracell 50 KDa MWCO spin filter, analysed and sterile-filtered. BCA assay gives a concentration of final ConjA at 1.25 mg/mL in 1.4 mL, obtained mass of ConjA is 1.75 mg (87% yield).

UHPLC analysis on a Shimadzu Prominence system using a Phenomenex Aeris 3.6u XB-C18 150×2.1 mm column eluting with a gradient of water and acetonitrile on a reduced sample of ConjA at 280 nm and 330 nm (Compound 7 specific) shows a mixture of light and heavy chains attached to several molecules of compound 7, consistent with a drug-per-antibody ratio (DAR) of 2.8 molecules of compound 7 per antibody.

UHPLC analysis on a Shimadzu Prominence system using a Waters Acquity UPLC BEH200 SEC 1.7 um 4.6×150 mm column eluting with sterile-filtered Phosphate-buffered saline (PBS) containing 5% isopropanol (v/v) on a sample of ConjA at 280 nm shows a monomer purity of over 99% with no impurity detected.

Conjugate B (Ab-10, ConjB)

Antibody (Ab) (2.0 mg, 13.3 nanomoles) was diluted into 1.8 mL of a reduction buffer containing 10 mM sodium borate pH 8.4, 2.5 mM EDTA and a final antibody concentration of 1.11 mg/mL. A 10 mM solution of TCEP was added (2 molar equivalent/antibody, 26.6 nanomoles. 2.66 μL) and the reduction mixture was heated at 37° C. for 1.5 hours in a heating block. After cooling down to room temperature, compound 10 was added as a DMSO solution (3.5 molar equivalent/antibody, 46.7 nanomoles, in 0.2 mL DMSO). The solution was mixed for 2 hour at room temperature, then the conjugation was quenched by addition of N-ethyl maleimide (1 micromole, 10 μL at 100 mM) followed 15 minutes later by N-acetyl cystein (1.5 micromoles, 15 μL at 100 mM), then injected into a AKTA™FPLC using a GE Healthcare XK16/70 column packed with Superdex 200 PG, eluting with 1.5 mL/min of sterile-filtered Phosphate-buffered saline (PBS). Fractions corresponding to ConjB monomer peak were pooled, concentrated using a 15 mL Amicon Ultracell 50 KDa MWCO spin filter, analysed and sterile-filtered. BCA assay gives a concentration of final ConjB at 0.99 mg/mL in 1.4 mL, obtained mass of ConjB is 1.39 mg (70% yield).

UHPLC analysis on a Shimadzu Prominence system using a Phenomenex Aeris 3.6u XB-C18 150×2.1 mm column eluting with a gradient of water and acetonitrile on a reduced sample of ConjB at 280 nm and 330 nm (Compound 10 specific) shows a mixture of light and heavy chains attached to several molecules of compound B, consistent with a drug-per-antibody ratio (DAR) of 3.8 molecules of compound 10 per antibody.

UHPLC analysis on a Shimadzu Prominence system using a Waters Acquity UPLC BEH200 SEC 1.7 μm 4.6×150 mm column eluting with sterile-filtered Phosphate-buffered saline (PBS) containing 5% isopropanol (v/v) on a sample of ConjB at 280 nm shows a monomer purity of over 99% with no impurity detected.

Conjugate C (Ab-27, ConjC)

Antibody (2.5 mg, 16.7 nanomoles) was diluted into 2.25 mL of a reduction buffer containing 10 mM sodium borate pH 8.4, 2.5 mM EDTA and a final antibody concentration of 1.11 mg/mL. A 10 mM solution of TCEP was added (1.65 molar equivalent/antibody, 27.5 nanomoles, 2.75 mL) and the reduction mixture was heated at +37° C. for 1.6 hours in an incubator. After cooling down to room temperature, compound 27 was added as a DMSO solution (7.5 molar equivalent/antibody, 125 nanomoles, in 0.25 mL DMSO). The solution was mixed for 1.3 hours at room temperature, then the conjugation was quenched by addition of N-acetyl cysteine (250 nanomoles, 25 mL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to ConjC monomer peak were pooled, concentrated using a 15 mL Amicon Ultracell 50 KDa MWCO spin filter, analysed and sterile-filtered.

UHPLC analysis on a Shimadzu Prominence system using a Phenomenex Aeris 3.6u XB-C18 150×2.1 mm column eluting with a gradient of water and acetonitrile on a reduced sample of ConjC at 280 nm and 330 nm (compound 27 specific) shows a mixture of light and heavy chains attached to several molecules of compound 27, consistent with a drug-per-antibody ratio (DAR) of 2.56 molecules of compound 27 per antibody.

UHPLC analysis on a Shimadzu Prominence system using a Tosoh Bioscience TSKgel G3000SWXL 5 μm 7.8×300 mm column (with a 7 μm 6.0×40 mm guard column) eluting with sterile-filtered SEC buffer containing 200 mM potassium phosphate pH 6.95, 250 mM potassium chloride and 10% isopropanol (v/v) on a sample of ConjC at 280 nm shows a monomer purity of over 99% with no impurity detected. UHPLC SEC analysis gives a concentration of final ConjC at 0.77 mg/mL in 2.5 mL, obtained mass of ConjC is 1.93 mg (77% yield).

Conjugate D (Ab-29, ConjD)

Antibody (3.5 mg, 23.3 nanomoles) was diluted into 3.15 mL of a reduction buffer containing 10 mM sodium borate pH 8.4, 2.5 mM EDTA and a final antibody concentration of 1.11 mg/mL. A 10 mM solution of TCEP was added (2.0 molar equivalent/antibody, 46.7 nanomoles, 4.67 mL) and the reduction mixture was heated at +37° C. for 1.6 hours in an incubator. After cooling down to room temperature, compound 29 was added as a DMSO solution (10 molar equivalent/antibody, 233 nanomoles, in 0.175 mL DMSO). The solution was mixed for 3.9 hours at room temperature, at which point more compound 29 was added as a DMSO solution (10 molar equivalent/antibody, 233 nanomoles, in 0.175 mL DMSO), and the solution was mixed for a further 19 hours at room temperature. The conjugation was quenched by addition of N-acetyl cysteine (933 nanomoles, 93.3 mL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to ConjD monomer peak were pooled, concentrated using a 15 mL Amicon Ultracell 50 KDa MWCO spin filter, analysed and sterile-filtered.

UHPLC analysis on a Shimadzu Prominence system using a Phenomenex Aeris 3.6u XB-C18 150×2.1 mm column eluting with a gradient of water and acetonitrile on a reduced sample of ConjD at 280 nm and 330 nm (Compound 29 specific) shows a mixture of light and heavy chains attached to several molecules of compound 29, consistent with a drug-per-antibody ratio (DAR) of 2.43 molecules of compound 29 per antibody.

UHPLC analysis on a Shimadzu Prominence system using a Tosoh Bioscience TSKgel G3000SWXL 5 μm 7.8×300 mm column (with a 7 μm 6.0×40 mm guard column) eluting with sterile-filtered SEC buffer containing 200 mM potassium phosphate pH 6.95, 250 mM potassium chloride and 10% isopropanol (v/v) on a sample of ConjB at 280 nm shows a monomer purity of over 99% with no impurity detected. UHPLC SEC analysis gives a concentration of final ConjB at 0.73 mg/mL in 3.3 mL, obtained mass of ConjB is 2.42 mg (69% yield).

Conjugate E (Ab-34, ConjE)

Antibody (2.5 mg, 16.7 nanomoles) was diluted into 2.25 mL of a reduction buffer containing 10 mM sodium borate pH 8.4, 2.5 mM EDTA and a final antibody concentration of 1.11 mg/mL. A 10 mM solution of TCEP was added (1.65 molar equivalent/antibody, 27.5 nanomoles, 2.75 mL) and the reduction mixture was heated at +37° C. for 1.6 hours in an incubator. After cooling down to room temperature, compound 34 was added as a DMSO solution (7.5 molar equivalent/antibody, 125 nanomoles, in 0.25 mL DMSO). The solution was mixed for 1.3 hours at room temperature, then the conjugation was quenched by addition of N-acetyl cysteine (250 nanomoles, 25 mL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to ConjE monomer peak were pooled, concentrated using a 15 mL Amicon Ultracell 50 KDa MWCO spin filter, analysed and sterile-filtered.

UHPLC analysis on a Shimadzu Prominence system using a Phenomenex Aeris 3.6u XB-C18 150×2.1 mm column eluting with a gradient of water and acetonitrile on a reduced sample of ConjCE at 280 nm and 330 nm (Compound 34 specific) shows a mixture of light and heavy chains attached to several molecules of compound 34, consistent with a drug-per-antibody ratio (DAR) of 2.45 molecules of compound 34 per antibody.

UHPLC analysis on a Shimadzu Prominence system using a Tosoh Bioscience TSKgel G3000SWXL 5 μm 7.8×300 mm column (with a 7 μm 6.0×40 mm guard column) eluting with sterile-filtered SEC buffer containing 200 mM potassium phosphate pH 6.95, 250 mM potassium chloride and 10% isopropanol (v/v) on a sample of ConjE at 280 nm shows a monomer purity of over 99% with no impurity detected. UHPLC SEC analysis gives a concentration of final ConjE at 1.05 mg/mL in 2.0 mL, obtained mass of ConjE is 2.09 mg (84% yield).

Conjugate F (Ab-36, ConjF)

Antibody (3.5 mg, 23.3 nanomoles) was diluted into 3.15 mL of a reduction buffer containing 10 mM sodium borate pH 8.4, 2.5 mM EDTA and a final antibody concentration of 1.11 mg/mL. A 10 mM solution of TCEP was added (2.0 molar equivalent/antibody, 46.7 nanomoles, 4.67 mL) and the reduction mixture was heated at +37° C. for 1.6 hours in an incubator. After cooling down to room temperature, compound 36 was added as a DMSO solution (10 molar equivalent/antibody, 233 nanomoles, in 0.175 mL DMSO). The solution was mixed for 3.9 hours at room temperature, at which point more compound 36 was added as a DMSO solution (10 molar equivalent/antibody, 233 nanomoles, in 0.175 mL DMSO), and the solution was mixed for a further 19 hours at room temperature. The conjugation was quenched by addition of N-acetyl cysteine (933 nanomoles, 93.3 mL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to ConjF monomer peak were pooled, concentrated using a 15 mL Amicon Ultracell 50 KDa MWCO spin filter, analysed and sterile-filtered.

UHPLC analysis on a Shimadzu Prominence system using a Phenomenex Aeris 3.6u XB-C18 150×2.1 mm column eluting with a gradient of water and acetonitrile on a reduced sample of ConjF at 280 nm and 330 nm (Compound 36 specific) shows a mixture of light and heavy chains attached to several molecules of compound 36, consistent with a drug-per-antibody ratio (DAR) of 2.57 molecules of compound 36 per antibody.

UHPLC analysis on a Shimadzu Prominence system using a Tosoh Bioscience TSKgel G3000SWXL 5 μm 7.8×300 mm column (with a 7 μm 6.0×40 mm guard column) eluting with sterile-filtered SEC buffer containing 200 mM potassium phosphate pH 6.95, 250 mM potassium chloride and 10% isopropanol (v/v) on a sample of ConjF at 280 nm shows a monomer purity of over 99% with no impurity detected. UHPLC SEC analysis gives a concentration of final ConjF at 0.75 mg/mL in 3.8 mL, obtained mass of ConjF is 2.84 mg (81% yield).

Conjugate G (Ab-45, ConjG)

Antibody (2.5 mg, 16.7 nanomoles) was diluted into 2.25 mL of a reduction buffer containing 10 mM sodium borate pH 8.4, 2.5 mM EDTA and a final antibody concentration of 1.11 mg/mL. A 10 mM solution of TCEP was added (1.65 molar equivalent/antibody, 27.5 nanomoles, 2.75 mL) and the reduction mixture was heated at +37° C. for 1.6 hours in an incubator. After cooling down to room temperature, compound 45 was added as a DMSO solution (7.5 molar equivalent/antibody, 125 nanomoles, in 0.25 mL DMSO). The solution was mixed for 1.3 hours at room temperature, then the conjugation was quenched by addition of N-acetyl cysteine (250 nanomoles, 25 mL at 10 mM), then injected into an AKTA™ Pure FPLC using a GE Healthcare HiLoad™ 26/600 column packed with Superdex 200 PG, eluting with 2.6 mL/min of sterile-filtered phosphate-buffered saline (PBS). Fractions corresponding to ConjG monomer peak were pooled, concentrated using a 15 mL Amicon Ultracell 50 KDa MWCO spin filter, analysed and sterile-filtered.

UHPLC analysis on a Shimadzu Prominence system using a Phenomenex Aeris 3.6u XB-C18 150×2.1 mm column eluting with a gradient of water and acetonitrile on a reduced sample of ConjG at 280 nm and 330 nm (Compound 45 specific) shows a mixture of light and heavy chains attached to several molecules of compound 45, consistent with a drug-per-antibody ratio (DAR) of 2.13 molecules of compound 45 per antibody.

UHPLC analysis on a Shimadzu Prominence system using a Tosoh Bioscience TSKgel G3000SWXL 5 μm 7.8×300 mm column (with a 7 μm 6.0×40 mm guard column) eluting with sterile-filtered SEC buffer containing 200 mM potassium phosphate pH 6.95, 250 mM potassium chloride and 10% isopropanol (v/v) on a sample of ConjG at 280 nm shows a monomer purity of over 99% with no impurity detected. UHPLC SEC analysis gives a concentration of final ConjG at 0.67 mg/mL in 2.9 mL, obtained mass of ConjG is 1.94 mg (78% yield).

The Antibody used in the above conjugations was HERCEPTIN.

Example 9

In Vivo ADC Efficacy Studies

CB.17 SCID mice, aged 8-12 weeks, may be injected with 1 $mm^3$ tumour fragments subcutaneously in the flank. When tumours reach an average size of 100-150 mg, treatment may be begun. Mice may be weighed twice a week. Tumour size may be measured twice a week. Animals may be monitored individually. The endpoint of the experiment is a tumour volume of 1000 $mm^3$ or 60 days, whichever comes first. Responders can be followed longer.

Groups of 10 xenografted mice can be injected i.v. with 0.2 ml of antibody drug conjugate (ADC), or naked antibody, in phosphate buffered saline (vehicle) or with 0.2 ml of vehicle alone. The concentration of ADC can be adjusted to give, for example, 0.3 or 1.0 mg ADC/kg body weight in a single dose. Three identical doses may be given to each mouse at intervals of, for example, 1 week.

Example 10

In Vitro ADC Efficacy Studies

Medium from subconfluent (about 80-90% confluency) SK-BR-3 cells in a T75 flask was aspirated and PBS (about 20 ml) was added to rinse away the culture medium. The PBS was aspirated and Trypsin-EDTA (5 ml) added. The flask was returned to the 37° C. gassed incubator for up to about 5 minutes. The flask was rapped sharply to dislodge and dissociate cells from the plastic. The cell suspension was transferred to a sterile 50 ml screw-top centrifuge tube. Medium (McCoy's+10% FCS) was added to a final volume of 15 ml, then the tube was centrifuged (400 g for 5 min). The supernatant was aspirated and the pellet re-suspended in 10 ml culture medium. Repeated aspiration (up and down a 10 ml pipette) may be necessary to break up cell clumps and produce monodisperse cell suspensions suitable for counting. Cell suspension (10 μl) was mixed with Trypan blue (10 μl) and live/dead cells counted with a haemocytometer to determine cell concentration and viability. The cell suspension was diluted to $20\times10^4$/ml and 50 μl was dispensed into clear 96 well flat bottomed plates. The cells were incubated overnight to allow recovery before use.

A stock solution (1 ml) of antibody drug conjugate (ADC) (20 μg/ml) was made by dilution of filter-sterilised ADC into cell culture medium. A set of 8×10-fold dilutions of stock ADC was made in a 24 well plate by serial transfer of 100 μl onto 900 μl of cell culture medium.

50 μl of each ADC dilution is dispensed into 4 replicate wells of the 96 well plate, containing 50 μl cell suspension seeded the previous day. Control wells receive 50 μl cell culture medium. The 96-well plate containing cells and ADCs was incubated at 37° C. in a $CO_2$-gassed incubator for 4 days. At the end of the incubation period, viable cells were measured by MTS assay. MTS (Promega) was dispensed (20 μl per well) into each well and incubated for 4 hours at 37° C. in the $CO_2$-gassed incubator. Well absorbance was measured at 490 nm. Percentage cell survival is calculated from the mean absorbance in the 4 ADC-treated wells compared to the mean absorbance in the 4 control wells (100%).

| ADC | $EC_{50}$ (μg/ml) |
|---|---|
| ConjD | 0.001696 |
| ConjE | 0.002766 |
| ConjF | 0.003576 |
| ConjG | 0.006163 |
| ConjC | 0.0006929 |

| Abbreviations | |
|---|---|
| Ac | acetyl |
| Acm | acetamidomethyl |
| Alloc | allyloxycarbonyl |
| Boc | di-tert-butyl dicarbonate |
| t-Bu | tert-butyl |

-continued

| Abbreviations | |
|---|---|
| Bzl | benzyl, where Bzl—OMe is methoxybenzyl and Bzl—Me is methylbenzene |
| Cbz or Z | benzyloxy-carbonyl, where Z—Cl and Z—Br are chloro- and bromobenzyloxy carbonyl respectively |
| DMF | N,N-dimethylformamide |
| Dnp | dinitrophenyl |
| DTT | dithiothreitol |
| Fmoc | 9H-fluoren-9-ylmethoxycarbonyl |
| imp | N-10 imine protecting group: 3-(2-methoxyethoxy)propanoate-Val-Ala-PAB |
| MC-OSu | maleimidocaproyl-O-N-succinimide |
| Moc | methoxycarbonyl |
| MP | maleimidopropanamide |
| Mtr | 4-methoxy-2,3,6-trimethtylbenzenesulfonyl |
| PAB | para-aminobenzyloxycarbonyl |
| PEG | ethyleneoxy |
| PNZ | p-nitrobenzyl carbamate |
| Psec | 2-(phenylsulfonyl)ethoxycarbonyl |
| TBDMS | tert-butyldimethylsilyl |
| TBDPS | tert-butyldiphenylsilyl |
| Teoc | 2-(trimethylsilyl)ethoxycarbonyl |
| Tos | tosyl |
| Troc | 2,2,2-trichlorethoxycarbanyl chloride |
| Trt | trityl |
| Xan | xanthyl |

REFERENCES

The following references are incorporated by reference in their entirety:

EP 0522868
EP 0875569
EP 1295944
EP 1347046
EP 1394274
EP 1394274
EP 1439393
JP 05003790
JP 2004113151
JP 58180487
US 2001/055751
US 2002/034749
US 2002/042366
US 2002/150573
US 2002/193567
US 2003/0228319
US 2003/060612
US 2003/064397
US 2003/065143
US 2003/091580
US 2003/096961
US 2003/105292
US 2003/109676
US 2003/118592
US 2003/119121
US 2003/119122
US 2003/119125
US 2003/119126
US 2003/119128
US 2003/119129
US 2003/119130
US 20031119131
US 2003/124140
US 2003/124579
US 20031129192
US 2003/134790-A1
US 20031143557
US 2003/157089
US 2003/165504
US 2003/185830
US 2003/186372
US 2003/186373
US 2003/194704
US 2003/206918
US 2003/219806
US 2003/224411
US 2003/224454
US 2003/232056
US 2003/232350
US 20030096743
US 20030130189
US 2003096743
US 2003130189
US 2004/0001827
US 2004/005320
US 2004/005538
US 2004/005563
US 2004/005598
US 2004/0101899
US 2004/018553
US 2004/022727
US 2004/044179
US 2004/044180
US 2004/101874
US 2004/197325
US 2004/249130
US 20040018194
US 20040052793
US 20040052793
US 20040121940
US 2005/271615
US 2006/116422
U.S. Pat. No. 4,816,567
U.S. Pat. No. 5,362,852
U.S. Pat. No. 5,440,021
U.S. Pat. No. 5,583,024
U.S. Pat. No. 5,621,002
U.S. Pat. No. 5,644,033
U.S. Pat. No. 5,674,713
U.S. Pat. No. 5,700,670
U.S. Pat. No. 5,773,223
U.S. Pat. No. 5,792,616
U.S. Pat. No. 5,854,399
U.S. Pat. No. 5,869,445
U.S. Pat. No. 5,976,551
U.S. Pat. No. 6,011,146
U.S. Pat. No. 6,153,408
U.S. Pat. No. 6,214,345
U.S. Pat. No. 6,218,519
U.S. Pat. No. 6,268,488
U.S. Pat. No. 6,518,404
U.S. Pat. No. 6,534,482
U.S. Pat. No. 6,555,339
U.S. Pat. No. 6,602,677
U.S. Pat. No. 6,677,435
U.S. Pat. No. 6,759,509
U.S. Pat. No. 6,835,807
U.S. Pat. No. 7,223,837
U.S. Pat. No. 7,375,078
U.S. Pat. No. 7,521,541
U.S. Pat. No. 7,723,485
WO 00/012508
WO 00/12507
WO 00/12508

WO 01/16318
WO 01/45746
WO 02/088172
WO 03/026577
WO 03/043583
WO 04/032828
WO 2000/12130
WO 2000/14228
WO 2000/20579
WO 2000/22129
WO 2000/32752
WO 2000/36107
WO 2000/40614
WO 2000/44899
WO 2000/55351
WO 2000/75655
WO 200053216
WO 2001/00244
WO 2001/38490
WO 2001/40269
WO 2001/40309
WO 2001/41787
WO 2001/46232
WO 2001/46261
WO 2001/48204
WO 2001/53463
WO 2001/57188
WO 2001/62794
WO 2001/66689
WO 2001/72830
WO 2001/72962
WO 2001/75177
WO 2001/77172
WO 2001/88133
WO 2001/90304
WO 2001/94641
WO 2001/98351
WO 2002/02587
WO 2002/02624
WO 2002/06317
WO 2002/06339
WO 2002/101075
WO 2002/10187
WO 2002/102235
WO 2002/10382
WO 2002/12341
WO 2002/13847
WO 2002/14503
WO 2002/16413
WO 2002/16429
WO 2002/22153
WO 2002/22636
WO 2002/22660
WO 2002/22808
WO 2002/24909
WO 2002/26822
WO 2002/30268
WO 2002/38766
WO 2002/54940
WO 2002/59377
WO 2002/60317
WO 2002/61087:
WO 2002/64798
WO 2002/71928
WO 2002/72596
WO 2002/78524
WO 2002/81646
WO 2002/83866
WO 2002/86443
WO 2002/88170
WO 2002/89747
WO 2002/92836
WO 2002/94852
WO 2002/98358
WO 2002/99074
WO 2002/99122
WO 2003/000842
WO 2003/002717
WO 2003/003906
WO 2003/003984
WO 2003/004989
WO 2003/008537
WO 2003/009814
WO 2003/014294
WO 2003/016475
WO 2003/016494
WO 2003/018621
WO 2003/022995
WO 2003/023013
WO 2003/024392
WO 2003/025138
WO 2003/025148
WO 2003/025228
WO 2003/026493
WO 2003/029262
WO 2003/029277
WO 2003/029421
WO 2003/034984
WO 2003/035846
WO 2003/042661
WO 2003/045422
WO 2003/048202
WO 2003/054152
WO 2003/055439
WO 2003/055443
WO 2003/062401
WO 2003/062401
WO 2003/072035
WO 2003/072036
WO 2003/077836
WO 2003/081210
WO 2003/083041
WO 2003/083047
WO 2003/083074
WO 2003/087306
WO 2003/087768
WO 2003/088808
WO 2003/089624
WO 2003/089904
WO 2003/093444
WO 2003/097803
WO 2003/101283
WO 2003/101400
WO 2003/104270
WO 2003/104275
WO 2003/105758
WO 2003004529
WO 2003042661
WO 2003104399
WO 2004/000997
WO 2004/001004
WO 2004/009622
WO 2004/011611
WO 2004/015426

WO 2004/016225
WO 2004/020595
WO 2004/022709
WO 2004/022778
WO 2004/027049
WO 2004/031238
WO 20041/032828
WO 2004/032842
WO 2004/040000
WO 2004/043361
WO 2004/043963
WO 2004/044178
WO 2004/045516
WO 2004/045520
WO 2004/045553
WO 2004/046342
WO 2004/047749
WO 2004/048938
WO 2004/053079
WO 2004/063355
WO 2004/063362
WO 2004/063709
WO 2004/065577
WO 2004/074320
WO 2004000221
WO 2004020583
WO 2004042346
WO 2004065576
WO 2005/023814
WO 2005/082023
WO 2005/085251
WO 2006/111759
WO 2007/044515
WO 2007/085930
WO 2009/052249
WO 2010/091150
WO 91/02536
WO 92/07574
WO 92/17497
WO 94/10312
WO 94/28931
WO 9630514
WO 97/07198
WO 97/44452
WO 98/13059
WO 98/37193
WO 98/40403
WO 98/51805
WO 98/51824
WO 99/28468
WO 99/46284
WO 99/58658
Am. J. Hum. Genet. 49 (3):555-565 (1991)
Amiel J., et al Hum. Mol. Genet. 5, 355-357, 1996
Amir et al (2003) Angew. Chem. Int. Ed. 42:4494-4499
Amsberry, et al (1990) J. Org. Chem. 55:5867
Angew Chem. Intl. Ed. Engl. (1994) 33:183-186
Annu. Rev. Neurosci. 21:309-345 (1998)
Arai H., et al J. Biol. Chem. 268, 3463-3470, 1993
Arai H., et al Jpn. Circ. J. 56, 1303-1307, 1992
Arima, et al., J. Antibiotics, 25, 437-444 (1972)
Attie T., et al, Hum. Mol. Genet. 4, 2407-2409, 1995
Auricchio A., et al Hum. Mol. Genet. 5:351-354, 1996
Barel M., et al Mol. Immunol. 35, 1025-1031, 1998
Barella et al (1995) Biochem. J. 309:773-779
Barnett T., et al Genomics 3, 59-66, 1988
Beck et al (1992) J. Mol. Biol. 228:433-441
Beck et al (1996) J. Mol. Biol. 255:1-13
Berge, et al., J. Pharm. Sci., 66, 1-19 (1977)
Biochem. Biophys. Res. Commun. (2000) 275(3):783-788
Biochem. Biophys. Res. Commun. 255 (2), 283-288 (1999)
Blood (2002) 100 (9):3068-3076
Blood 99 (8):2662-2669 (2002)
Blumberg H., et al Cell 104, 9-19, 2001
Bose, et al., Tetrahedron, 48, 751-758 (1992)
Bourgeois C., et al J. Clin. Endocrinol. Metab. 82, 3116-3123, 1997
Brinster et al (1988) Proc. Natl. Acad. Sci. USA 85:836
Buchman and Berg (1988) Mol. Cell. Biol. 8:4395
Cancer Res. 61 (15), 5857-5860 (2001)
Carl et al (1981) J. Med. Chem. 24:479-480
Carlsson et al (1978) Biochem. J. 173:723-737
Carter, P. (2006) Nature Reviews immunology 6:343-357
Cell 109 (3):397-407 (2002)
CellTiter Glo Luminescent Cell Viability Assay, Promega Corp. Technical Bulletin TB288
Chakravarty et al (1983) J. Med. Chem. 26:638-644
Chan, J. and Watt, V. M., Oncogene 6 (6), 1057-1061 (1991)
Child et al (1999) J. Biol. Chem. 274: 24335-24341
Cho H.-S., et al Nature 421, 756-760, 2003
Ciccodicola, A., et al EMBO J. 8(7):1987-1991 (1989)
Clackson et al (1991) Nature, 352:624-628
Clark H. F., et al Genome Res. 13, 2265-2270, 2003
Corey E, Quinn J E, Buhler K R, et al. LuCap 35: a new model of prostate cancer progression to androgen independence. The Prostate 2003; 55:239-46
Coussens L., et al Science (1985) 230(4730):1132-1139
Cree et al (1995) AntiCancer Drugs 6:398-404
Crouch et al (1993) J. Immunol. Meth. 160:81-88
Davis et al (2001) Proc. Natl. Acad. Sci USA 98(17):9772-9777
de Groot et al (2001) J. Org. Chem. 66:8815-8830
de Groot et al (2003) Angew. Chem. Int. Ed. 42:4490-4494
Dennis et al. (2002) "Albumin Binding As A General Strategy For improving The Pharmacokinetics Of Proteins" J Biol Chem. 277:35035-35043
Dobner et al (1992) Eur. J. Immunol. 22:2795-2799
Doman et al (2009) Blood 114(13):2721-2729
Doronina et al (2006) Bioconj. Chem. 17:114-124
Dubowchik et al. Bioconjugate Chemistry, 2002, 13, 855-869
Dubowchik, et al. (1997) Tetrahedron Letters, 38:5257-60
Dumoutier L., et al J. Immunol. 167, 3545-3549, 2001
E. Schröder and K. Lübke, The Peptides, volume 1, pp 76-136 (1965) Academic Press
Ehsani A., et al (1993) Genomics 15, 426-429
Eliel, E. and Wilen, S., "Stereochemistry of Organic Compounds", John Wiley & Sons, Inc., New York, 1994
Elshourbagy N. A., et al J. Biol. Chem. 268, 3873-3879, 1993
Erickson et al (2006) Cancer Res. 66(8):1-8
Feild, J. A., et al (1999) Biochem. Biophys. Res. Commun. 258 (3):578-582
Fields, G. and Noble, R. (1990) "Solid phase peptide synthesis utilizing 9-fluoroenylmethoxycarbonyl amino acids", Int. J. Peptide Protein Res. 35:161-214
Fuchs S., et al Mol. Med. 7, 115-124, 2001
Fujisaku et al (1989) J. Biol. Chem. 264 (4):2118-2125)
Gary S. C., et al Gene 256, 139-147, 2000
Gaugitsch, H. W., et al (1992) J. Biol. Chem. 267 (16): 11267-11273)
Geiser et al "Automation of solid-phase peptide synthesis" in Macromolecular Sequencing and Synthesis, Alan R. Liss, Inc., 1988, pp. 199-218

Genome Res. 13 (10):2265-2270 (2003)
Genomics 62 (2):281-284 (1999)
Geoghegan & Stroh, (1992) Bioconjugate Chem. 3:138-146
Getz et al (1999) Anal. Biochem. Vol 273:73-80
Glynne-Jones et al (2001) Int J Cancer. October 15; 94(2): 178-84
Gregson et al., Chem. Commun. 1999, 797-798
Gregson et al., J. Med. Chem. 2001, 44, 1161-1174
Gu Z., et al Oncogene 19, 1288-1296, 2000
Ha et al (1992) J. Immunol. 148(5):1526-1531
Haendler B., et al J. Cardiovasc. Pharmacol. 20, s1-S4, 1992
Hamann P. (2005) Expert Opin. Ther. Patents 15(9):1087-1103
Hamblett et al (2004) Clin. Cancer Res. 10:7063-7070
Handbook of Pharmaceutical Additives, 2nd Edition (eds. M. Ash and I. Ash), 2001 (Synapse Information Resources, Inc., Endicott, N.Y., USA)
Handbook of Pharmaceutical Excipients, 2nd edition, 1994
Hara, et al., J. Antibiotics, 41, 702-704 (1988)
Hashimoto et al (1994) Immunogenetics 40(4):287-295
Hay et al. (1999) Bioorg. Med. Chem. Lett. 9:2237
Herdwijn, P. et al., Canadian Journal of Chemistry. 1982, 60, 2903-7
Hermanson, G. T. (1996) Bioconjugate Techniques; Academic Press: New York, p 234-242
Hochlowski, et a., J. Antibiotics, 40, 145-148 (1987)
Hofstra R. M. W., et al Eur. J. Hum. Genet. 5, 180-185, 1997
Hofstra R. M. W., et al Nat. Genet. 12, 445-447, 1996
Horie et al (2000) Genomnics 67:146-152
Hubert, R. S., et al (1999) Proc. Natl. Acad. Sci. U.S.A. 96 (25):14523-14528)
Hurley and Needham-VanDevanter, Acc. Chem. Res., 19, 230-237 (1986)
Immunogenetics 54 (2):87-95 (2002)
Int. Rev. Cytol. 196:177-244 (2000)
Itoh, et al., J. Antibiotics, 41, 1281-1284 (1988)
J. Biol. Chem. 270 (37):21984-21990 (1995)
J. Biol. Chem. 276 (29):27371-27375 (2001)
J. Biol. Chem. 277 (22):19665-19672 (2002)
J. Biol. Chem. 278 (33):30813-30820 (2003)
Janeway, C., Travers, P., Walport, M., Shlomchik (2001) Immuno Biology, 5th Ed., Garland Publishing, New York
Jeffrey at al (2005) J. Med. Chem. 48:1344-1358
Jonsson et al (1989) Immunogenetics 29(6):411-413
Junutula, et al., 2008b Nature Biotech., 26(8):925-932
Kang, G-D., et al., Chem. Commun., 2003, 1680-1689
Kasahara et al (1989) Immunogenetics 30(1):66-68
King eat al (2002) Tetrahedron Letters 43:1987-1990
Kingsbury e al (1984) J. Med. Chem. 27:1447
Kohler et al (1975) Nature 256:495
Kohn, in Antibiotics III. Springer-Verlag, New York, pp. 3-11 (1975).
Konishi, et al., J. Antibiotics, 37, 200-206 (1984)
Kovtun et al (2006) Cancer Res. 66(6):3214-3121
Kuhns J. J., et al J. Biol. Chem. 274, 36422-36427, 1999
Kuminoto, et al., J. Antibiotics, 33, 665-667 (1980)
Kurebayashi et al (1999) Brit. Jour. Cancer 79(5-6):707-717
Lab. Invest. 82 (11):1573-1582 (2002)
Lambert J. (2005) Current Opin. in Pharmacol. 5:543-549
Langley and Thurston, J. Org. Chem., 52, 91-97 (1987)
Larhammar et al (1985) J. Biol. Chem. 260(26):14111-14119
Law et al (2006) Cancer Res. 66(4):2328-2337
Le et al (1997) FEBS Lett. 418(1-2):195-199
Leber, et al., J. Am. Chem. Soc., 110, 2992-2993 (1988)
Leimgruber, et al., J. Am. Chem. Soc., 87, 5791-5793 (1965)
Leimgruber, et al., J. Am. Chem. Soc., 87, 5793-5795 (1965)
Levenson et al (1997) Cancer Res. 57(15):3071-3078
Liang et al (2000) Cancer Res. 60:4907-12
Manfré, F. et al., J. Org. Chem. 1992, 57, 2060-2065
Marks et al (1991) J. Mol. Biol., 222:581-597
McDonagh (2006) Protein Eng. Design & Sel., 19(7): 299-307
Mendoza et al (2002) Cancer Res. 62:5485-5488
Miller et al (2003) Jour. of Immunology 170:4854-4861
Miura et al (1996) Genomics 38(3):299-304
Miura et al (1998) Blood 92:2815-2822
Moore M., et al Proc. Natl. Acad. Sci. U.S.A. 84, 9194-9198, 1987
Morrison et al (1984) Proc. Natl. Acad. Sci. USA, 81:6851-6855
Muller et al (1992) Eur. J. Immunol. 22 (6):1621-1625
Mungall A. J., et al Nature 425, 805-811, 2003
Nagase T., et al (2000) DNA Res. 7 (2):143-150)
Nakamuta M., et al Biochem. Biophys. Res. Commun. 177, 34-39, 1991
Nakayama et al (2000) Biochem. Biophys. Res. Commun. 277(1):124-127
Naruse et al (2002) Tissue Antigens 59:512-519
Nature 395 (6699):288-291 (1998)
Neuberger and Williams (1988) Nucleic Acids Res. 16:6713
Novabiochem Catalog 2006/2007
Ogawa Y., et al Biochem. Biophys. Res. Commun. 178, 248-255, 1991
Okamoto Y., et al Biol. Chem. 272, 21589-21596, 1997
Oncogene 10 (5):897-905 (1995)
Oncogene 14(11):1377-1382 (1997))
Parrish-Novak J., et al J. Biol. Chem. 277, 47517-47523, 2002
Payne, G. (2003) Cancer Cell 3:207-212
Phillips et al (2008) Cancer Res. 68(22):9280-9290
Pingault V., et al (2002) Hum. Genet. 111, 198-206
Pletnev S., et al (2003) Biochemistry 42:12617-12624
Preud'homme et al (1992) Clin. Exp. Immunol. 90(1):141-146
Proc. Natl. Acad. Sci. U.S.A. (2003) 100 (7):4126-4131
Proc. Natl. Acad. Sci. U.S.A. 93 (1):136-140 (1996)
Proc. Natl. Acad. Sci. U.S.A. 98 (17):9772-9777 (2001)
Proc. Natl. Acad. Sci. U.S.A. 99 (26):16899-16903 (2002)
Proc. Natl. Acad. Sci. U.S.A. 96 (20):11531-11536 (1999)
Protective Groups in Organic Synthesis, Greene and Wuts, 3rd Edition, 1999, John Wiley & Sons Inc.
Puffenberger E. G., et al Cell 79, 1257-1266, 1994
Rao et al (1997) Breast Cancer Res. and Treatment 45:149-158
Reiter R. E., et al Proc. Natl. Acad. Sci. U.S.A. 95, 1735-1740, 1998
Remington's Pharmaceutical Sciences, 20th edition, pub. Lippincott, Williams & Wilkins, 2000
Rodrigues et al (1995) Chemistry Biology 2:223
Ross et al (2002) Cancer Res. 62:2546-2553
S. P. Parker, Ed., McGraw-Hill Dictionary of Chemical Terms (1984) McGraw-Hill Book Company, New York
Sakaguchi et al (1988) EMBO J. 7(11):3457-3464
Sakamoto A., Yanagisawa M., et al Biochem. Biophys. Res. Commun. 178, 656-663, 1991
Sanderson et al (2005) Clin. Cancer Res. 11:843-852
Semba K., et al Proc. Natl. Acad. Sci. U.S.A. 82, 6497-6501, 1985
Servenius et al (1987) J. Biol. Chem. 262:8759-8766
Shamis et al (2004) J. Am. Chem. Soc. 126:1726-1731
Sheikh F., et al (2004) J. Immunol. 172, 2006-2010
Shimizu, et al, J. Antibiotics, 29, 2492-2503 (1982)
Sinha S. K., et al (1993) J. Immunol. 150, 5311-5320

Storm et al (1972) J. Amer. Chem. Soc. 94:5815
Strausberg et al (2002) Proc. Natl. Acad. Sci USA 99:16899-16903
Sun et al (2002) Bioorganic & Medicinal Chemistry Letters 12:2213-2215
Sun et al (2003) Bioorganic & Medicinal Chemistry 11:1761-1768
Svensson P. J., et al Hum. Genet. 103, 145-148, 1998
Swiercz J. M., et al J. Cell Biol. 165, 869-880, 2004
Syrigos and Epenetos (1999) Anticancer Research 19:605-614
Takeuchi, et al., J. Antibiotics, 29, 93-96 (1976)
Tawaragi Y., et al Biochem. Biophys. Res. Commun. 150, 89-96, 1988
ten Dijke, P., et al Science 264 (5155):101-104 (1994)
Thompson, J. S., et al Science 293 (5537), 2108-2111 (2001) WO 2004/058309
Thurston, et al., Chem. Brit., 26, 767-772 (1990)
Thurston, et al., Chem. Rev. 1994, 433-465 (1994)
Toki et al (2002) J. Org. Chem. 67:1866-1872
Tonnelle et al (1985) EMBO J. 4(11):2839-2847
Touchman et al (2000) Genome Res. 10:165-173
Trail et al (2003) Cancer Immunol. Immunother. 52:328-337
Tsunakawa, et al., J. Antibiotics, 41, 1366-1373 (1988)
Tsutsumi M., et al Gene 228, 43-49, 1999
Uchida et al (1999) Biochem. Biophys. Res. Commun. 266:593-602
Verheij J. B., et al Am. J. Med. Genet. 108, 223-225, 2002
Von Hoegen et al (1990) J. Immunol. 144(12):4870-4877
Webster et al (1994) Semin. Cancer Biol. 5:69-76
Weis J. J., eat al J. Exp. Med. 167, 1047-1066, 1988
Weis J. J., et al Proc. Natl. Acad. Sci. U.S.A. 83, 5639-5643, 1986
Wilson et al (1991) J. Exp. Med. 173:137-146
Wu et al (2005) Nature Biotech. 23(9):1137-1145
Xie et al (2006) Expert. Opin. Biol. Ther. 6(3):281-291
Xu, M. J., et al (2001) Biochem. Biophys. Res. Commun. 280 (3):768-775 WO 2004/016225
Xu, X. Z., at al Proc. Natl. Acad. Sci. U.S.A. 98 (19):10692-10697 (2001)
Yamaguchi, N., et al Biol. Chem. 269 (2), 805-808 (1994)
Yamamoto T., et al Nature 319, 230-234, 1986
Yu et al (1992) J. Immunol. 148(2) 633-637

The invention claimed is:

1. A conjugate of formula (Ia):

Ia

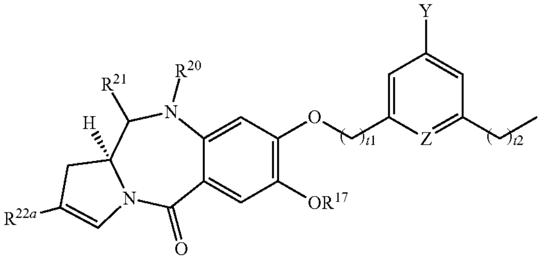

-continued

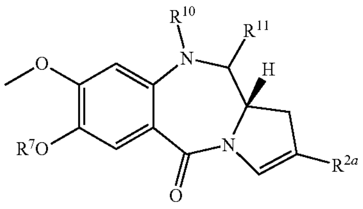

wherein:

$R^{2a}$ and $R^{22a}$ are independently selected from the group consisting of:

(ia)
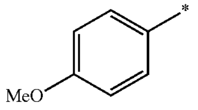
,
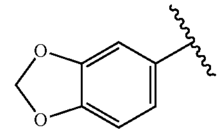
and
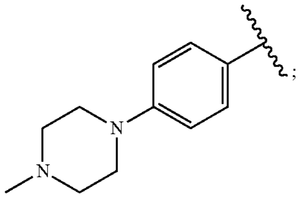
;
(ib)
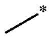
;
(ic)
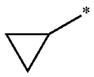
;
(id)
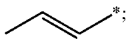
;
(ie)
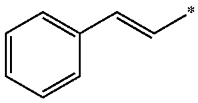
;
and
(if)
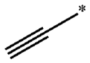
;
$R^{7a}$ and $R^{17a}$ are independently selected from methyl and phenyl;
Y is selected from formulae A1, A2, A3, A4, A5 and A6:
(A1)
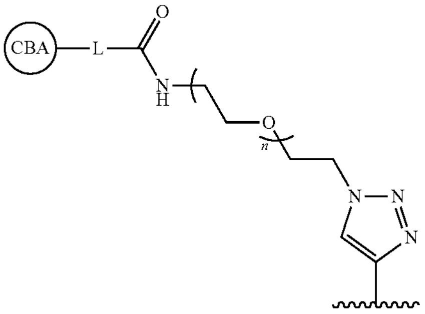
(A2)
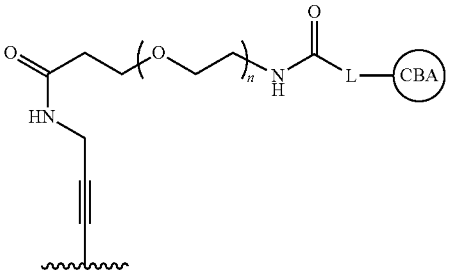
(A3)
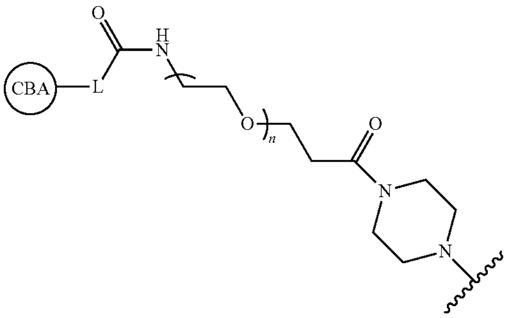
(A4)
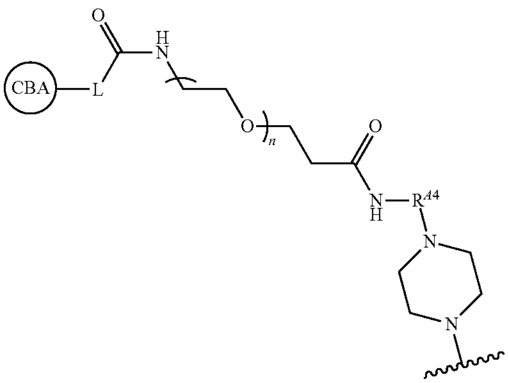

-continued
(A5)
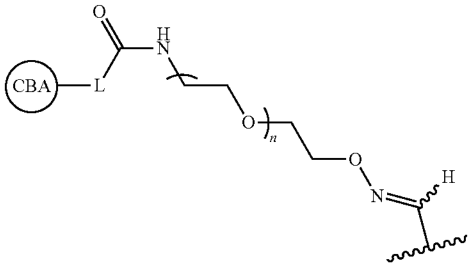
(A6)
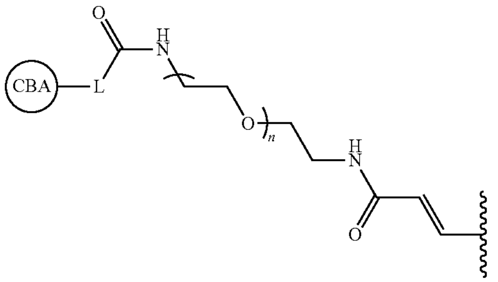
L is a linker connected to a cell binding agent and is of formula:
(a) $-L^A-(CH_2)_m-$ (L1)
where m is from 0 to 6; and
$L^A$ is selected from:
($L^{A1-1}$)
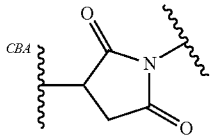
($L^{A1-2}$)
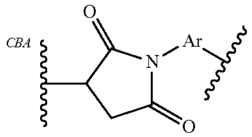
($L^{A2}$)
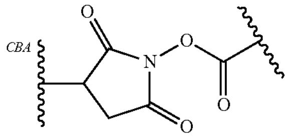
($L^{A3-1}$)
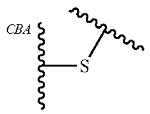
($L^{A3-2}$)
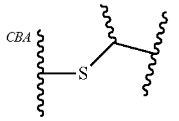
-continued
($L^{A4}$)
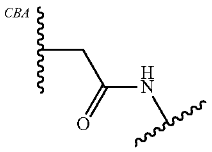
($L^{A5}$)
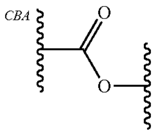
($L^{A6}$)
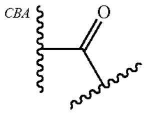
($L^{A7}$)
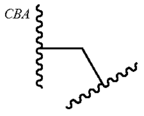
($L^{A8-1}$)
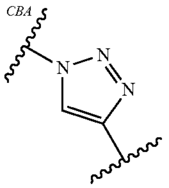
($L^{A8-2}$)
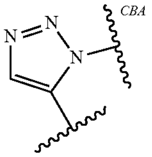
($L^{A9-1}$)
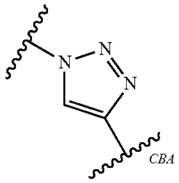
($L^{A9-2}$)
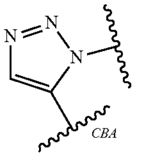
where Ar represents a phenylene group;
(b) $-L^A-(CH_2)_m-O-$ (L2)
Where m is from 0 to 6;
(c) $-L^A-(CH_2)_q-O-C(=O)-NH-(CH_2)_p-$ (L3)

Where q is from 1 to 3, and p is from 1 to 3; or (d)

(L4)

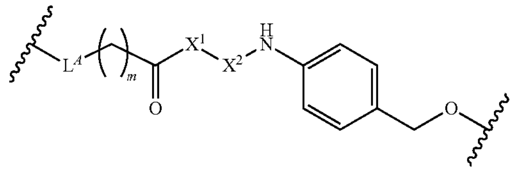

Where m is from 0 to 6;

$X^1$ and $X^2$ are amino acid groups, selected from natural amino acids, which may be modified;

CBA is the cell binding agent which is an antibody or an active fragment thereof;

n is an integer selected in the range of 0 to 48;

$R^{A4}$ is a $C_{1-6}$ alkylene group;

either (a) $R^{10}$ is H, and $R^{11}$ is OH, $OR^A$, where $R^A$ is $C_{1-4}$ alkyl; or (b) $R^{10}$ and $R^{11}$ form a nitrogen-carbon double bond between the nitrogen and carbon atoms to which they are bound; or (c) $R^{10}$ is H and $R^{11}$ is $OSO_zM$, where z is 2 or 3 and M is a monovalent pharmaceutically acceptable cation;

wherein Z is CH or N;

$t_1$ and $t_2$ are an independently selected from 0, 1 and 2.

2. The conjugate according to claim 1, wherein $R^{7a}$ is Me.

3. The conjugate according to claim 1, wherein $R^{10}$ and $R^{11}$ form a nitrogen-carbon double bond between the nitrogen and carbon atoms to which they are bound.

4. The conjugate according to claim 1, wherein $R^{17a}$, $R^{20}$, $R^{21}$ and $t_2$ are the same as $R^{7a}$, $R^{10}$, $R^{11}$ and $t_1$ respectively.

5. The conjugate according to claim 1, wherein the group $—X_1—X_2—$ is selected from:

-Phe-Lys-,

-Val-Ala-,

-Val-Lys-,

-Ala-Lys-,

-Val-Cit-.

6. The conjugate according to claim 1, wherein the cell binding agent is an antibody or an active fragment thereof.

7. The conjugate of claim 6, wherein the antibody or antibody fragment is an antibody which binds to one or more tumor-associated antigens or cell-surface receptors selected from (1)-(36):

(1) BMPR1B (bone morphogenetic protein receptor-type IB);

(2) E16 (LAT1, SLC7A5);

(3) STEAP1 (six transmembrane epithelial antigen of prostate);

(4) 0772P (CA125, MUC16);

(5) MPF (MPF, MSLN, SMR, megakaryocyte potentiating factor, mesothelin);

(6) Napi3b (NAPI-3B, NPTIIb, SLC34A2, solute carrier family 34 (sodium phosphate), member 2, type II sodium-dependent phosphate transporter 3b);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);

(9) ETBR (Endothelin type B receptor);

(10) MSG783 (RNF124, hypothetical protein FLJ20315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR (C3d/Epstein Barr virus receptor) or Hs 73792);

(15) CD79b (CD79B, CD79(3, IGb (immunoglobulin-associated beta), B29);

(16) FcRH2 (IFGP4, IRTA4, SPAP1A (SH2 domain containing phosphatase anchor protein 1a), SPAP1B, SPAP1C);

(17) HER2;

(18) NCA;

(19) MDP;

(20) IL20Rα;

(21) Brevican;

(22) EphB2R;

(23) ASLG659;

(24) PSCA;

(25) GEDA;

(26) BAFF-R (B cell-activating factor receptor, BLyS receptor 3, BR3);

(27) CD22 (B-cell receptor CD22-B isoform);

(28) CD79a (CD79A, CD79α, immunoglobulin-associated alpha);

(29) CXCR5 (Burkitt's lymphoma receptor 1);

(30) HLA-DOB (Beta subunit of MHC class II molecule (Ia antigen));

(31) P2X5 (Purinergic receptor P2X ligand-gated ion channel 5);

(32) CD72 (B-cell differentiation antigen CD72, Lyb-2);

(33) LY64 (Lymphocyte antigen 64 (RP105), type I membrane protein of the leucine rich repeat (LRR) family);

(34) FcRH1 (Fc receptor-like protein 1);

(35) IRTA2 (Immunoglobulin superfamily receptor translocation associated 2);

(36) TENB2 (putative transmembrane proteoglycan);

(37) CD33 (CD33 molecule, SIGLEC-3, SIGLEC3, p67; CD33 antigen (gp67);

gp67; myeloid cell surface antigen CD33; sialic acid binding Ig-like lectin 3; sialic acid-binding Ig-like lectin); and

(38) LGR5/GPR49.

8. A pharmaceutical composition comprising the conjugate of claim 1, and a pharmaceutically acceptable diluent, carrier or excipient.

9. A method of treating breast cancer comprising administering to a patient in need thereof the pharmaceutical composition of claim 8.

10. A compound of formula (IIa):
IIa
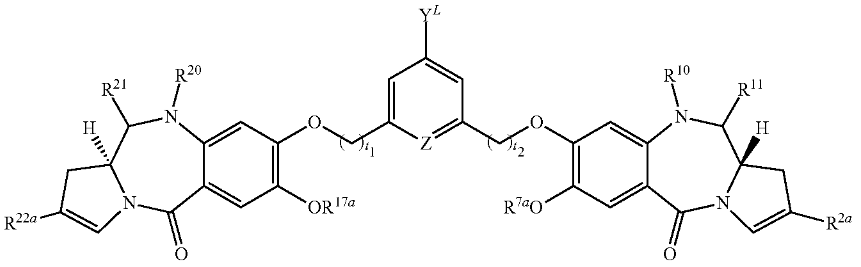
wherein:
$R^{2a}$ and $R^{22a}$ are independently selected from the group consisting of:
(ia)
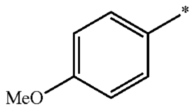
, 
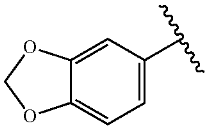
and
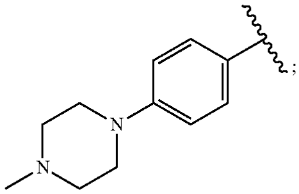
;
(ib)
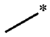
;
(ic)
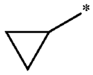
;
(id)
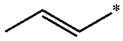
;
(ie)
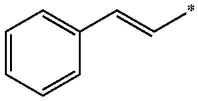
; and
(if)
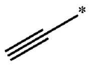
;
$R^{7a}$ and $R^{17a}$ are independently selected from methyl and phenyl;
$t_1$ and $t_2$ are an independently selected from 0, 1 and 2;
$Y^L$ is selected from a group of formulae B1, B2, B3, B4, B5 and B6:
(B1)
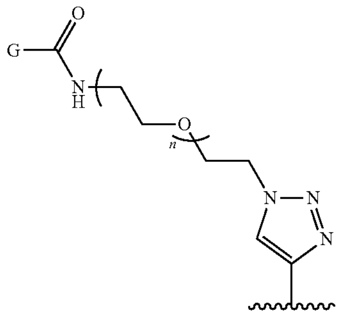
(B2)
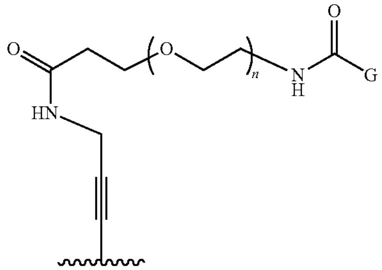
(B3)
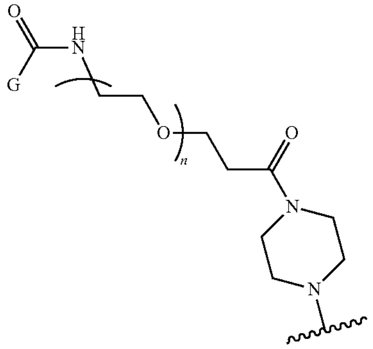

-continued
(B4)
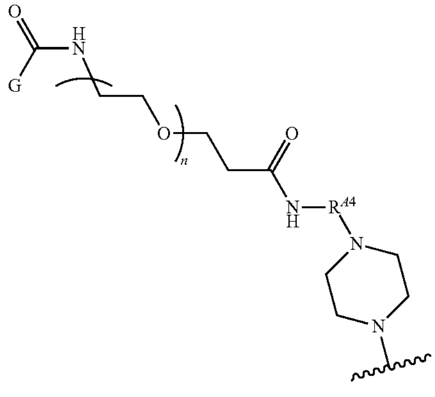
(B5)
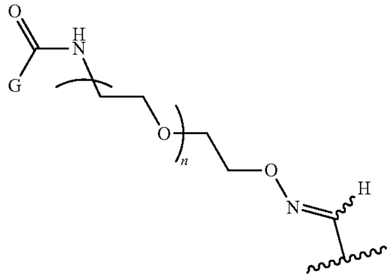
(B6)
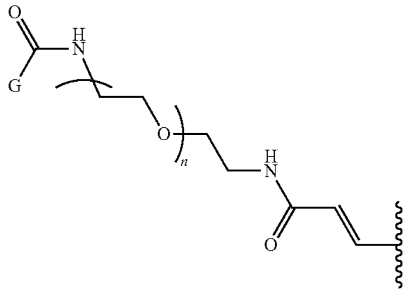
G is a reactive group for connecting to a cell binding agent which is of formula:
(a) $G^A$—$(CH_2)_m$— (G1)
where m is from 0 to 6; and
$G^A$ is selected from:
($G^{A1-1}$)
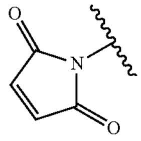
($G^{A1-2}$)
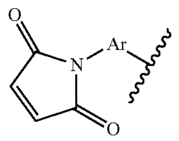
-continued
($G^{A2}$)
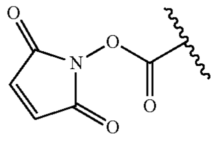
($G^{A3-1}$)
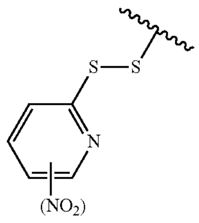
where the $NO_2$ group is optional
($G^{A3-2}$)
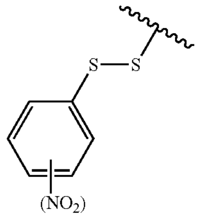
where the $NO_2$ group is optional
($G^{A3-3}$)
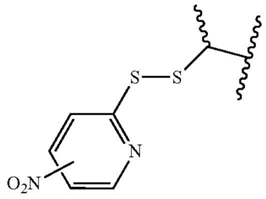
where the $NO_2$ group is optional
($G^{A3-4}$)
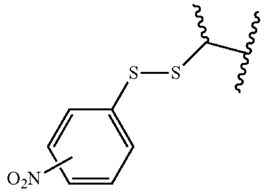
where the $NO_2$ group is optional -continued ($G^{A4}$)

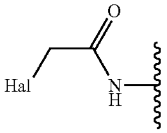

Where Hal = I, Br, Cl ($G^{A5}$)

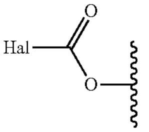

where q is from 1 to 3, and p is from 1 to 3; or (d)

(G4)

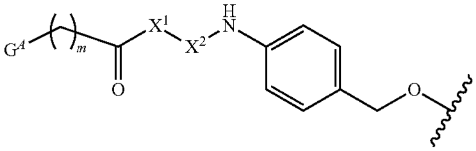

where m is from 0 to 6;

$X^1$ and $X^2$ are amino acid groups, selected from natural amino acids, which may be modified;

wherein n is an integer selected in the range of 0 to 48; and $R^{A4}$ is a $C_{1-6}$ alkylene group.

11. A compound of formula (IIIa):

IIIa

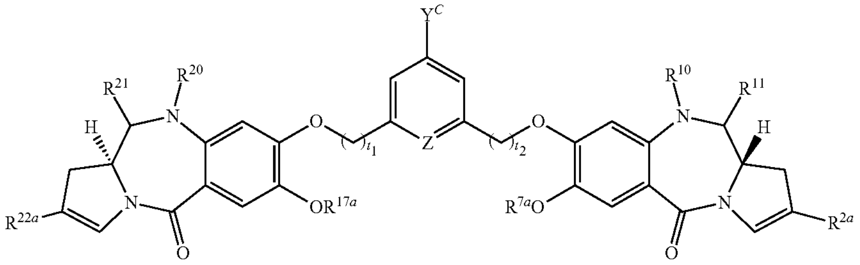

-continued ($G^{A6}$)

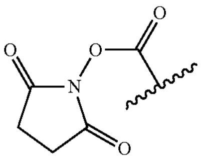

($G^{A7}$)

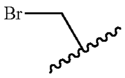

($G^{A8}$)

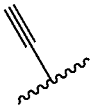

($G^{A9}$)

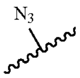

where Ar represents a phenylene group;

(b) $G^A$—$(CH_2)_n$—O— (G2)

where m is from 0 to 6;

$G^A$—$(CH_2)_q$—O—C(=O)—NH—$(CH_2)_q$— (G3)

wherein:

$R^{2a}$ and $R^{22a}$ are independently selected from the group consisting of:

(ia)

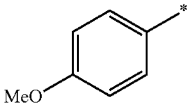

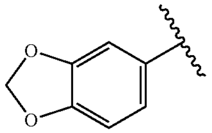

and

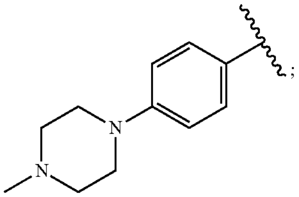

;

(ib)

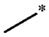

;

(ic)

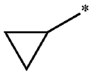

;

(id)

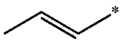

;

(ie)

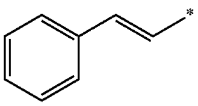

; and

-continued (if)

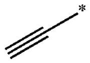 ;

$R^{7a}$ and $R^{17a}$ are independently selected from methyl and phenyl;

$t_1$ and $t_2$ are an independently selected from 0, 1 and 2;

$Y^C$ is selected from a group of formulae C1, C2, C3, C4, C5 and C6:

(C1)

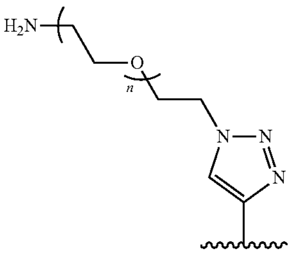

(C2)

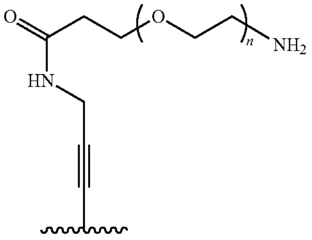

(C3)

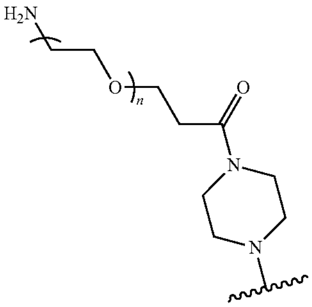

-continued (C4)

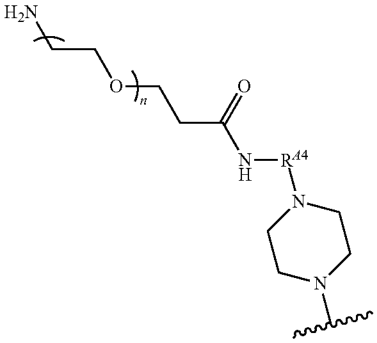

(C5)

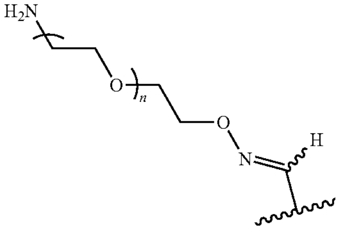

(C6)

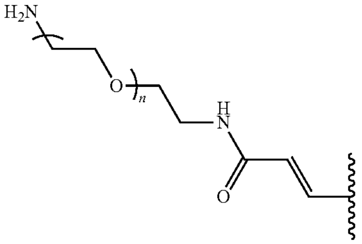

wherein n is an integer selected in the range of 0 to 48;

$R^{A4}$ is a $C_{1-6}$ alkylene group;

either (a) $R^{30}$ is H, and $R^{31}$ is OH, $OR^A$, where $R^A$ is $C_{1-4}$ alkyl; or (b) $R^{30}$ and $R^{31}$ form a nitrogen-carbon double bond between the nitrogen and carbon atoms to which they are bound; or (c) $R^{30}$ is H and $R^{31}$ is $OSO_zM$, where z is 2 or 3 and M is a monovalent pharmaceutically acceptable cation; or (d) $R^{30}$ is a nitrogen protecting group and $R^{31}$ is $OProt^O$, where $Prot^O$ is a hydroxy protecting group; and $R^{40}$ and $R^{41}$ are as defined for $R^{30}$ and $R^{31}$ respectively.

12. A compound of formula (IVa):

IVa

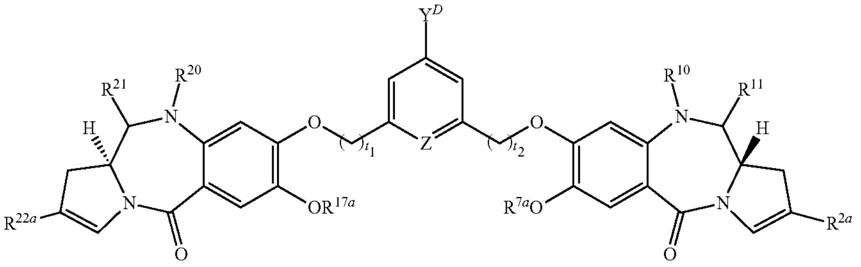

wherein:

$R^{2a}$ and $R^{22a}$ are independently selected from the group consisting of:

(ia)

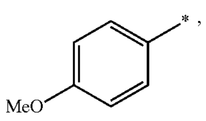

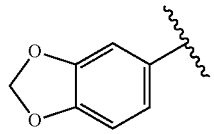

and

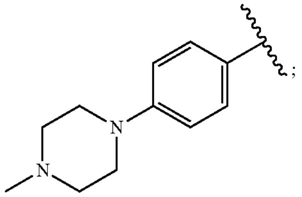

(ib)

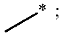

(ic)

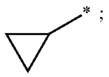

(id)

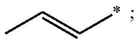

(ie)

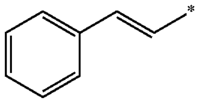

; and (if)

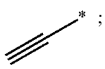

$R^{7a}$ and $R^{17a}$ are independently selected from methyl and phenyl;

$t_1$ and $t_2$ are an independently selected from 0, 1 and 2;

$R^{30}$, $R^{31}$, $R^{40}$ and $R^{41}$ are either (a) $R^{30}$ is H, and $R^{31}$ is OH, $OR^A$, where $R^A$ is $C_{1-4}$ alkyl; or (b) $R^{30}$ and $R^{31}$ form a nitrogen-carbon double bond between the nitrogen and carbon atoms to which they are bound; or (c) $R^{30}$ is H and $R^{31}$ is $OSO_zM$, where z is 2 or 3 and M is a monovalent pharmaceutically acceptable cation; or (d) $R^{30}$ is a nitrogen protecting group and $R^{31}$ is $OProt^O$, where $Prot^O$ is a hydroxy protecting group; and $R^{40}$ and $R^{41}$ are as defined for $R^{30}$ and $R^{31}$ respectively;

$Y^D$ is selected from a group of formulae D2, D3, D4 and D6:

(D2)

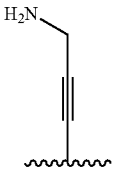

(D3)

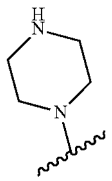

(D4)

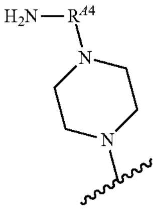

(D5)

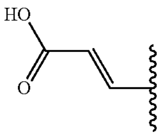

wherein $R^{A4}$ is a $C_{1-6}$ alkylene group.

13. A compound of formula (E):

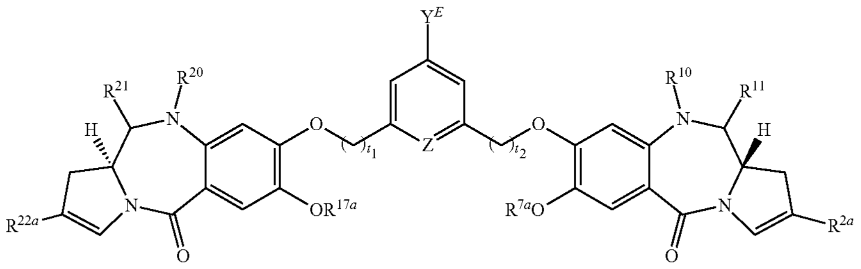

Va wherein:

$R^{2a}$ and $R^{22a}$ are independently selected from the group consisting of:

(ia)

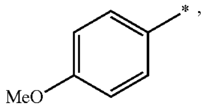
,
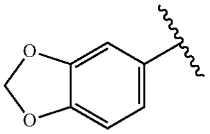
and
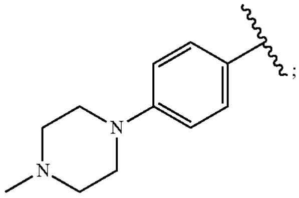
;

(ib)

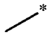
;

(ic)

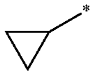
;

(id)

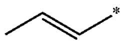
;

(ie)

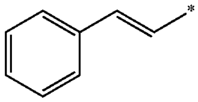
; and (if)

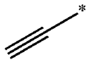
;

$R^{7a}$ and $R^{17a}$ are independently selected from methyl and phenyl;

$t_1$ and $t_2$ are an independently selected from 0, 1 and 2;

$R^{30}$, $R^{31}$, $R^{40}$ and $R^{41}$ are either (a) $R^{30}$ is H, and $R^{31}$ is OH, $OR^A$, where $R^A$ is $C_{1-4}$ alkyl; or (b) $R^{30}$ and $R^{31}$ form a nitrogen-carbon double bond between the nitrogen and carbon atoms to which they are bound; or (c) $R^{30}$ is H and $R^{31}$ is $OSO_zM$, where z is 2 or 3 and M is a monovalent pharmaceutically acceptable cation; or (d) $R^{30}$ is a nitrogen protecting group and $R^{31}$ is $OProt^O$, where $Prot^O$ is a hydroxy protecting group; and $R^{40}$ and $R^{41}$ are as defined for $R^{30}$ and $R^{31}$ respectively;

$Y^E$ is selected from a group of formulae E1, E2 and E5:

(E1)

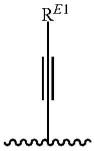

(E2)

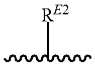

(E5)

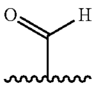

where $R^{E1}$ is selected from H and TMS; and $R^{E2}$ is selected from Br, Cl and I.

* * * * *

SEQUENCE LISTING

```
<160> NUMBER OF SEQ ID NOS: 7

<210> SEQ ID NO 1
<211> LENGTH: 16
<212> TYPE: PRT
<213> ORGANISM: Artificial sequence
<220> FEATURE:
<223> OTHER INFORMATION: Synthetic sequence: Antibody drug conjugate CDR
      L1

<400> SEQUENCE: 1

Arg Ser Ser Glu Thr Leu Val His Ser Ser Gly Asn Thr Tyr Leu Glu
1               5                   10                  15


<210> SEQ ID NO 2
<211> LENGTH: 7
<212> TYPE: PRT
<213> ORGANISM: Artificial sequence
<220> FEATURE:
<223> OTHER INFORMATION: Synthetic sequence: Antibody drug conjugate CDR
      L2

<400> SEQUENCE: 2

Arg Val Ser Asn Arg Phe Ser
1               5


<210> SEQ ID NO 3
<211> LENGTH: 9
<212> TYPE: PRT
<213> ORGANISM: Artificial sequence
<220> FEATURE:
<223> OTHER INFORMATION: Synthetic sequence: Antibody drug conjugate CDR
      L3

<400> SEQUENCE: 3

Phe Gln Gly Ser Phe Asn Pro Leu Thr
1               5
```

-continued

<210> SEQ ID NO 4
<211> LENGTH: 10
<212> TYPE: PRT
<213> ORGANISM: Artificial sequence
<220> FEATURE:
<223> OTHER INFORMATION: Synthetic sequence: Antibody drug conjugate CDR H1

<400> SEQUENCE: 4

```
Gly Phe Ser Phe Ser Asp Phe Ala Met Ser
1               5                   10
```

<210> SEQ ID NO 5
<211> LENGTH: 18
<212> TYPE: PRT
<213> ORGANISM: Artificial sequence
<220> FEATURE:
<223> OTHER INFORMATION: Synthetic sequence: Antibody drug conjugate CDR H2

<400> SEQUENCE: 5

```
Ala Thr Ile Gly Arg Val Ala Phe His Thr Tyr Tyr Pro Asp Ser Met
1               5                   10                  15

Lys Gly
```

<210> SEQ ID NO 6
<211> LENGTH: 13
<212> TYPE: PRT
<213> ORGANISM: Artificial sequence
<220> FEATURE:
<223> OTHER INFORMATION: Synthetic sequence: Antibody drug conjugate CDR H3

<400> SEQUENCE: 6

```
Ala Arg His Arg Gly Phe Asp Val Gly His Phe Asp Phe
1               5                   10
```

<210> SEQ ID NO 7
<211> LENGTH: 21
<212> TYPE: PRT
<213> ORGANISM: Artificial Sequence
<220> FEATURE:
<223> OTHER INFORMATION: Synthetic sequence: A20FMDV-Cys

<400> SEQUENCE: 7

```
Asn Ala Val Pro Asn Leu Arg Gly Asp Leu Gln Val Leu Ala Gln Lys
1               5                   10                  15

Val Ala Arg Thr Cys
            20
```